US011666572B2

(12) United States Patent
Peterson et al.

(10) Patent No.: US 11,666,572 B2
(45) Date of Patent: Jun. 6, 2023

(54) TREATMENT OF HER2 POSITIVE CANCERS

(71) Applicant: Seagen Inc., Bothell, WA (US)

(72) Inventors: Scott Peterson, Bothell, WA (US); Luke Walker, Bothell, WA (US)

(73) Assignee: Seagen Inc., Bothell, WA (US)

( * ) Notice: Subject to any disclaimer, the term of this patent is extended or adjusted under 35 U.S.C. 154(b) by 0 days.

(21) Appl. No.: 17/530,265

(22) Filed: Nov. 18, 2021

(65) Prior Publication Data

US 2022/0168303 A1    Jun. 2, 2022

Related U.S. Application Data

(63) Continuation of application No. 16/607,850, filed as application No. PCT/US2018/029899 on Apr. 27, 2018, now Pat. No. 11,207,324.

(60) Provisional application No. 62/491,872, filed on Apr. 28, 2017.

(51) Int. Cl.
*A61K 31/517* (2006.01)
*A61P 35/00* (2006.01)
*A61K 31/7068* (2006.01)
*A61K 39/395* (2006.01)

(52) U.S. Cl.
CPC ........ *A61K 31/517* (2013.01); *A61K 31/7068* (2013.01); *A61K 39/39558* (2013.01); *A61P 35/00* (2018.01)

(58) Field of Classification Search
CPC .. A61K 31/517; A61K 31/7068; A61K 35/00; A61K 39/39558
See application file for complete search history.

(56) References Cited

U.S. PATENT DOCUMENTS

| | | |
|---|---|---|
| 4,235,871 A | 11/1980 | Papahadjopoulos et al. |
| 4,501,728 A | 2/1985 | Geho et al. |
| 4,837,028 A | 6/1989 | Allen |
| 4,902,505 A | 2/1990 | Pardridge et al. |
| 4,957,735 A | 9/1990 | Huang |
| 5,004,697 A | 4/1991 | Pardridge |
| 5,019,369 A | 5/1991 | Presant et al. |
| 5,055,303 A | 10/1991 | Riley, Jr. |
| 5,188,837 A | 2/1993 | Domb |
| 5,268,164 A | 2/1993 | Kozarich et al. |
| 5,254,342 A | 10/1993 | Shen et al. |
| 5,271,961 A | 12/1993 | Mathiowitz et al. |
| 5,413,797 A | 5/1995 | Khan et al. |
| 5,506,206 A | 4/1996 | Kozarich et al. |
| 5,514,670 A | 5/1996 | Friedman et al. |
| 5,534,496 A | 7/1996 | Lee et al. |
| 8,648,087 B2 | 2/2014 | Lyssikatos et al. |
| 9,168,254 B2 | 10/2015 | Corson et al. |
| 9,457,093 B2 | 10/2016 | Fry et al. |
| 9,693,989 B2 | 7/2017 | Lyssikatos et al. |
| 9,889,134 B2 | 2/2018 | Corson et al. |
| 10,143,692 B2 | 12/2018 | Corson et al. |
| 10,765,678 B2 | 9/2020 | Corson et al. |
| 10,780,073 B2 | 9/2020 | Lyssikatos et al. |
| 11,207,324 B2 | 12/2021 | Peterson et al. |
| 2011/0229406 A1 | 9/2011 | Hettmann et al. |
| 2012/0295259 A1 | 11/2012 | Huang et al. |
| 2014/0023643 A1 | 1/2014 | Lyssikatos et al. |
| 2014/0296267 A1 | 10/2014 | Fry et al. |
| 2017/0136022 A1 | 5/2017 | Fry et al. |
| 2017/0252317 A1 | 9/2017 | Lyssikatos et al. |
| 2018/0169097 A1 | 6/2018 | Hammerman et al. |
| 2018/0271824 A1 | 9/2018 | Lyssikatos et al. |
| 2019/0015411 A9 | 1/2019 | Hammerman et al. |
| 2019/0119284 A1 | 4/2019 | Novotny et al. |
| 2019/0125749 A1 | 5/2019 | Corson et al. |
| 2019/0275043 A1 | 9/2019 | Fry et al. |
| 2020/0188401 A1 | 6/2020 | Peterson et al. |
| 2021/0008023 A1 | 1/2021 | Lyssikatos et al. |
| 2021/0077493 A1 | 3/2021 | Corson et al. |
| 2021/0220361 A1 | 7/2021 | Fry et al. |

FOREIGN PATENT DOCUMENTS

| | | |
|---|---|---|
| CA | 2700673 | 4/2009 |
| CO | 6960547 | 5/2014 |
| EP | 0988863 | 3/2000 |
| EP | 1971601 | 10/2009 |
| WO | WO 2005/016346 | 2/2005 |
| WO | WO 2005/120504 | 12/2005 |
| WO | WO 2007/059257 | 5/2007 |
| WO | WO 2009/042618 | 4/2009 |
| WO | WO 2009/117277 | 9/2009 |

(Continued)

OTHER PUBLICATIONS

Peterson, Annals of Oncology, vol. 2, Supplements, Sep. 21, 576. (Year: 2017).*
Bang, Annals of Oncology, vol. 28, 855-861, Jan. 2017. (Year: 2017).*
Loibl, Lancet, 2017, vol. 389, 2415-2429. 2016. (Year: 2016).*
U.S. Appl. No. 61/615,082, filed Mar. 23, 2012, Lee et al.
ascopost.com [online], "FDA Grants Breakthrough Therapy Designation to Tucatinib in Combination Therapy for HER2-Positive Breast Cancer", The ASCO Post, Jan. 25, 2020, retrieved on Sep. 14, 2021, retrieved from URL <"https://ascopost.com/issues/january-25-2020/fda-grants-breakthrough-therapy-designation-to-tucatinib-in-combination-therapy-for-her2-positive-breast-cancer/">, 3 pages.

(Continued)

*Primary Examiner* — D Margaret M Seaman

(74) *Attorney, Agent, or Firm* — Fish & Richardson P.C.

(57) ABSTRACT

In one aspect, the present invention provides a method for treating or ameliorating the effects of a HER2 positive cancer in a subject. In some embodiments, the method comprises administering a combination therapy comprising an anti-HER2 antibody and tucatinib. In some embodiments, the method further comprises administering a chemotherapeutic agent (e.g., an antimetabolite) to the subject. Pharmaceutical compositions and kits are also provided herein.

23 Claims, 9 Drawing Sheets

(56) References Cited

FOREIGN PATENT DOCUMENTS

| WO | WO 2013/056108 | 4/2013 |
| WO | WO 2013/056183 | 4/2013 |
| WO | WO 2013/142875 | 9/2013 |
| WO | WO 2016/201370 | 12/2016 |
| WO | WO 2018/201016 | 11/2018 |
| WO | WO 2019/241599 | 12/2019 |
| WO | WO 2020/159822 | 8/2020 |
| WO | WO 2021/080983 | 4/2021 |
| WO | WO 2021/097220 | 5/2021 |
| WO | WO 2021/183529 | 9/2021 |

OTHER PUBLICATIONS

Baselga et al., "Lapatinib with trastuzumab for HER2-positive early breast cancer (NeoALTTO): a randomised, open-label, multicentre, phase 3 trial," Lancet, 2012, 379(9816):633-40.

Baselga et al., "Pertuzumab plus trastuzumab plus docetaxel for metastatic breast cancer," N. Engl. J. Med., 2012, 366(2):109-19.

Blackwell et al., "Overall survival benefit with lapatinib in combination with trastuzumab for patients with human epidermal growth factor receptor 2-positive metastatic breast cancer: final results from the EGF104900 Study," Journal of Clinical Oncology, 2012, 30(21):2585-92.

Blackwell et al., "Randomized study of Lapatinib alone or in combination with trastuzumab in women with ErbB2-positive, trastuzumab-refractory metastatic breast cancer," Journal of Clinical Oncology, 2010, 28(7):1124-30.

Borges et al., "A phase 1b study of ONT-380, an oral HER2-specific inhibitor, combined with ado-trastuzumab emtansine (T-DM1), in HER2+ metastatic breast cancer (MBC).", American Society of Clinical Oncology, Jun. 2, 2014, Full Poster, American Society of Clinical Oncology, Annual Meeting 2014, Poster Board #121A, Abstract ID TPS662, 1 page.

Borges et al., "ONT-380 (ARRY-380)—an Oral HER2 Inhibitor—Final Phase 1 Results and Conclusions", Full Poster, AACR Advances in Breast Cancer Research: Genetics, Biology and Clinical Applications, Oct. 4, 2013, Poster#A050, 9 pages, 1 page.

Borges et al., "Tucatinib Combined with Ado-Trastuzumab Emtansine in Advanced ERBB2/HER2-Positive Metastatic Breast Cancer: A Phase 1 Clinical Trial," Jama Oncology, Sep. 2018, 4(9):124:e1-e7.

Clayton et al., "Incidence of cerebral metastases in patients treated with trastuzumab for metastatic breast cancer," British Journal of Cancer, 2004, 91(4):639-43.

Conlon et al., "Comparative analysis of drug response and gene profiling of HER2-targeted tyrosine kinase inhibitors," British Journal of Cancer, Jan. 2021, 124(7):1249-1259.

Dansey, "Phase III Trial Explores Combination of Tucatinib and T-DM1 in HER2+ Breast Cancer", Targeted Oncology, Oct. 10, 2019, retrieved on Sep. 14, 2021, retrieved from URL<"https://www.targetedonc.com/view/phase-iii-trial-explores-combination-of-tucatinib-and-tdml-in-her2-breast-cancer">, 3 pages.

Dinkel et al., "ARRY-380, a Potent, Small Molecule Inhibitor of ErbB2, Increases Survival in Intracranial ErbB2+ Xenograft Models in Mice", American Association for Cancer Research, Apr. 1, 2012, Abstract and Poster, 3 pages.

Dong et al., "The evolving role of trastuzumab emtansine (T-DM1) in HER2-positive breast cancer with brain metastases," Critical Reviews in Oncology/Hematology, Aug. 2019, 143:20-26.

Duchnowska et al., "Tyrosine Kinase Inhibitors for Brain Metastases in HER2-positive Breast Cancer," Cancer Treatment Reviews, Jun. 2018, 67:71-77.

Ekenel et al., "Capecitabine therapy of central nervous system metastases from breast cancer," Journal of Neurooncology, 2007, 85(2):223-7.

Ema, "Guideline on the investigation of drug interactions," 2012, retrieved from URL <www.ema.europa.eu/docs/en_GB/document_library/Scientific_guideline/2012/07/WC500129606.pdf>, 59 pages.

Fares et al., "Landscape of combination therapy trials in breast cancer brain metastasis," International Journal of Cancer, Feb. 2020, 147(7):1939-1952.

FDA, "Drug Development and Drug Interactions: Table of Substrates, Inhibitors and Inducers," retrieved from URL <www.fda.gov/Drugs/DevelopmentApprovalProcess/DevelopmentResources/DruginteractionsLabeling/ucm093664.htm#potency>, 16 pages.

Ferlay et al., "Cancer incidence and mortality worldwide: sources, methods and major patterns in GLOBOCAN 2012," Int. J. Cancer, 2015, 136(5):E359-E386.

Ferrario et al., "A Phase 1b Study of ONT-380, an Oral HER2-Specific Inhibitor, Combined with Ado-Trastuzumab Emtansine (T-DM1), in HER2+ Metastatic Breast Cancer (MBC)", Full Poster, San Antonio Breast Cancer Symposium, Dec. 11, 2015, Program # P4-14-20, 1 page.

Ferrario et al., "ONT-380 in the treatment of HER2+ breast cancer central nervous system (CNS) metastases (mets).", Journal of Clinical Oncology, May 2015, 33(15): Suppl 15, 1 page.

Foucquier et al., "Analysis of drug combinations: current methodological landscape," Pharmacol. Res. Perspect., 2015, 3(3):e00149, 11 pages.

Friesen et al., "Hydroxypropyl Methylcellulose Acetate Succinate-Based Spray-Dried Dispersions: An Overview", Molecular Pharmaceutics, 2008, 5(8): 1003-1019.

Fults et al., "Sustained-Release of Urease from a Poloxamer Gel Matrix," J. Parenter. Sci. Tech., 1990, 44(2):58-65.

Gatzemeier et al., "Randomized phase II trial of gemcitabine-cisplatin with or without trastuzumab in HER2-positive non-small-cell lung cancer," Annals of Oncology, 2004, 15: 19-27.

Gco.iarc.fr, [online], "Global Cancer Observatory," 2021, retrieved on Apr. 27, 2021, retrieved from URL<globocan.iarc.fr>, 3 pages.

GenBank Accession No. NM_002524.5, "Homo sapiens NRAS proto-oncogene, GTPase (NRAS), mRNA," dated Sep. 10, 2019, 4 pages.

GenBank Accession No. NM_004333.6, "Homo sapiens B-Raf proto-oncogene, serine/threonine kinase (BRAF), transcript variant 1, mRNA," dated Oct. 8, 2019, 7 pages.

GenBank Accession No. NM_004985.5, "Homo sapiens KRAS proto-oncogene, GTPase (KRAS), transcript variant b, mRNA," dated Oct. 9, 2019, 4 pages.

GenBank Accession No. NM_033360.4, "Homo sapiens KRAS proto-oncogene, GTPase (KRAS), transcript variant a, mRNA," dated Oct. 9, 2019, 6 pages.

GenBank Accession No. NP_001276865, "receptor tyrosine-protein kinase erbB-2 isoform c [Homo sapiens]," dated Dec. 4, 2019, 5 pages.

GenBank Accession No. NP_001276866, receptor tyrosine-protein kinase erbB-2 isoform d precursor [Homo sapiens], dated Dec. 28, 2019.

GenBank Accession No. NP_001005862.1, "receptor tyrosine-protein kinase erbB-2 isoform b [Homo sapiens]," dated Oct. 22, 2019, 4 pages.

GenBank Accession No. NP_001276867.1, "receptor tyrosine-protein kinase erbB-2 isoform e [Homo sapiens]," dated Oct. 21, 2019, 3 pages.

GenBank Accession No. NP_001289936.1, "N(G),N(G)-dimethylarginine dimethylaminohydrolase 2 [Homo sapiens]" dated Jun. 26, 2019, 3 pages.

GenBank Accession No. NP_001289937.1, "N(G),N(G)-dimethylarginine dimethylaminohydrolase 2 [Homo sapiens]," dated Jun. 26, 2019, 3 pages.

GenBank Accession No. NP_001289938.1, "arogenate dehydrogenase 1, chloroplastic-like [Glycine max]," dated Oct. 30, 2016, 1 page.

GenBank Accession No. NP_002515.1, "GTPase NRas [Homo sapiens]," dated Sep. 10, 2019, 3 pages.

GenBank Accession No. NP_004324.2, "serine/threonine-protein kinase B-raf isoform 1 [Homo sapiens]," dated Oct. 8, 2019, 5 pages.

GenBank Accession No. NP_004439.2, "receptor tyrosine-protein kinase erbB-2 isoform a precursor [Homo sapiens]," dated Oct. 22, 2019, 6 pages.

GenBank Accession No. NP_004448.2, "long-chain-fatty-acid—CoA ligase 3 [Homo sapiens]," dated Aug. 11, 2019, 3 pages.

(56) References Cited

OTHER PUBLICATIONS

GenBank Accession No. NP_004976.2, "GTPase KRas isoform b [*Homo sapiens*]," dated Oct. 9, 2019, 3 pages.
GenBank Accession No. NP_203524.1, "GTPase KRas isoform a [*Homo sapiens*]", dated Sep. 6, 2015, 3 pages.
Geyer et al., "Lapatinib plus capecitabine for HER2-positive advanced breast cancer," N. Eng. J. Med., 2006, 355(26):2733-43.
Giordano et al., "Systemic therapy for patients with advanced human epidermal growth factor receptor 2-positive breast cancer: American Society of Clinical Oncology clinical practice guideline," J. Clin. Oncology, 2014;32(19):2078-99.
Giri et al., "A novel and alternative approach to controlled release drug delivery system based on solid dispersion technique," Bulletin of Faculty of Pharmacy, Cairo University, 2012, 50:147-159.
GlaxoSmithKline, TYKERB (lapatinib) tablets: Highlights of Prescribing Information, FDA-Approved Patient Label, 2007, 25 pages.
Goldhirsch et al., "2 years versus 1 year of adjuvant trastuzumab for HER2-positive breast cancer (HERA): an open-label, randomised controlled trial," Lancet, 2013, 382(9897):1021-8.
Guidance for Industry, "E14 Clinical Evaluation of QT/QTc Interval Prolongation and Proarrhythmic Potential for Non-Antiarrhythmic Drugs," U.S. Department of Health and Human Services, Food and Drug Administration, Center for Drug Evaluation and Research (CDER), Center for Biologies Evaluation and Research (CBER), Oct. 2005, 20 pages.
Hamilton et al., "A phase 1b study of ONT-380, an oral HER2-specific inhibitor, combined with capecitabine and trastuzumab, in HER2+ metastatic breast cancer (MBC)", American Society of Clinical Oncology, Annual Meeting 2014, Jun. 2, 2014, Poster Board #1218, Abstract ID: TPS663, 1 page.
Hamilton et al., "Efficacy results of a phase 1b study of ONT-380, and oral HER2-specific inhibitor, in combination with capecitabine (C) and trastuzumab (T) in HER2+ metastatic breast cancer (MBC), including patients (pts) with brain metastases (mets)," Cancer Res., 2017, 77(4 Suppl):Abstract No. P4-21-01, 5 pages.
Hamilton et al., "Phase 1b study of ONT-380, an oral HER2-specific inhibitor, in combination with capecitabine (C) and trastuzumab (T) in third line + treatment of HER2+ metastatic breast cancer (MBC)", Full Poster, American Society of Clinical Oncology Annual Meeting, May 30, 2015, Abstract/Poster No. 602, 1 page.
Healio.com [online], "FDA grants priority review to tucatinib for HER2-positive breast cancer", HemOnc Today, Feb. 13, 2020, retrieved on Sep. 14, 2021, retrieved from URL <"https://www.healio.com/news/hematology-oncology/20200213/fda-grants-priority-review-to-tucatinib-for-her2positive-breast-cancer">, 2 pages.
Iacovelli et al., "Incidence and relative risk of grade 3 and 4 diarrhoea in patients treated with capecitabine or 5-fluorouracil: a meta-analysis of published trials," British Journal of Clinical Pharmacology, Jun. 2014, 78(6):1228-1237.
Ijntema et al., "Hydroxyapatite microcamers for biocontrolled release of protein drugs," Int. J. Pharm., 1994, 112(3):215-224.
Isbister et al., "Drug induced QT prolongation: the measurement and assessment of the QT interval in clinical practice," Br. J. Clin. Pharmacol., 2013, 76(1):48-57.
Jacob et al., "Solid state crystallinity, amorphous state, and its implications in the pharmaceutical process", International Journal of Pharameutical Sciences and Research, 2011, 2(3): 472-482.
Johnston et al., "Sustained Delivery of Interleukin-2 from a Poloxamer 407 Gel Matrix Following Intraperitoneal Injection in Mice," Pharm. Res., 1992, 9:425-434.
Koch, "Arry-380: A selective, oral HER2 inhibitor for the treatment of solid tumors," American Association of Cancer Research 102nd Annual Meeting, 2011, 29 pages, http://www.arraybiopharma.com/_documents/Publication/PubAttachment462.pdf.
Krug et al., "Randomized phase II study of weekly docetaxel plus trastuzumab versus weekly paclitaxel plus trastuzumab in patients with previously untreated advanced nonsmall cell lung carcinoma," Cancer, 2004, 104:2149-2155.
Kuyama et al., ""Impact of HER2 Gene and Protein Status on the Treatment Outcome of Cisplatin-Based Chemoradiotherapy for Locally Advanced Non-small Cell Lung Cancer,"" Journal of Thoracic Oncology, May 2008, 3(5):477-482.
Langer, "Polymer-controlled drug delivery systems," Accounts Chem. Res., 1993, 26:537-542.
Lee et al., "In Vivo Activity of ARRY-380, a Potent, Small Molecule Inhibitor of ErbB2 in Combination with Trastuzumab or Docetaxel in BT-474 Human Breast Carcinoma Xenografl Model", Full Poster, American Association for Cancer Research, Apr. 18-22, 2019, Poster#5581, 1 page.
Lee et al., "In Vivo Activity of ARRY-380, a Potent, Small Molecule Inhibitor of ErbB2 in Combination with Trastuzumab, Docetaxel or Bevacizumab", San Antonio Breast Cancer Symposium, Dec. 2009, Poster #510, 1 page.
Lin et al., "CNS metastases in breast cancer," J. Clin. Oncol., 2004, 22(17):3608-17.
Lin et al., "Intracranial Efficacy and Survival With Tucatinib Plus Trastuzumab and Capecitabine for Previously Treated HER2-Positive Breast Cancer with Brain Metastases in the HER2CLIMB Trial", Journal of Clinical Oncology, Aug. 2020, 38(23): 2610-2619.
Lindemann et al., "Amorphous Dispersion Development of ARRY-380, an ErbB2 Selective Inhibitor", American Association of Pharmaceutical Scientists, Annual Meeting and Exposition, Full Poster, Oct. 17, 2012, 1 page.
Lindemann et al., "Solid-State Characterization of Seven Isomorphic Solvates of ARRY-380", Full Poster, American Association of Pharmaceutical Scientists, Annual Meeting and Exposition, Oct. 17, 2012, 1 page.
Lu et al., "Insulin-like growth factor-I receptor signaling and resistance to trastuzumab (Herceptin)," Journal of the National Cancer Institute, 2001, 93(24):1852-7.
Melisko et al., "New challenges and opportunities in the management of brain metastases in patients with ErbB2-positive metastatic breast cancer", Nature Clinical Practice Oncology, 2009, 6(1):25-33.
Meng Sheng, et al., Pharmaceutics, 2012, pp. 252-256, 28 pages (with machine translation).
Morrow et al., "A Phase 1 Study to Assess the Safety, Tolerability and PK of ARRY-380—an Oral Inhibitor of HER2", American Society of Clinical Oncologists, Jun. 2010, Poster#A7, 1 page.
Moulder et al., "Abstract A143: ARRY-380, a selective HER2 inhibitor: From drug design to clinical evaluation," Molecular Cancer Therapeutics, Nov. 2011, 10(11): Supplement, 2 pages.
Moulder et al., "Data from a Completed Phase 1 Study to Assess the Safety, Tolerability and PK of ARRY-380—an Oral Inhibitor of HER2", San Antonio Breast Cancer Symposium, Dec. 10, 2010, Program# P3-14-07, 1 page.
Murray et al., "HER2 Activating Mutations in Estrogen Receptor Positive Breast Cancer," Current Breast Cancer Reports, Apr. 2018, 10(2):41-47.
Murthy et al., "ONT-380 in the Treatment of HER2+ Breast Cancer Central Nervous System (CNS) Metastases", Full Poster, San Antonio Breast Cancer Symposium, Dec. 11, 2015,Program # P4-14-19, 1 page.
Murthy et al., "Tucatinib with capecitabine and trastuzumab in advanced HER2-positive metastatic breast cancer with and without brain metastases: a non-randomised, open-label, phase 1b study," The Lancet, May 2018, 19(7):880-888.
Murthy et al., "Tucatinib, Trastuzumab, and Capecitabine for HER2-Positive Metastatic Breast Cancer", The New England Journal of Medicine, Feb. 2020, 382(7):597-609.
Nahta et al., "HER2 therapy: molecular mechanisms of trastuzumab resistance," Breast Cancer Research, 2006, 8(6):215-1-215-8.
Nielsen et al., "Efficacy of HER2-targeted therapy in metastatic breast cancer: Monoclonal antibodies and tyrosine kinase inhibitors," The Breast, 2013, 22(1):1-12.
Okamoto et al., "PSWC 2004 Symposium Report on Pharmaceutical Field", Pharm Tech Japan, 2004, 20(9):1783-1785.
Owens et al., "HER2 amplification ratios by fluorescence in situ hybridization and correlation with immunohistochemistry in a cohort of 6556 breast cancer tissues," Clinical Breast Cancer, 2004, 5(1):63-9.

(56) References Cited

OTHER PUBLICATIONS

PCT International Preliminary Report on Patentability in International Appln. No. PCT/US2018/029899, dated Apr. 27, 2018, 9 pages.
PCT International Search Report and Written Opinion in International Application No. US2013/033751, dated Jun. 5, 2013, 9 pages.
PCT International Search Report and Written Opinion in PCT Appln. No. PCT/US2018/029899, dated Aug. 6, 2018, 9 pages.
PCT International Search Report in International Application No. PCT/US/2020/014953, dated Apr. 21, 2020, 4 pages.
PCT International Search Report in International Application No. PCT/US2020/056489, dated Mar. 10, 2021, 5 pages.
PCT International Search Report in International Application No. PCT/US2020/060431, dated Mar. 12, 2021, 4 pages.
PCT International Search Report in International Application No. PCT/US2021/021527, dated Jun. 24, 2021, 5 pages.
PCT International Search Report in International Application No. PCT/US2021/034715, dated Aug. 31, 2021, 6 pages.
Pestalozzi et al., "CNS relapses in patients with HER2-positive early breast cancer who have and have not received adjuvant trastuzumab: a retrospective substudy of the HERA trial (BIG 1-01)," The Lancet Oncology, 2013,14(3):244-8.
Peterson et al., "Tucatinib, a HER2 selective kinase inhibitor, is active in patient derived xenograft (PDX) models of HER2-amplified colorectal, esophageal and gastric cancers," Annals of Oncology, Sep. 2017, 28(Supplement 5):v576.
Pheneger et al., "In Vitro and In Vivo Activity of ARRY-380: a Potent, Small Molecule Inhibitor of ErbB2", Full Poster, American Association for Cancer Research, Apr. 18-22, 2009, #1795, 1 page.
Pohlmann et al., "Resistance to Trastuzumab m Breast Cancer," Clin. Cancer Res., 2009, 15(24):7479-91.
Qian et al., "Drug-Polymer Solubility and Miscibility: Stability Consideration and Practical Challenges in Amorphous Solid Dispersion Development", Journal of Pharmaceutical Sciences, Jul. 2010, 99(7): 2941-2947.
Ramakrishna et al., "Recommendations on disease management for patients, with advanced human epidermal growth factor receptor 2-positive breast cancer and brain metastases: American Society of Clinical Oncology clinical practice guideline," J. Clin. Oncol., 2014, 32(19):2100-8.
Scaltriti et al., "Expression of p95HER2, a truncated form of the HER2 receptor, and response to anti-HER2 therapies in breast cancer," Journal of the National Cancer Institute, 2007, 99(8):628-38.
Slamon et al., "Human breast cancer: correlation of relapse and survival with amplification of the HER-2/neu oncogene," Science, 1987, 235(4785):177-82.
Slamon et al., "Use of chemotherapy plus a monoclonal antibody against HER2 for metastatic breast cancerthat overexpresses HER2," N. Eng, J, Med., 2001, 344(11):783-92.
Srinarong et al., "Improved dissolution behavior of lipophilic drugs by solid dispersions: the production process as starting point for formulation considerations," Expert Opin. Drug Deliv., 2011, 8(9):1121-1140.
USCSW Group, "United States Cancer Statistics: 1999-2009 Incidence and Mortality Web-based Report," Atlanta: US Department of Health and Human Services, CfDCaP and National Cancer Institute, 2013, 1 page.
Vasconcelos et al., "Solid dispersions as strategy to improve oral bioavailability of poor water soluble drugs", Drug Discovery Today, Dec. 2007, 12(23-24): 1068-1075.
Verma et al., "Trastuzumab emtansine for HER2-positive advanced breast cancer," N. Eng. J. Med., 2012, 367(19):1783-91.
Vo et al., "Abstract B152: Clinical pharmacokinetics of an improved tablet formulation of ONT-380 in HER2+ metastatic breast cancer patients", Proceedings of the AACR-NCI-EORTC International Conference: Molecular Targets and Cancer Therapeutics, Dec. 2015, 14(12): Supplement 2, 4 pages.
Vogel et al., "Efficacy and safety of trastuzumab as a single agent in first-line treatment of HER2-overexpressing metastatic breast cancer," J. Clin. Oncol., 2002, 20(3):719-26.
Walpole et al. "The weight of nations: an estimation of adult human biomass", BMC Public Health, Jun. 2012, 12:439, 6 pages.
Wang et al., "Targeted therapeutic options and future perspectives for HER2-positive breast cancer", Signal Transduction and Targeted Therapy, 2019, 4:34, 22 pages.
Wong et al., "Mechanisms of resistance to trastuzumab and novel therapeutic strategies in HER2-positive breast cancer," Int. J. Breast Cancer, 2012, Article ID 415170, 13 pages.
Yan et al., "HER2 expression status in diverse cancers: review of results from 37,992 patients," Cancer Metastasis Rev., 2015, 34:157-164.
Zielinski et al., "Optimising the dosage of capecitabine in metastatic breast cancer: confused, clarified or confirmed?", Annals of Oncology, 2010, 21:2145-2152.
ClinicalTrials.gov [online], "NCT03043313: Tucatinib (ONT-380) and Trastuzumab for Patients With HER2-positive Metastatic Colorectal Cancer", Feb. 13, 2017, retrieved on Feb. 1, 2023, retrieved from URL:<https://clinicaltrials.gov/ct2/history/NCT03043313?V_2=View#StudyPageTop>, 6 pages.

* cited by examiner

TREATMENT OF HER2 POSITIVE CANCERS

CROSS-REFERENCE TO RELATED APPLICATIONS

This application is a continuation of U.S. application Ser. No. 16/607,850, filed on Oct. 24, 2019, which is a National Phase Application under 35 U.S.C. § 371 of International Application No. PCT/US2018/029899, filed on Apr. 27, 2018, which claims the benefit of U.S. Provisional Application No. 62/491,872, filed Apr. 28, 2017, the contents of which are hereby incorporated by reference in their entirety.

BACKGROUND OF THE INVENTION

Cancer is a disease that imposes a substantial healthcare burden and significantly affects society in the United States and across the world. In the United States alone, it is estimated that over 1.6 million people were diagnosed with new cases of cancer in 2016, and that about 600,000 people died from cancer. Cancer is an extremely heterogeneous disease, with tumors arising from virtually every cell type in the body, and is associated with a wide range of environmental and genetic risk factors. Furthermore, cancer strikes people of all ages and of all ethnic, cultural, and socioeconomic groups.

Cancers are often the result of mutations that can occur in a large number of genes that play roles in a wide range of cellular processes. In many instances, cancer cells harbor mutations in genes that control processes such as cell growth, division, differentiation, or interaction with the extracellular environment. As an example, mutations that increase the activity of HER2, which is a cell surface receptor that promotes cell growth and division, are implicated in many cancers.

In many cases, tumors are either resistant to a particular cancer therapy, or are initially sensitive to a particular therapy but later become resistant. The development of resistance is often the consequence of mutations that alter the activity of a cell component (e.g., a mutation that renders a signaling molecule constitutively active) or result in the altered expression of a gene (e.g., a mutation that results in the increased expression of a cell signaling receptor such as HER2). In some instances, resistance coincides with or results from the occurrence of mutations that transform a cancer to a more aggressive (e.g., metastatic) form. Metastatic cancers are typically correlated with a worsened prognosis compared to non-metastatic cancers.

The MOUNTAINEER clinical trial (ClinicalTrials.gov Identifier #NCT03043313), is examining the efficacy of a combination of tucatinib and trastuzumab for the treatment of patients with HER2 positive metastatic CRC.

Cancers that are characterized by the overexpression of HER2 (referred to as HER2 positive cancers) are often correlated with poor prognosis or are resistant to many standard therapies. Accordingly, there is a need for new therapies that are effective for the treatment of cancers such as HER2 positive cancers or metastatic HER2 positive cancers. The present invention satisfies this need, and provides other advantages as well.

BRIEF SUMMARY OF THE INVENTION

In some aspects, the present invention provides a method for treating or ameliorating the effects of a HER2 positive cancer in a subject, the method comprising administering an anti-HER2 antibody in combination with tucatinib and a chemotherapeutic agent to thereby treat the HER2 positive cancer. In some embodiments, the cancer is selected from the group consisting of colorectal cancer, esophageal cancer, gastric cancer, cholangiocarcinoma, non-small cell lung cancer, bladder cancer, biliary cancer, breast cancer, and a combination thereof. In some embodiments, the cancer is breast cancer. In some embodiments, the cancer is a metastatic cancer. In some embodiments, the cancer is an unresectable, locally advanced cancer.

In some embodiments, the anti-HER2 antibody is a member selected from the group consisting of trastuzumab, pertuzumab, ado-trastuzumab emtansine, margetuximab, and a combination thereof. In some instances, the anti-HER2 antibody is trastuzumab. In some instances, the anti-HER2 antibody is a combination of trastuzumab and pertuzumab. In some embodiments, the administration of the anti-HER2 antibody is before, during, or after the administration of tucatinib.

In some embodiments, the cancer comprises a cell that has a wild-type KRAS exon 2 genotype. In some embodiments, the cancer comprises a cell that has a wild-type NRAS genotype. In some embodiments, the cancer comprises a cell that has a wild-type BRAF genotype. In yet some embodiments, the subject has a cancer that is refractory to a standard of care which includes cetuximab or panitumumab.

In some embodiments, treating the subject results in a tumor growth inhibition (TGI) index of at least about 85%. In some instances, treating the subject results in a TGI index of about 100%. In some embodiments, the combination of the anti-HER2 antibody and tucatinib is synergistic. In some embodiments, treating the subject results in a TGI index that is greater than the TGI index observed when using an anti-HER2 antibody or tucatinib alone.

In some embodiments, a dose of tucatinib is about 3 to 7 mg per kg of the subject's body weight twice daily. In some embodiments, a dose of tucatinib is about 300 mg twice per day. In some embodiments, a dose of the anti-HER2 antibody is about 6 mg to 8 mg per kg of the subject's body weight once every three weeks. In some embodiments, a dose of the anti-HER2 antibody is about 600 mg once every three weeks. In some embodiments, the tucatinib or the anti-HER2 antibody is administered orally, intravenously, or subcutaneously.

In some embodiments, the method further comprises administering a chemotherapeutic agent (e.g., an antimetabolite, such as capecitabine). In some embodiments, the antimetabolite is a member selected from the group consisting of capecitabine, carmofur, doxidluridine, fluorouracil, tegafur, and a combination thereof. In some embodiments, the antimetabolite is capecitabine. In some embodiments, a dose of capecitabine is about 1,000 mg per m² of the subject's body surface area twice per day. In some embodiments, the chemotherapeutic agent is administered orally. In some embodiments, the capecitabine is administered in 150 mg or 500 mg tablets.

In other aspects, the present invention provides a pharmaceutical composition comprising an anti-HER2 antibody, tucatinib, and a pharmaceutically acceptable carrier. In some embodiments, the anti-HER2 antibody is a member selected from the group consisting of trastuzumab, pertuzumab, ado-trastuzumab emtansine, margetuximab, and a combination thereof. In some instances, the anti-HER2 antibody is trastuzumab. In some instances, the anti-HER2 antibody is a combination of trastuzumab and pertuzumab. In some embodiments, the pharmaceutical composition further comprises a chemotherapeutic agent. In some embodiments, the chemotherapeutic agent is an antimetabolite. In some embodiments, the antimetabolite is capecitabine.

In still other aspects, the present invention provides a kit for treating or ameliorating the effects of a HER2 positive cancer in a subject, the kit comprising a pharmaceutical composition of the present invention. In some embodiments, the kit further comprises instructions for use. In some embodiments, the kit comprises one or more reagents.

Other objects, features, and advantages of the present invention will be apparent to one of skill in the art from the following detailed description and figures.

BRIEF DESCRIPTION OF THE DRAWINGS

FIG. 2A shows the effects of HER2 status on overall survival (OS). FIG. 2B shows the effects of HER2 status on progression-free survival (PFS).

FIG. 3A shows the effects of tucatinib and trastuzumab, alone and in combination, on tumor growth in a CTG-0121 CRC PDX model. FIG. 3B shows the effects of tucatinib and trastuzumab, alone and in combination, on tumor growth in a CTG-0784 CRC PDX model. FIG. 3C shows the effects of tucatinib and trastuzumab, alone and in combination, on tumor growth in a CTG-0383 CRC PDX model.

FIG. 4A shows the effects of tucatinib and trastuzumab, alone and in combination, on tumor growth in a CTG-0137 esophageal cancer PDX model. FIG. 4B shows the effects of tucatinib and trastuzumab, alone and in combination, on tumor growth in a CTG-0138 esophageal cancer PDX model.

FIG. 5A shows the effects of tucatinib and trastuzumab, alone and in combination, on tumor growth in a GXA 3038 gastric cancer PDX model. FIG. 5B shows the effects of tucatinib and trastuzumab, alone and in combination, on tumor growth in a GXA 3039 gastric cancer PDX model. FIG. 5C shows the effects of tucatinib and trastuzumab, alone and in combination, on tumor growth in a GXA 3054 gastric cancer PDX model.

FIG. 7A shows the effects of tucatinib and trastuzumab, alone and in combination, on tumor growth in a Calu-3 NSCLC xenograft model. FIG. 7B shows the effects of tucatinib and trastuzumab, alone and in combination, on tumor growth in an NCI-H2170 NSCLC xenograft model.

DETAILED DESCRIPTION OF THE INVENTION

I. Introduction

Figure 1:
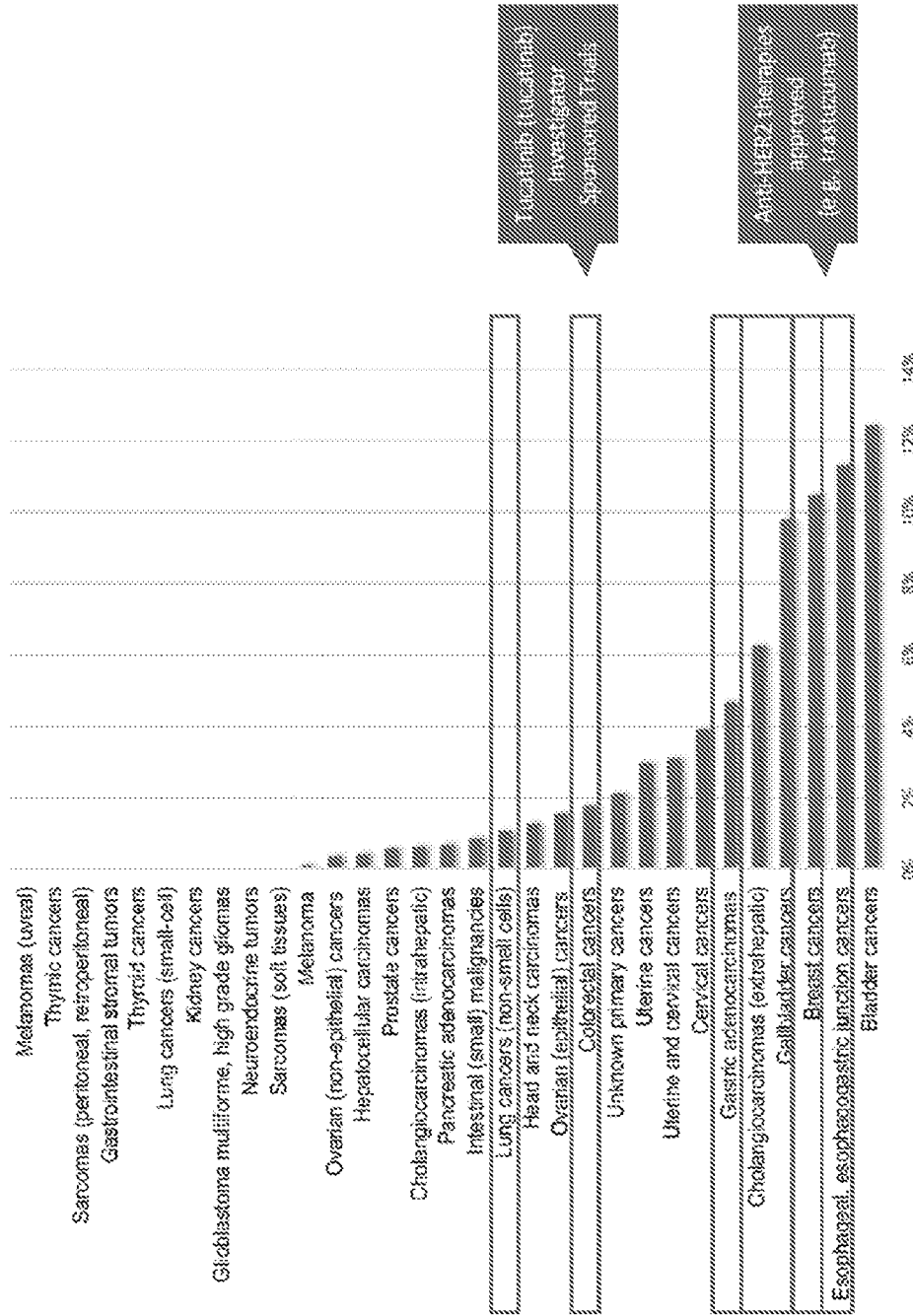
FIG. 1 shows that HER2 amplification occurs across multiple carcinomas (Yan et al. *Cancer Metastasis Rev.* (2015) 34:157-164).

HER2 gene amplification occurs in a number of different carcinomas. For example, FIG. 1 summarizes the prevalence of HER2 positive cancers in a study that analyzed 37,992 samples (Yan et al. *Cancer Metastasis Rev.* (2015) 234:157-164). In this study, samples were analyzed at a central laboratory and tumor HER2 status was determined using immunohistochemistry (IHC). A sample was determined to be HER2 positive if the IHC score was 3+. Several of the cancers represented in FIG. 1 are responsive to tucatinib in investigator-sponsored trials or are approved for treatment with an anti-HER2 therapy.

In colorectal cancer (CRC), with which about 130,000 patients are diagnosed each year, HER2 amplification is found in about 3.5% of the cases overall, and in about 6-10% of the cases in which the tumors have wild-type genotypes for KRAS, NRAS, and BRAF. As a therapeutic approach, targeting HER2 for the treatment of CRC has been validated, for example, by the results of the HERACLES trial, which evaluated the effectiveness of a combination of the anti-HER2 antibody trastuzumab and the tyrosine kinase inhibitor lapatinib. In the HERACLES trial, 914 patients with metastatic CRC (having wild-type KRAS genotypes in exon 2 (codons 12 and 13)) were screened—48 of these patients (5%) had tumors that were HER2 positive. In this study, a 30% objective response rate (ORR) was observed (1 patient with a complete response, and 27 patients with a partial response). Furthermore, 12 out of the 27 patients (44%) had stable disease. All patients had previously been treated with the antibodies cetuximab or panitumumab with a 0% ORR. Furthermore, a combination of the anti-HER2 antibodies trastuzumab and pertuzumab was shown to be active in this patient population. A 38% ORR and 54% clinical benefit rate was observed, with a median time to progression across all patients of 5.6 months.

Among the approximately 16,980 new cases of esophageal cancer that are diagnosed each year (notably, the rate is about 20- to 30-fold higher in China), the incidence of HER2 positive tumors is about 20%. As with CRC, targeting HER2 in gastric and esophageal cancer has been validated as a therapeutic approach. In the TOGA trial, which evaluated the effectiveness of a combination of trastuzumab and cisplatin or fluoropyrimidine in comparison to chemotherapy alone, the combination therapy resulted in an increased overall survival of 2.7 months (13.8 vs. 11.1 months and hazard ratio of 0.74 (95% C.I. 0.60-0.91, p=0.0046)). Furthermore, the GATSBY trial evaluated ado-trastuzumab emtansine (also known as T-DM1) versus taxanes in patients who had exhibited disease progression during or after first-line fluoropyrimidine plus platinum therapy (with or without HER2-targeted agents).

Figure 2A:
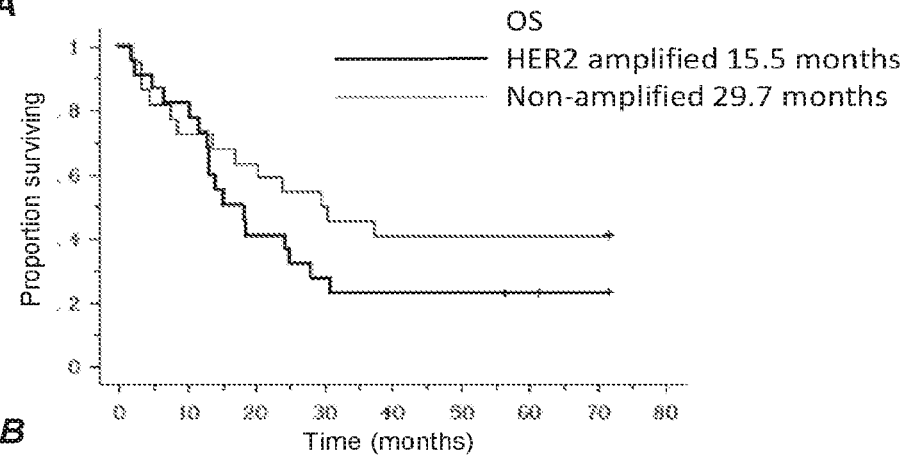
FIGS. 2A and 2B show the relationship between HER2 status and survival in non-small cell lung cancer (NSCLC) (*Journal of Thoracic Oncology.* Vol. 3, Number 5, May 2008).
Figure 2B:
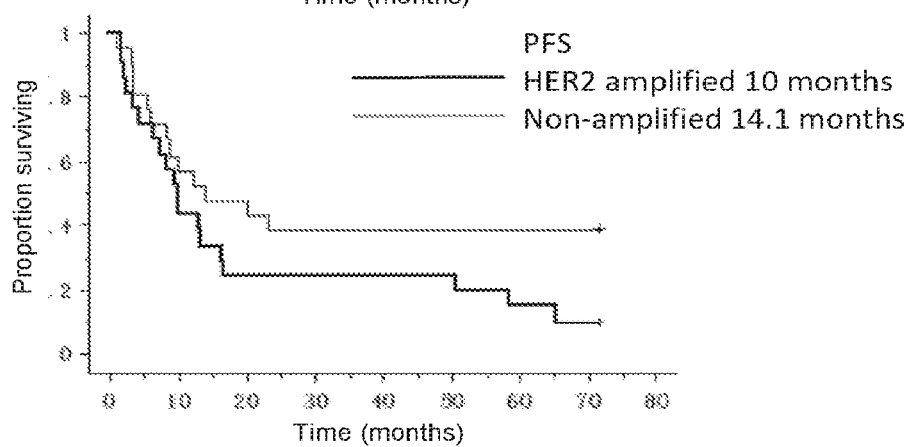

In non-small cell lung cancer (NSCLC), of which about 200,000 new cases were predicted to be diagnosed in 2017, HER2 amplification occurs in approximately 3% of the tumors. A trend of reduced overall survival and progression-free survival has been observed in HER2 positive NSCLC patients treated with standard chemotherapy (FIG. 2), but clinical trials thus far have not focused on HER2 3+/FISH+ patients, and no algorithm is in place for specifically treating HER2 positive NSCLC (*Cancer* (2004) 104:2149-2155; *Annals of Oncology* (2004) 15:19-27). Furthermore, HER2 amplification may serve as an acquired resistance mechanism to epidermal growth factor receptor (EGFR) tyrosine kinase inhibitors (TKIs). Up to 12% of EGFR-mutant NSCLC tumors have HER2 amplification (which occurs independently of the EGFR T790M mutation); this patient population is less likely to respond to a HER2-selective therapy.

The present invention is based, in part, on the observation that a combination of the small molecule TKI tucatinib and the anti-HER2 antibody trastuzumab resulted in tumor regressions in a BT-474 HER2-amplified breast tumor xenograft model, and that HER2 amplification is present in many cancers, as described above. Non-clinical data has been validated by the activity of tucatinib and trastuzumab that was observed in the ONT-380-005 doublet study for the treatment of HER2 positive metastatic breast cancer. The present invention is also based, in part, on the discovery that a combination of tucatinib and trastuzumab was effective for inhibiting tumor growth in several other HER2 positive tumor xenograft models, including CRC, esophageal cancer, gastric cancer, cholangiocarcinoma, and NSCLC.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" as used herein shall generally mean an acceptable degree of error for the quantity measured given the nature or precision of the measurements. Typical, exemplary degrees of error are within 20 percent (%), preferably within 10%, and more preferably within 5% of a given value or range of values. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

Alternatively, in biological systems, the terms "about" and "approximately" may mean values that are within an order of magnitude, preferably within 5-fold, and more preferably within 2-fold of a given value. Numerical quantities given herein are approximate unless stated otherwise, meaning that the term "about" or "approximately" can be inferred when not expressly stated.

When "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9, or 11 mg/kg" is equivalent to "about 7, about 9, or about 11 mg/kg."

The term "or" as used herein should in general be construed non-exclusively. For example, a claim to "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

The group "A or B" is typically equivalent to the group "selected from the group consisting of A and B."

The term "comprising" as used herein should in general be construed as not excluding additional ingredients. For example, a claim to "a composition comprising A" would cover compositions that include A and B; A, B, and C; A, B, C, and D; A, B, C, D, and E; and the like.

The terms "subject," "individual," and "patient" as used herein are used interchangeably herein to refer to a vertebrate, preferably a mammal, more preferably a human. Mammals include, but are not limited to, murines, rats, simians, humans, farm animals, sport animals, and pets. Tissues, cells and their progeny of a biological entity obtained in vivo or cultured in vitro are also encompassed.

As used herein, the term "therapeutically effective amount" includes a dosage sufficient to produce a desired result with respect to the indicated disorder, condition, or mental state. The desired result may comprise a subjective or objective improvement in the recipient of the dosage. For example, an effective amount of a combination of an anti-HER2 antibody and tucatinib includes an amount sufficient to alleviate the signs, symptoms, effects, or causes of cancer (e.g., colorectal cancer, esophageal cancer, gastric cancer, cholangiocarcinoma, non-small cell lung cancer, bladder cancer, or biliary cancer). As another example, an effective amount of a combination of an anti-HER2 antibody and tucatinib includes an amount sufficient to alleviate the signs, symptoms, effects, or causes of metastatic or HER2 positive cancer. As another example, an effective amount of a combination of an anti-HER2 antibody and tucatinib includes an amount sufficient to prevent the development of cancer.

Thus, a therapeutically effective amount can be an amount that slows, reverses, or prevents tumor growth, increases survival time, or inhibits tumor progression or metastasis. Also, for example, an effective amount of an anti-HER2 antibody and tucatinib includes an amount sufficient to cause a substantial improvement in a subject having cancer when administered to the subject. The effective mount can vary with the type and stage of the cancer being treated, the type and concentration of one or more compositions (e.g., comprising an anti-HER2 antibody and tucatinib) administered, and the amounts of other drugs that are also administered.

For the purposes herein, a therapeutically effective amount is determined by such considerations as may be known in the art. The amount must be effective to achieve the desired therapeutic effect in a subject suffering from cancer. The therapeutically effective amount depends, inter alia, on the type and severity of the disease to be treated and the treatment regimen. The therapeutically effective amount is typically determined in appropriately designed clinical trials (e.g., dose range studies) and the person versed in the art will know how to properly conduct such trials in order to determine the therapeutically effective amount. As generally known, a therapeutically effective amount depends on a variety of factors including the distribution profile of a therapeutic agent (e.g., a combination of an anti-HER2 antibody and tucatinib) or composition within the body, the relationship between a variety of pharmacological parameters (e.g., half-life in the body) and undesired side effects, and other factors such as age and sex, etc.

The term "survival" or "survival time" refers to a length of time following the diagnosis of a disease or beginning or completing a particular course of therapy for a disease (e.g., cancer). The term "overall survival" includes the clinical endpoint describing patients who are alive for a defined period of time after being diagnosed with or treated for a disease, such as cancer. The term "disease-free survival" includes the length of time after treatment for a specific disease (e.g., cancer) during which a patient survives with no sign of the disease (e.g., without known recurrence). In certain embodiments, disease-free survival is a clinical parameter used to evaluate the efficacy of a particular therapy, which is usually measured in units of 1 or 5 years. The term "progression-free survival (PFS)" includes the length of time during and after treatment for a specific disease (e.g., cancer) in which a patient is living with the disease without additional symptoms of the disease. In some embodiments, PFS is assessed as central nervous system (CNS) PFS or non-CNS PFS. In some embodiments, survival is expressed as a median or mean value.

As used herein, the term "treating" includes, but is not limited to, methods and manipulations to produce beneficial changes in a recipient's health status (e.g., a patient's cancer status). The changes can be either subjective or objective and can relate to features such as symptoms or signs of the cancer being treated. For example, if the patient notes decreased pain, then successful treatment of pain has occurred. For example, if a decrease in the amount of swelling has occurred, then a beneficial treatment of inflammation has occurred. Similarly, if the clinician notes objective changes, such as reducing the number of cancer cells, the growth of the cancer cells, the size of cancer tumors, or the resistance of the cancer cells to another cancer drug, then treatment of cancer has also been beneficial. Preventing the deterioration of a recipient's status is also included by the term. Treating, as used herein, also includes administering a combination of an anti-HER2 antibody and tucatinib to a patient having cancer (e.g., colorectal cancer, esophageal cancer, gastric cancer, cholangiocarcinoma, non-small cell lung cancer, bladder cancer, or biliary cancer).

The terms "administering" and "administration" include oral administration, topical contact, administration as a suppository, intravenous, intraperitoneal, intramuscular, intralesional, intratumoral, intrathecal, intranasal (e.g., inhalation, nasal mist or drops), or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of a combination of an anti-HER2 antibody and tucatinib according to methods of the present invention for preventing or relieving one or more symptoms associated with cancer.

As used herein, the term "co-administering" includes sequential or simultaneous administration of two or more structurally different compounds. For example, two or more structurally different pharmaceutically active compounds can be co-administered by administering a pharmaceutical composition adapted for oral administration that contains two or more structurally different active pharmaceutically active compounds. As another example, two or more structurally different compounds can be co-administered by administering one compound and then administering the other compound. The two or more structurally different compounds can be comprised of an anti-HER2 antibody and tucatinib. In some instances, the co-administered compounds are administered by the same route. In other instances, the co-administered compounds are administered via different routes. For example, one compound can be administered orally, and the other compound can be administered, e.g., sequentially or simultaneously, via intravenous, intramuscular, subcutaneous, or intraperitoneal injection. The simultaneously or sequentially administered compounds or compositions can be administered such that an anti-HER2 antibody and tucatinib are simultaneously present in a subject or in a cell at an effective concentration.

As used herein, the term "pharmaceutically acceptable carrier" refers to a substance that aids the administration of an active agent to a cell, an organism, or a subject. "Pharmaceutically acceptable carrier" refers to a carrier or excipient that can be included in the compositions of the invention and that causes no significant adverse toxicological effect on the subject. Non-limiting examples of pharmaceutically acceptable carriers include water, NaCl, normal saline solutions, lactated Ringer's, normal sucrose, normal glucose, binders, fillers, disintegrants, lubricants, coatings, sweeteners, flavors and colors, liposomes, dispersion media, microcapsules, cationic lipid carriers, isotonic and absorption delaying agents, and the like. The carrier may also be substances for providing the formulation with stability, sterility and isotonicity (e.g., antimicrobial preservatives, antioxidants, chelating agents and buffers), for preventing the action of microorganisms (e.g. antimicrobial and antifungal agents, such as parabens, chlorobutanol, phenol, sorbic acid and the like) or for providing the formulation with an edible flavor etc. In some instances, the carrier is an agent that facilitates the delivery of a small molecule drug or antibody to a target cell or tissue. One of skill in the art will recognize that other pharmaceutical carriers are useful in the present invention.

As used herein, the term "cancer" is intended to include a member of a class of diseases characterized by the uncontrolled growth of aberrant cells. The term includes cancers of all stages and grades including advanced, recurrent, pre-, and post-metastatic cancers. The term also includes HER2 positive cancers. Drug-resistant and multidrug-resistant cancers are also included. Cancers suitable for treatment according to methods of the present invention include colorectal cancer, gastric cancer, lung cancer (e.g., non-small cell lung cancer (NSCLC)), biliary cancers (e.g., cholangiocarcinoma, gallbladder cancer), bladder cancer, esophageal cancer, melanoma, ovarian cancer, liver cancer, prostate cancer, pancreatic cancer, small intestine cancer, head and neck cancer, uterine cancer, breast cancer, and cervical cancer. In some instances, unknown primary cancers are suitable, particularly if they are HER2 positive. In some embodiments, the cancer has metastasized (e.g., to the brain) As used herein, a "tumor" comprises one or more cancerous cells. Combinations of cancer are not excluded by the term.

In the context of cancer, the term "stage" refers to a classification of the extent of cancer. Factors that are considered when staging a cancer include but are not limited to tumor size, tumor invasion of nearby tissues, and whether the tumor has metastasized to other sites. The specific criteria and parameters for differentiating one stage from another can vary depending on the type of cancer. Cancer staging is used, for example, to assist in determining a prognosis or identifying the most appropriate treatment option(s).

One non-limiting example of a cancer staging system is referred to as the "TNM" system. In the TNM system, "T" refers to the size and extent of the main tumor, "N" refers to the number of nearby lymph nodes to which the cancer has spread, and "M" refers to whether the cancer has metastasized. "TX" denotes that the main tumor cannot be measured, "T0" denotes that the main tumor cannot be found, and "T1," "T2," "T3," and "T4" denote the size or extent of the main tumor, wherein a larger number corresponds to a larger tumor or a tumor that has grown into nearby tissues. "NX" denotes that cancer in nearby lymph nodes cannot be measured, "N0" denotes that there is no cancer in nearby lymph nodes, and "N1," "N2," "N3," and "N4" denote the number and location of lymph nodes to which the cancer has spread, wherein a larger number corresponds to a greater number of lymph nodes containing the cancer. "MX" denotes that metastasis cannot be measured, "M0" denotes that no metastasis has occurred, and "M1" denotes that the cancer has metastasized to other parts of the body.

As another non-limiting example of a cancer staging system, cancers are classified or graded as having one of five stages: "Stage 0," "Stage I," "Stage II," "Stage III," or "Stage IV." Stage 0 denotes that abnormal cells are present, but have not spread to nearby tissue. This is also commonly called carcinoma in situ (CIS). CIS is not cancer, but may subsequently develop into cancer. Stages I, II, and III denote that cancer is present. Higher numbers correspond to larger tumor sizes or tumors that have spread to nearby tissues. Stage IV denotes that the cancer has metastasized. One of skill in the art will be familiar with the different cancer staging systems and readily be able to apply or interpret them.

The term "HER2" (also known as also known as HER2/neu, ERBB2, CD340, receptor tyrosine-protein kinase erbB-2, proto-oncogene Neu, and human epidermal growth factor receptor 2) refers to a member of the human epidermal growth factor receptor (HER/EGFR/ERBB) family of receptor tyrosine kinases. Amplification or overexpression of HER2 plays a significant role in the development and progression of certain aggressive types of cancer, including colorectal cancer, gastric cancer, lung cancer (e.g., non-small cell lung cancer (NSCLC)), biliary cancers (e.g., cholangiocarcinoma, gallbladder cancer), bladder cancer, esophageal cancer, melanoma, ovarian cancer, liver cancer, prostate cancer, pancreatic cancer, small intestine cancer, head and neck cancer, uterine cancer, cervical cancer, and breast cancer. Non-limiting examples of HER2 nucleotide sequences are set forth in GenBank reference numbers NP_001005862, NP_001289936, NP_001289937, NP_001289938, and NP_004448. Non-limiting examples of HER2 peptide sequences are set forth in GenBank reference numbers NP_001005862, NP_001276865, NP_001276866, NP_001276867, and NP_004439.

When HER2 is amplified or overexpressed in or on a cell, the cell is referred to as being "HER2 positive." The level of HER2 amplification or overexpression in HER2 positive cells is commonly expressed as a score ranging from 0 to 3 (i.e., HER2 0, HER2 1+, HER2 2+, or HER2 3+), with higher scores corresponding to greater degrees of expression.

The term "tucatinib," also known as ONT-380 and ARRY-380, refers to the small molecule tyrosine kinase inhibitor that suppresses or blocks HER2 activation. Tucatinib has the following structure:

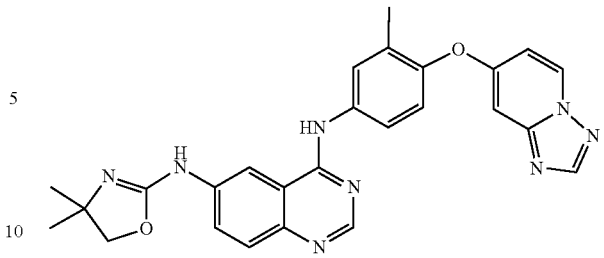

The term "anti-HER2 antibody" refers to an antibody that binds to the HER2 protein. Anti-HER2 antibodies used for the treatment of cancer are typically monoclonal, although polyclonal antibodies are not excluded by the term. Anti-HER2 antibodies inhibit HER2 activation or downstream signaling by various mechanisms. As non-limiting examples, anti-HER2 antibodies can prevent ligand binding, receptor activation or receptor signal propagation, result in reduced HER2 expression or localization to the cell surface, inhibit HER2 cleavage, or induce antibody-mediated cytotoxicity. Non-limiting examples of anti-HER2 antibodies that are suitable for use in the methods and compositions of the present invention include trastuzumab, pertuzumab, ado-trastuzumab emtansine (also known as T-DM1), margetuximab, and combinations thereof.

The term "chemotherapeutic agent" refers to a group of compounds useful in treating or ameliorating cancer or its symptoms. In some embodiments, chemotherapeutic agents include alkylating antineoplastic agents (e.g., nitrogen mustards, such as mechlorathamine, isfosfamide, melphalan, chlorambucil, and cyclophosphamide; alkyl sufonates, such as busulfan; nitrosoureas, such as streptozocin, carmustine, and lomustine; triazines, such as dacarbazine and temozolomide; and ethyleneimines, such as thiotepa and altretamine), antimetabolites (see below), antitumor antibiotics (e.g., the anthracyclins, such as daunorubicin, doxorubicin, epirubicin, idarubicin, and valrubicin; the bleomycins; mitomycin C, mitoxantrone, and actinomycin), aromatase inhibitors (e.g., steroidal inhibitors, such as exemestane; and non-steroidal inhibitors, such as anastrozole and letrozole), kinase inhibitors (e.g., tyrosine kinase inhibitors, such as imatinib, gefitinib, erlotinib, lapatinib, nilotinib, sunitibnib, and sorafenib; and, e.g., bosunitinib, neratinib, vatalanib, and toceranib), mTor inhibitors (e.g., rapamycin and its analogs, such as temsirolimus, everolimus, and ridaforolimus; dual PIcK/mTOR inhibitors; and ATP-competitive mTOR inhibitors, such as sapanisertib), retinoids (e.g., tretinoin, alitretinoin, bexarotene, and isotretinoin), topoisomerase inhibitors (e.g., doxorubicin, etoposide, teniposide, mitoxantrone, novobiocin, merbaron, aclatubicin, camptothecin, and camptothecin prodrugs or derivatives, such as irinotecan and topothecan), and plant alkaloids (e.g., the *Vinca* alkaloids vinblastine, vinorelbine, vincristine, and vindesine; the taxanes, such as docetaxel and paclitaxel).

The term "antimetabolite" refers to a group of compounds useful in treating cancer. Antimetabolites typically are similar in structure to a compound in ordinary metabolism, such as folic acid, a purine, or a pyrimidine, which allows them to interfere with metabolic processes incorporating the structurally similar compound. For example, the antimetabolite 5-fluorouracil ("fluorouracil") interferes with metabolic pathways that incorporate the compound uracil. In some embodiments, the antimetabolites include pyrimidine antagonists, such as capecitabine, cytarabine, decitabine, fluorouracil, and gemcitabine; purine antagonists, such as fludarabine and 6-mercaptopurine; and folate antagonists, such as methotrexate and permetrexed. In some embodiments, the antimetabolites include carmofur, cytarabine, doxifluridine, floxuridine, fluorouracil, fludarabine, gemcitabine, hydroxycarbamide, 6-mercaptopurine, methotrexate, permetrexed, and tegafur. In some embodiments, the antimetabolites (e.g., the fluoropyrimidines) include capecitabine, carmofur, doxifluridine, fluorouracil, and tegafur (preferably, capecitabine).

The term "capecitabine" refers to a prodrug of fluorouracil having the following structure:

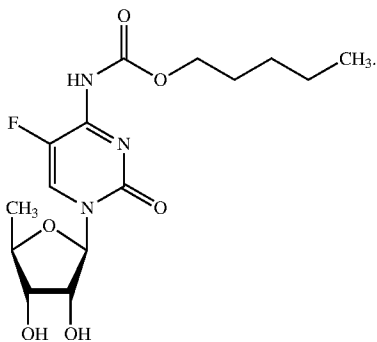

Capecitabine undergoes hydrolysis in the liver and tissues to form fluorouracil which is the active moiety. Fluorouracil is a fluorinated pyrimidine antimetabolite that inhibits thymidylate synthetase, blocking the methylation of deoxyuridylic acid to thymidylic acid, interfering with DNA, and to a lesser degree, RNA synthesis.

The term "tumor growth inhibition (TGI) index" refers to a value used to represent the degree to which an agent (e.g., tucatinib, an anti-HER2 antibody, or a combination thereof) inhibits the growth of a tumor when compared to an untreated control. The TGI index is calculated for a particular time point (e.g., a specific number of days into an experiment or clinical trial) according to the following formula:

$$TGI = 1 - \left( \frac{Volume_{treated(Tx\ Day\ X)} - Volume_{treated(Tx\ Day\ 0)}}{Volume_{control(Tx\ Day\ X)} - Volume_{control(Tx\ Day\ 0)}} \right) \times 100\%,$$

where "Tx Day 0" denotes the first day that treatment is administered (i.e., the first day that an experimental therapy or a control therapy (e.g., vehicle only) is administered) and "Tx Day X" denotes X number of days after Day 0. Typically, mean volumes for treated and control groups are used. As a non-limiting example, in an experiment where study day 0 corresponds to "Tx Day 0" and the TGI index is calculated on study day 28 (i.e., "Tx Day 28"), if the mean tumor volume in both groups on study day 0 is 250 mm$^3$ and the mean tumor volumes in the experimental and control groups are 125 mm$^3$ and 750 mm$^3$, respectively, then the TGI index on day 28 is 125%.

As used herein, the term "synergistic" or "synergy" refers to a result that is observed when administering a combination of components or agents (e.g., a combination of tucatinib and an anti-HER2 antibody) produces an effect (e.g., inhibition of tumor growth, prolongation of survival time) that is greater than the effect that would be expected based on the additive properties or effects of the individual components. In some embodiments, synergism is determined by performing a Bliss analysis (see, e.g., Foucquier et al. *Pharmacol. Res. Perspect.* (2015) 3(3):e00149; hereby incorporated by reference in its entirety for all purposes). The Bliss Independence model assumes that drug effects are outcomes of probabilistic processes, and assumes that the drugs act completely independently (i.e., the drugs do not interfere with one another (e.g., the drugs have different sites of action) but each contributes to a common result). According to the Bliss Independence model, the predicted effect of a combination of two drugs is calculated using the formula:

$$E_{AB} = E_A + E_B - E_A \times E_B,$$

where $E_A$ and $E_B$ represent the effects of drugs A and B, respectively, and $E_A$ represents the effect of a combination of drugs A and B. When the observed effect of the combination is greater than the predicted effect $E_{AB}$, then the combination of the two drugs is considered to be synergistic. When the observed effect of the combination is equal to $E_{AB}$, then the effect of the combination of the two drugs is considered to be additive. Alternatively, when the observed effect of the combination is less than $E_{AB}$, then the combination of the two drugs is considered to be antagonistic.

The observed effect of a combination of drugs can be based on, for example, the TGI index, tumor size (e.g., volume, mass), an absolute change in tumor size (e.g., volume, mass) between two or more time points (e.g., between the first day a treatment is adminstered and a particular number of days after treatment is first administered), the rate of change of tumor size (e.g., volume, mass) between two or more time points (e.g., between the first day a treatment is adminstered and a particular number of days after treatment is first administered), or the survival time of a subject or a population of subjects. When the TGI index is taken as a measure of the observed effect of a combination of drugs, the TGI index can be determined at one or more time points. When the TGI index is determined at two or more time points, in some instances the mean or median value of the multiple TGI indices can be used as a measure of the observed effect. Furthermore, the TGI index can be determined in a single subject or a population of subjects. When the TGI index is determined in a population, the mean or median TGI index in the population (e.g., at one or more time points) can be used as a measure of the observed effect. When tumor size or the rate of tumor growth is used as a measure of the observed effect, the tumor size or rate of tumor growth can be measured in a subject or a population of subjects. In some instances, the mean or median tumor size or rate of tumor growth is determined for a subject at two or more time points, or among a population of subjects at one or more time points. When survival time is measured in a population, the mean or median survival time can be used as a measure of the observed effect.

The predicted combination effect $E_{AB}$ can be calculated using either a single dose or multiple doses of the drugs that make up the combination (e.g., tucatinib and an anti-HER2 antibody). In some embodiments, the predicted combination effect $E_{AB}$ is calculated using only a single dose of each drug A and B (e.g., tucatinib and an anti-HER2 antibody), and the values $E_A$ and $E_B$ are based on the observed effect of each drug when administered as a single agent. When the values for $E_A$ and $E_B$ are based on the observed effects of administering drugs A and B as single agents, $E_A$ and $E_B$ can be based on, for example, TGI indices, tumor sizes (e.g., volume, mass) measured at one or more time points, absolute changes in tumor size (e.g., volume, mass) between two or more time points (e.g., between the first day a treatment is adminstered and a particular number of days after treatment is first administered), the rates of change of tumor sizes (e.g., volume, mass) between two or more time points (e.g., between the first day a treatment is adminstered and a particular number of days after treatment is first administered), or the survival time of a subject or a population of subjects in each treatment group.

When TGI indices are taken as a measure of the observed effects, the TGI indices can be determined at one or more time points. When TGI indices are determined at two or more time points, in some instances the mean or median values can be used as measures of the observed effects. Furthermore, the TGI indices can be determined in a single subject or a population of subjects in each treatment group. When the TGI indices are determined in populations of subjects, the mean or median TGI indices in each population (e.g., at one or more time points) can be used as measures of the observed effects. When tumor sizes or the rates of tumor growth are used as measures of the observed effects, the tumor sizes or rates of tumor growth can be measured in a subject or a population of subjects in each treatment group. In some instances, the mean or median tumor sizes or rates of tumor growth are determined for subjects at two or more time points, or among populations of subjects at one or more time points. When survival time is measured in a population, mean or median survival times can be used as measures of the observed effects.

In some embodiments, the predicted combination effect $E_{AB}$ is calculated using a range of doses (i.e., the effects of each drug, when administered as a single agent, are observed at multiple doses and the observed effects at the multiple doses are used to determine the predicted combination effect at a specific dose). As a non-limiting example, $E_{AB}$ can be calculated using values for $E_A$ and $E_B$ that are calculated according to the following formulae:

$$E_A = E_{Amax} \times \frac{a^p}{A_{50}^p + a^p}$$

$$E_B = E_{Bmax} \times \frac{b^q}{B_{50}^q + bq},$$

where $E_{Amax}$ and $E_{Bmax}$ are the maximum effects of drugs A and B, respectively, $A_{50}$ and $B_{50}$ are the half maximum effective doses of drugs A and B, respectively, a and b are administered doses of drugs A and B, respectively, and p and q are coefficients that are derived from the shapes of the dose-response curves for drugs A and B, respectively (see, e.g., Foucquier et al. *Pharmacol. Res. Perspect.* (2015) 3(3):e00149).

In some embodiments, a combination of two or more drugs is considered to be synergistic when the combination produces an observed TGI index that is greater than the predicted TGI index for the combination of drugs (e.g., when the predicted TGI index is based upon the assumption that the drugs produced a combined effect that is additive). In some instances, the combination is considered to be synergistic when the observed TGI index is at least about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, or 80% greater than the predicted TGI index for the combination of drugs.

In some embodiments, the rate of tumor growth (e.g., the rate of change of the size (e.g., volume, mass) of the tumor) is used to determine whether a combination of drugs is synergistic (e.g., the combination of drugs is synergistic when the rate of tumor growth is slower than would be expected if the combination of drugs produced an additive effect). In some embodiments, survival time is used to determine whether a combination of drugs is synergistic (e.g., a combination of drugs is synergistic when the survival time of a subject or population of subjects is longer than would be expected if the combination of drugs produced an additive effect).

The term "KRAS" refers to the gene that encodes the KRAS GTPase. The KRAS gene is also known as V-Ki-ras2 Kirsten rat sarcoma viral oncogene homolog, K-Ras, C-Ki-RAS, K-Ras2, KRAS2, and transforming protein p21. In humans, KRAS is located on chromosome 12 and contains four coding exons and a 5' non-coding exon. KRAS is a member of the Ras subfamily of GTPases and is primarily involved with regulating cell growth and division. In particular, KRAS relays signals from the cell surface (e.g., from activated HER2 receptors) to the cell nucleus via the RAS/MAPK pathway. Mutations in KRAS, particularly activating mutations (e.g., mutations resulting in a constitutively active GTP-bound state and activation of downstream proliferative signaling pathways), have been identified and are correlated with a poor response to anti-HER2 therapies in some instances. Mutations in KRAS are found in about 35%-45% of CRCs in humans, and in particular codons 12 and 13 (found within exon 2) are mutation hotspots, with about 95% of the KRAS mutations being located in one of these two codons. Common KRAS mutations found in CRCs include G12D, G12A, G12R, G12C, G12S, G12V, and G13D. Non-limiting examples of KRAS mRNA sequences are set forth in GenBank reference numbers NM_004985→NP_004976 and NM_033360→NP_203524.

The term "NRAS" refers to the gene that encodes the NRAS GTPase. The NRAS gene is also known as neuroblastoma Ras viral oncogene homolog, N-Ras, NRASI, CMNS, and ALPS4. In humans, KRAS is located on chromosome 1 and contains seven exons. NRAS is a member of the Ras subfamily of GTPases and is involved with regulating cell growth and division. In particular, NRAS relays signals from the cell surface (e.g., from activated HER2 receptors) to the cell nucleus via the RAS/MAPK pathway. NRAS activating mutations (e.g., mutations resulting in a constitutively active GTP-bound state and activation of downstream proliferative signaling pathways) are correlated with a poor response to anti-HER2 therapies in some instances. Mutations that have been identified in colorectal cancers include I263T, S310F, A466T, R678Q, L755S, V777L, V842I, R868W, and N1219S. A non-limiting example of an NRAS mRNA sequence is set forth in GenBank reference number NM_002524→NP_002515.

The term "BRAF" refers to the gene that encodes the B-Raf serine/threonine kinase. The BRAF gene is also known as proto-oncogene B-Raf, v-Raf murine sarcoma viral oncogene homolog B, B-RAF1, BRAF1, NS7, B-Raf, and RAFB1. In humans, BRAF is located on chromosome 7. B-Raf is a member of the Raf family of kinases and is involved in regulating cell growth and division. In particular, B-Raf relays signals from the cell surface (e.g., from activated HER2 receptors) to the cell nucleus via the RAS/MAPK pathway. Mutations in BRAF are implicated in the development of certain cancers and, in some instances, are associated with poor response to anti-HER2 therapies. V600E BRAF mutations have been identified in colorectal cancer. Additional BRAF mutations that have been identified include R4611, 1462S, G463E, G463V, G465A, G465E, G465V, G468A, G468E, N580S, E585K, D593V, F594L, G595R, L596V, T5981, V599D, V599E, V599K, V599R, V600K, and A727V. A non-limiting example of an NRAS mRNA sequence is set forth in GenBank reference number NM_004333→NP_004324.

III. Description of the Embodiments

A. Methods for Treating and Ameliorating Cancer

In one aspect, the present invention provides a method for treating or ameliorating the effects of cancer (e.g., colorectal cancer, esophageal cancer, gastric cancer, cholangiocarcinoma, non-small cell lung cancer, bladder cancer, biliary cancer, breast cancer, or a combination thereof) in a subject, the method comprising administering to the subject an anti-HER2 antibody in combination with tucatinib. In some preferred embodiments, the method further comprises administering a chemotherapeutic agent (e.g., an antimetabolite, such as capecitabine). In some preferred embodiments, the cancer is a HER2 positive (e.g., HER2 1+, 2+, or 3+) cancer. In some embodiments, the cancer is a metastatic cancer. In some instances, the cancer is a HER2 positive metastatic cancer. In some embodiments, the cancer is an unresectable, locally advanced cancer.

Anti-HER2 antibodies suitable for the treatment or amelioration of cancer according to methods of the present invention include, but are not limited to, trastuzumab, pertuzumab, ado-trastuzumab emtansine, margetuximab, and a combination thereof. In some embodiments, the anti-HER2 antibody comprises trastuzumab. In some embodiments, the anti-HER2 antibody comprises a combination of trastuzumab and pertuzumab.

Methods of the present invention are suitable for preventing or treating any number of cancers, including various solid tumors, particularly HER2 positive metastatic cancers. In some embodiments, the type of cancer that is treated or ameliorated is selected from the group consisting of colorectal cancer, gastric cancer, lung cancer (e.g., non-small cell lung cancer (NSCLC)), biliary cancers (e.g., cholangiocarcinoma, gallbladder cancer), bladder cancer, esophageal cancer, melanoma, ovarian cancer, liver cancer, prostate cancer, pancreatic cancer, small intestine cancer, head and neck cancer, uterine cancer, breast cancer, and cervical cancer. In some instances, the methods are suitable for treating HER2 positive cancers of unknown primary type. In some embodiments, the cancer that is treated or ameliorated is selected from the group consisting of colorectal cancer, esophageal cancer, gastric cancer, cholangiocarcinoma, non-small cell lung cancer, bladder cancer, breast cancer, and biliary cancer. In some preferred embodiments, the cancer is breast cancer.

In some embodiments, the cancer is an advanced cancer. In some embodiments, the cancer is a drug-resistant cancer (e.g., the cancer is resistant to cetuximab or panitumumab). In some instances, the cancer is a multidrug-resistant cancer. In some embodiments, the subject has a cancer that is relapsed, refractory, or resistant to one or more drugs or therapies that are the standard of care for the cancer being treated. In some instances, the subject has a cancer that is relapsed, refractory, or resistant to a standard of care that comprises cetuximab or panitumumab. In some embodiments, the patient has previously been treated with a fluoropyrimidine (e.g., 5-fluorouracil, capecitabine), oxalaplatin, irinotecan, or an anti-VEGF antibody (e.g., bevacizumab, ramucirumab, ziv-aflibercept), or such a treatment is contraindicated in the subject.

In some embodiments, a dose of tucatinib is between about 0.1 mg and 10 mg per kg of the subject's body weight (e.g., about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 mg per kg of the subject's body weight). In some embodiments, a dose of tucatinib is between about 2 to 8 mg per kg of the subject's body weight (e.g., about 3 to 7; about 4 to 7; about 2.5 to 6; about 2, 2.5, 3, 3.5, 4, 4.5, 5, 5.5, 6, 6.5, 7, 7.5, or 8). In some embodiments, a dose of tucatinib is between about 10 mg and 100 mg per kg of the subject's body weight (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 mg per kg of the subject's body weight). In particular embodiments, a dose of tucatinib is between about 1 mg and 50 mg per kg of the subject's body weight (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg per kg of the subject's body weight). In some instances, a dose of tucatinib is about 50 mg per kg of the subject's body weight.

In some embodiments, a dose of tucatinib comprises between about 1 mg and 100 mg (e.g. about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 mg) of tucatinib. In some embodiments, a dose of tucatinib comprises between about 100 mg and 1,000 mg (e.g., about 100, 105, 110, 115, 120, 125, 130, 135, 140, 145, 150, 155, 160, 165, 170, 175, 180, 185, 190, 195, 200, 205, 210, 215, 220, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1,000 mg) of tucatinib. In some embodiments, a dose of tucatinib is about 150, 200, 250, 300, 350, 400, 450, or 500 mg (e.g., when administered twice per day). In particular embodiments, a dose of tucatinib is about 300 mg (e.g., when administered twice per day).

In some embodiments, a dose of tucatinib comprises at least about 1,000 mg to 10,000 mg (e.g., at least about 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000 or more mg) of tucatinib.

In some embodiments, a dose of tucatinib contains a therapeutically effective amount of tucatinib. In some embodiments, a dose of tucatinib contains less than a therapeutically effective amount of tucatinib (e.g., when multiple doses are given in order to achieve the desired clinical or therapeutic effect).

In some embodiments, a dose of the anti-HER2 antibody is between about 0.1 mg and 10 mg per kg of the subject's body weight (e.g., about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 mg per kg of the subject's body weight). In some embodiments, a dose of the anti-HER2 antibody is between about 10 mg and 100 mg per kg of the subject's body weight (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 mg per kg of the subject's body weight). In some embodiments, a dose of the anti-HER2 antibody is at least about 100 mg to 500 mg per kg of the subject's body weight (e.g., at least about 100, 125, 150, 175, 200, 225, 250, 275, 300, 325, 350, 375, 400, 425, 450, 475, 500, or more mg per kg of the subject's body weight). In some instances, a dose of the anti-HER2 antibody is about 6 mg per kg of the subject's body weight. In other instances, a dose of the anti-HER2 antibody is about 8 mg per kg of the subject's body weight. In some instances, a dose of the anti-HER2 antibody is about 2 mg per kg of the subject's body weight. In some other instances, a dose of the anti-HER2 antibody is about 20 mg per kg of the subject's body weight. In some embodiments, an initial loading dose of 8 mg/kg is administered, and then subsequent doses of 6 mg/kg are administered.

In some embodiments, a dose of the anti-HER2 antibody comprises between about 1 mg and 100 mg (e.g. about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 mg) of the anti-HER2 antibody. In some embodiments, a dose of the anti-HER2 antibody comprises between about 100 mg and 1,000 mg (e.g., about 100, 105, 110, 115, 120, 125, 130, 135, 140, 145, 150, 155, 160, 165, 170, 175, 180, 185, 190, 195, 200, 205, 210, 215, 220, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1,000 mg) of the anti-HER2 antibody.

In particular embodiments, a dose of the anti-HER2 antibody comprises between about 100 mg and 400 mg (e.g., about 100, 125, 150, 175, 200, 225, 250, 275, 300, 325, 350, 375, or 400 mg) of the anti-HER2 antibody. As a non-limiting example, when using a dose of 6 mg/kg, a dose for a 50 kg subject is about 300 mg. As another non-limiting example, when using a dose of 8 mg/kg, a dose for a 50 kg subject is about 400 mg.

In some embodiments, a dose of the anti-HER2 antibody comprises at least about 1,000 mg to 10,000 mg (e.g., at least about 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000 or more mg) of the anti-HER2 antibody.

In some embodiments, a dose of the anti-HER2 antibody contains a therapeutically effective amount of the anti-HER2 antibody. In some embodiments, a dose of the anti-HER2 antibody contains less than a therapeutically effective amount of the anti-HER2 antibody (e.g., when multiple doses are given in order to achieve the desired clinical or therapeutic effect).

In some embodiments, a dose of the antimetabolite (e.g., capecitabine) is between about 100 mg and 2,000 mg per mm$^2$ of the subject's body surface area (e.g., about 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,550, 1,600, 1,650, 1,700, 1,750, 1,800, 1,850, 1,900, 1,950, or 2,000 mg per mm$^2$ of the subject's body surface area). In some instances, a dose of antimetabolite is about 1,000 mg per mm$^2$ of the subject's body surface area. In some instances, a dose of antimetabolite is about 1,250 mg per mm$^2$ of the subject's body surface area In some embodiments, a dose of antimetabolite (e.g., capecitabine) comprises between about 100 mg and 4.000 mg (e.g. about 100, 150, 200, 250, 300, 350, 400, 450, 500, 550, 600, 650, 700, 750, 800, 850, 900, 950, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, or 4,000 mg) of capecitabine. In some embodiments, a dose of antimetabolite is about 150, 300, 450, 500, 600, 650, 750, 800, 900, 950, 1000, or 1100 mg. In some embodiments, a dose of capecitabine is in 150 or 500 mg tablets.

In some embodiments, a dose of antimetabolite (e.g., capecitabine) contains a therapeutically effective amount of the antimetabolite. In some embodiments, a dose of the antimetabolite contains less than a therapeutically effective amount of the antimetabolite (e.g., when multiple doses are given in order to achieve the desired clinical or therapeutic effect).

The data obtained from, for example, animal studies (e.g., rodents and monkeys) can be used to formulate a dosage range for use in humans. The dosage of compounds of the present invention lies preferably within a range of circulating concentrations that include the ED$_{50}$ with little or no toxicity. The dosage can vary within this range depending upon the dosage form employed and the route of administration. For any composition (e.g., comprising a combination of tucatinib, an anti-HER2 antibody, or capecitabine) for use in the methods of the invention, the therapeutically effective dose can be estimated initially from cell culture assays. A dose can be formulated in animal models to achieve a circulating plasma concentration range that includes the IC$_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC).

It is furthermore understood that appropriate doses of a composition (e.g., comprising a combination of tucatinib, an anti-HER2 antibody, or capecitabine) depend upon the potency of the composition with respect to the desired effect to be achieved. When one or more of these compositions is to be administered to a mammal, a physician, veterinarian, or researcher may, for example, prescribe a relatively low dose at first, subsequently increasing the dose until an appropriate response is obtained. In addition, it is understood that the specific dose level for any particular mammal subject depends upon a variety of factors including the activity of the specific composition employed; the age, body weight, general health, sex, and diet of the subject; the time of administration; the route of administration; the rate and mode of excretion; effects of any drug combinations; and the degree of expression or activity to be modulated.

In certain embodiments, a combination of tucatinib, an anti-HER antibody, or the antimetabolite (e.g., capecitabine) is administered to the subject. When tucatinib, the anti-HER2 antibody, or the antimetabolite are co-administered to the subject, tucatinib, the anti-HER2 antibody, or the antimetabolite can either be administered simultaneously or sequentially. In some embodiments, the anti-HER2 antibody or the antimetabolite is administered during the administration of tucatinib. In some embodiments, the anti-HER2 antibody or the antimetabolite is administered before the administration of tucatinib. In some embodiments, the anti-HER2 antibody or the antimetabolite is administered after the administration of tucatinib. Tucatinib and capecitabine can be administered together or sequentially (e.g., tucatinib can be administered before or after capecitabine).

In some embodiments, tucatinib and the anti-HER2 antibody or the antimetabolite are administered at the same time. In some embodiments, tucatinib and the anti-HER2 antibody or the antimetabolite are not administered at the same time but are administered the same number of times per day, or the same number of times per week, or the same number of times per month (e.g., all are administered once per day, twice per day, once per week, twice per week, and so on). In some embodiments, tucatinib, the anti-HER2 antibody, or the antimetabolite are given on different dosing schedules. As a non-limiting example, tucatinib is administered once per day, and the anti-HER2 antibody is administered twice per day, or vice versa. As another non-limiting example, tucatinib is administered once per day, and the anti-HER2 antibody is administered once every 2, 3, 4, 5, 6, or more days, or vice versa. The skilled artisan will also appreciate that certain factors may influence the dosage and timing required to effectively treat a subject, including but not limited to the severity of the disease or malignant condition, previous treatments, the general health or age of the subject, and other diseases present. Moreover, treatment of a subject with a therapeutically effective amount of a composition (e.g., comprising a combination of tucatinib and an anti-HER2 antibody) can include a single treatment or, preferably, can include a series of treatments.

Optimum dosages, toxicity, and therapeutic efficacy of the compositions (e.g., comprising a combination of tucatinib and an anti-HER2 antibody) administered according to the methods of the present invention may vary depending on the relative potency of the administered composition and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care is taken to design a delivery system that targets such agents to the site of affected tissue to minimize potential damage to normal cells and, thereby, reduce side effects.

Optimal dosing schedules can be calculated from measurements of active ingredient accumulation in the body of a subject. In general, dosage is from about 1 ng to about 1,000 mg per kg of body weight and may be given once or more daily, weekly, monthly, or yearly. Persons of ordinary skill in the art can easily determine optimum dosages, dosing methodologies and repetition rates. One of skill in the art will be able to determine optimal dosing for administration of a combination of tucatinib, an anti-HER2 antibody, or capecitabine to a human being following established protocols known in the art and the disclosure herein.

Whether tucatinib, the anti-HER2 antibody, or the antimetabolite are administered simultaneously or sequentially, the doses of tucatinib, the anti-HER2 antibody, or the antimetabolite can be any dose described herein. In some embodiments, the doses of tucatinib, the anti-HER2 antibody, or the antimetabolite are therapeutically effective amounts. In some embodiments, the dose of tucatinib is a therapeutically effective amount and the dose of the anti-HER2 antibody or the antimetabolite are less than a therapeutically effective amount (i.e., one or more subsequent doses of the anti-HER2 antibody or the antimetabolite are administered in order for the therapeutically effective amount to be delivered to the subject). In some embodiments, the dose of the anti-HER2 antibody or the antimetabolite are a therapeutically effective amount and the dose of tucatinib is less than a therapeutically effective amount (i.e., one or more subsequent doses of tucatinib are administered in order for the therapeutically effective amount to be delivered to the subject). In some instances, the dose of tucatinib is about 150, 200, 250, or 300 mg (e.g., when administered twice daily), the dose of the anti-HER2 antibody is about 2 mg, 6 mg, or 8 mg per kg of the subject's body weight (e.g., when administered once per day or once every 2, 3, 4, 5, 6, 7, 8, 9, 10, 11, 12, 13, 14, 15, 16, 17, 18, 19, 20, 21, or more days), or the dose of the antimetabolite is about 1,000 mg per $mm^2$ of the subject's body surface area (e.g., when administered twice daily). In other instances, the dose of tucatinib is about 150, 200, 250, or 300 mg (e.g., when administered twice daily), the dose of the anti-HER2 antibody is about, 600 mg (e.g., when administered once per day or once every 2, 3, 4, 5, 6, 7, 8, 9, 10, 11, 12, 13, 14, 15, 16, 17, 18, 19, 20, 21, or more days), or the dose of the antimetabolite is about 1,000 mg per $mm^2$ of the subject's body surface area (e.g., when administered twice daily).

When tucatinib, the anti-HER2 antibody, or the antimetabolite are simultaneously co-administered to the subject, they can be administered by the same route, or by different routes. As a non-limiting example, tucatinib or the antimetabolite can be administered orally, and the anti-HER2 antibody can simultaneously be administered intravenously, intramuscularly, subcutaneously, or intraperitoneally.

For sequential co-administration, tucatinib can be administered before the anti-HER2 antibody or the antimetabolite, or vice versa. In some embodiments, tucatinib and the anti-HER2 antibody or the antimetabolite are administered by the same route, but administration of tucatinib and the anti-HER2 antibody or capecitabine are separated by some amount of time. In some embodiments, tucatinib and the anti-HER2 antibody or the antimetabolite are administered by different routes, and administration of tucatinib and the HER2 antibody or the antimetabolite are separated by some amount of time. As a non-limiting example, the tucatinib is administered orally, and the anti-HER2 antibody is subsequently administered by another route (e.g., intravenously, intramuscularly, subcutaneously, intratumorally, or intraperitoneally) sometime later, or vice versa. Furthermore, the antimetabolite can be administered orally, before or after tucatinib or the anti-HER2 antibody.

For sequential co-administration, one of skill in the art will readily be able to determine the appropriate amount of time between administration of tucatinib and the other agent or agents (i.e., the anti-HER2 antibody or the antimetabolite). In some embodiments, administration of tucatinib and the other agent or agents is separated by about 1, 2, 3, 4, 5, 6, 7, 8,9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 50, 51, 52, 53, 54, 55, 56, 57, 58, 59, 60, or more minutes. In some embodiments, administration of tucatinib and the other agent or agents is separated by about 1, 2, 3, 4, 5, 6, 7, 8, 9, 10, 11, 12, 13, 14, 15, 16, 17, 18, 19, 20, 21, 22, 23, 24, or more hours. In some embodiments, administration of tucatinib and the other agent or agents is separated by about 1, 2, 3, 4, 5, 6, 7, or more days. In some embodiments, administration of tucatinib and the other agent or agents is separated by about 1, 2, 3, 4, 5, 6, 7, 8, 9, 10, 11, 12, or more weeks. In some embodiments, administration of tucatinib and the other agent or agents is separated by about 1, 2, 3, 4, 5, 6, 7, 8, 9, 10, 11, 12, 13, 14, 15, 16, 17, 18, 19, 20, 21, 22, 23, 24, or more months.

In some embodiments, tucatinib and the other agent or agents (i.e., the anti-HER2 antibody or the antimetabolite) are administered 1, 2, 3, 4, 5, or more times per day. In some embodiments, tucatinib, and the other agent or agents (e.g., the anti-HER2 antibody and the chemotherapeutic agent) are administered 1, 2, 3, 4, 5, 6, 7, or more times per week. In some embodiments, tucatinib and the other agent or agents are administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more times per month.

In some embodiments, tucatinib and the other agent or agents are administered once about every 1, 2, 3, 4, 5, 6, 7, 8, 9, 10, or more days. In some embodiments, tucatinib and the other agent or agents are administered about once every 1, 2, 3, 4, or more weeks. In some embodiments, tucatinib and the other agent or agents are administered once about every 1, 2, 3, 4, 5, 6, 7, 8, 9, 10, 11, 12, or more months.

Following successful treatment, it may be desirable to have the subject undergo maintenance therapy to prevent the recurrence of the cancer (e.g., colorectal cancer, esophageal cancer, gastric cancer, cholangiocarcinoma, non-small cell lung cancer, bladder cancer, biliary cancer, breast cancer, or a combination thereof).

Determination of a therapeutically effective amount is well within the capability of those skilled in the art, especially in light of the detailed disclosure provided herein. Generally, an efficacious or therapeutically effective amount of a composition (e.g., comprising a combination of tucatinib and the other agent or agents) is determined by first administering a low dose or small amount of the composition, and then incrementally increasing the administered dose or dosages, until a desired effect of is observed in the treated subject with minimal or no toxic side effects.

Single or multiple administrations of a composition (e.g., comprising a combination of tucatinib and the other agent or agents) are administered depending on the dosage and frequency as required and tolerated by the patient. In any event, the composition should provide a sufficient quantity of the composition to effectively treat the patient. Generally, the dose is sufficient to prevent, treat, or ameliorate effects, symptoms, or signs of disease without producing unacceptable toxicity to the patient.

In some embodiments, treating the subject comprises inhibiting cancer (e.g., colorectal cancer, esophageal cancer, gastric cancer, cholangiocarcinoma, non-small cell lung cancer, bladder cancer, biliary cancer, breast cancer, or a combination thereof) cell growth, inhibiting cancer cell proliferation, inhibiting cancer cell migration, inhibiting cancer cell invasion, decreasing or eliminating one or more signs or symptoms of cancer, reducing the size (e.g., volume) of a cancer tumor, reducing the number of cancer tumors, reducing the number of cancer cells, inducing cancer cell necrosis, pyroptosis, oncosis, apoptosis, autophagy, or other cell death, increasing survival time of the subject, or enhancing the therapeutic effects of another drug or therapy. In particular instances, the subject does not have cancer.

Tumor size (e.g., volume) can be measured using techniques including, but not limited to, X-ray imaging, computed tomography (CT) with or without contrast, magnetic resonance imaging (MRI) with or without contrast, positron emission tomography (PET), ultrasound, and combinations thereof. In some embodiments, the presence or size of tumor metastases (e.g., within the chest, abdomen, pelvis, or brain) are measured. Tumor sites can also be monitored using methods such as photography (e.g., skin photography), biopsy, bone imaging, laparoscopy, and endoscopy.

In some embodiments, treating the subject results in a tumor growth inhibition (TGI) index that is between about 10% and 70% (e.g., about 10%, 15%, 20%, 25%, 30%, 35%, 40%, 45%, 50%, 55%, 60%, 65%, or 70%). Preferably, treating the subject results in a TGI index that is at least about 70% (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%). More preferably, treating the subject results in a TGI index that is at least about 85% (e.g., about 85%, 86%, 87%, 88%, 89%, 90%, 91%, 92%, 93%, 94%, 95%, 96%, 97%, 98%, 99%, or 100%). Even more preferably, treating the subject results in a TGI index that is at least about 95% (e.g., about 95%, 96%, 97%, 98%, 99%, or 100%). Most preferably, treating the subject results in a TGI index that is about 100% or more (e.g., about 100%, 101%, 102%, 103%, 104%, 105%, 106%, 107%, 108%, 109%, 110%, 111%, 112%, 113%, 114%, 115%, 116%, 117%, 118%, 119%, 120%, 125%, 130%, 135%, 140%, 145%, 150%, or more).

In particular embodiments, treating the subject results in a TGI index that is greater than the TGI index that is observed when tucatinib and the other agent or agents are used alone. In some instances, treating the subject results in a TGI index that is greater than the TGI index that is observed when tucatinib is used alone. In other instances, treating the subject results in a TGI index that is greater than the TGI index that is observed when an anti-HER2 antibody is used alone. In some embodiments, treating the subject results in a TGI index that is greater than the TGI index that is observed when a chemotherapeutic agent (e.g., an antimetabolite, such as capectabine) is used alone. In some embodiments, treating the subject results in a TGI index that is at least about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, or 80% greater than the TGI index that is observed when tucatinib, an anti-HER2 antibody, or a chemotherapeutic agent is used alone.

In some embodiments, the combination of the anti-HER2 antibody, tucatinib, and the chemotherapeutic agent (e.g., an antimetabolite, such as capectabine) is synergistic. In particular embodiments, with respect to the synergistic combination, treating the subject results in a TGI index that is greater than the TGI index that would be expected if the combination of tucatinib, an anti-HER2 antibody, and the chemotherapeutic agent produced an additive effect. In some instances, the TGI index observed when a combination of the anti-HER2 antibody, tucatinib, and the chemotherapeutic agent is administered is at least about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, or 80% greater than the TGI index that would be expected if the combination of tucatinib, an anti-HER2 antibody, and the antimetabolite produced an additive effect.

In some embodiments, the HER2 status of a sample cell is determined. The determination can be made before treatment (i.e., administration of tucatinib, an anti-HER2 antibody, and a chemotherapeutic agent) begins, during treatment, or after treatment has been completed. In some instances, determination of the HER2 status results in a decision to change therapy (e.g., switching to a different anti-HER2 antibody, adding another anti-HER2 antibody to the treatment regimen, discontinuing the use of an anti-HER2 antibody, tucatinib, or a chemotherapeutic agent, discontinuing therapy altogether, or switching from another treatment method to a method of the present invention).

In some embodiments, the sample cell is determined to be overexpressing or not overexpressing HER2. In particular embodiments, the cell is determined to be HER2 3+, HER2 2+, HER2 1+, or HER2 0 (i.e., HER is not overexpressed).

In some embodiments, the sample cell is a cancer cell. In some instances, the sample cell is obtained from a subject who has cancer. The sample cell can be obtained as a biopsy specimen, by surgical resection, or as a fine needle aspirate (FNA). In some embodiments, the sample cell is a circulating tumor cell (CTC).

HER2 expression can be compared to a reference cell. In some embodiments, the reference cell is a non-cancer cell obtained from the same subject as the sample cell. In some embodiments, the reference cell is a non-cancer cell obtained from a different subject or a population of subjects. In some embodiments, measuring expression of HER2 comprises, for example, determining HER2 gene copy number or amplification, nucleic acid sequencing (e.g., sequencing of genomic DNA or cDNA), measuring mRNA expression, measuring protein abundance, or a combination thereof. HER2 testing methods include immunohistochemistry (IHC), fluorescence in situ hybridization (FISH), chromogenic in situ hybridization (CISH), ELISAs, and RNA quantification (e.g., of HER2 expression) using techniques such as RT-PCR and microarray analysis.

In some embodiments, the sample cell is determined to be HER2 positive when HER2 is expressed at a higher level in the sample cell compared to a reference cell. In some embodiments, the cell is determined to be HER2 positive when HER2 is overexpressed at least about 1.5-fold (e.g., about 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, or more) compared to a reference cell. In particular embodiments, the cell is determined to be HER2 positive when HER2 is overexpressed at least about 1.5-fold compared to the reference cell.

In some embodiments, the sample cell is determined to be HER2 positive when the FISH or CISH signal ratio is greater than 2. In some embodiments, the sample cell is determined to be HER2 positive when the HER2 gene copy number is greater than 6.

In some embodiments, the genotypes of one or more genes are determined in a sample cell. In some instances, the genotypes or sequences of KRAS, NRAS, or BRAF are determined. An entire gene or only part of a gene can be genotyped. In particular instances, only the exons are genotyped. Genotyping can be done before treatment (i.e., administration of tucatinib, an anti-HER2 antibody, or a chemotherapeutic agent) begins, during a treatment program, or after treatment has been completed. In some instances, genotyping results in a decision to change therapy (e.g., switching to a different anti-HER2 antibody, adding another anti-HER2 antibody to the treatment regimen, discontinuing the use of an anti-HER2 antibody, tucatinib, or a chemotherapeutic agent, discontinuing therapy altogether, or switching from another treatment method to a method of the present invention).

In some embodiments, treatment is administered when the cancer comprises a cell that has a wild-type KRAS genotype. In some instances, the cancer comprises a cell that has a wild-type genotype in exon 2 of KRAS. In particular instances, the cancer comprises a cell that has a wild-type genotype in codon 12 or codon 13 of KRAS. In some embodiments, treatment is administered when the cancer comprises a cell that has a wild-type NRAS genotype. In some embodiments, treatment is administered when the cancer comprises a cell that has a wild-type BRAF genotype. In particular embodiments, treatment is administered when the cancer comprises a cell that has a wild-type genotype in a combination of KRAS, NRAS, or BRAF. The cancer cell can be obtained as a biopsy specimen, by surgical resection, or as a fine needle aspirate (FNA). In some embodiments, the cancer cell is a circulating tumor cell (CTC).

In some aspects, the present invention sets forth a method for treating or ameliorating the effects of a HER2 positive cancer in a subject, the method comprising: administering a combination therapy comprising an anti-HER2 antibody in combination with and tucatinib and an antimetabolite, thereby treating the HER2 positive cancer.

In some aspects, the combination therapy further comprises a chemotherapeutic agent. In some aspects, the chemotherapeutic agent is an antimetabolite. In some aspects, the antimetabolite is a member selected from capecitabine, carmofur, doxifluridine, fluorouracil, tegafur, and a combination thereof. In some aspects, the antimetabolite is capecitabine.

In some aspects, the cancer is selected from colorectal cancer, esophageal cancer, gastric cancer, cholangiocarcinoma, non-small cell lung cancer, bladder cancer, biliary cancer, breast cancer, and a combination thereof. In some aspects, the cancer is an unresectable locally advanced cancer or a metastatic cancer. In some aspects, the cancer is breast cancer.

In some aspects, the antimetabolite is a member selected from capecitabine, carmofur, doxifluridine, fluorouracil, tegafur, and a combination thereof wherein the subject had prior treatment with trastuzumab, pertuzumab, and T-DM1. In some aspects, the antimetabolite is capecitabine.

In some aspects, the anti-HER2 antibody is a member selected from trastuzumab, pertuzumab, ado-trastuzumab emtansine, margetuximab, and a combination thereof. In some aspects, the anti-HER2 antibody is trastuzumab. In some aspects, the anti-HER2 antibody is a combination of trastuzumab and pertuzumab.

In some aspects, wherein the administration of the anti-HER2 antibody is before, during, or after the administration of tucatinib.

In some aspects, the cancer includes a cell that has a wild-type KRAS exon 2 genotype. In some aspects, the cancer includes a cell that has a wild-type NRAS genotype. In some aspects, the cancer includes a cell that has a wild-type BRAF genotype.

In some aspects, the subject has a cancer which is relapsed or refractory to a standard of care (e.g., a standard of care that includes cetuximab or panitumumab).

In some aspects, treating the subject results in a tumor growth inhibition (TGI) index of at least about 85%. In some aspects, treating the subject results in a TGI index of about 100%.

In some aspects, the combination of the anti-HER2 antibody and tucatinib is synergistic. In some aspects, treating the subject results in a TGI index that is greater than the TGI index observed when using an anti-HER2 antibody or tucatinib alone.

In some aspects, a dose of tucatinib is about 3 to 7 mg per kg of the subject's body weight twice daily. In some aspects, a dose of tucatinib is about 300 mg twice per day.

In some aspects, a dose of the anti-HER2 antibody is about 6 mg to 8 mg per kg of the subject's body weight once every three weeks. In some aspects, a dose of the anti-HER2 antibody is about 600 mg once every three weeks.

In some aspects, the tucatinib or the anti-HER2 antibody is administered orally, intravenously, or subcutaneously (e.g., orally).

In some aspects, the antimetabolite is administered orally.

In some aspects, a dose of the antimetabolite (e.g., capecitabine) is about 1,000 mg per $m^2$ of the subject's body surface area twice per day.

In some aspects, the anti-HER2 antibody is administered intravenously or subcutaneously.

In some aspects, one or more therapeutic effects in the subject is improved after administration of the combination therapy relative to a baseline. In some aspects, the one or more therapeutic effects is selected from the group consisting of: size of a tumor derived from the cancer, objective response rate, duration of response, time to response, progression free survival, and overall survival.

In some aspects, the size of a tumor derived from the cancer is reduced by at least about 10%. In some aspects, the size of the tumor is reduced by at least about 15%, at least about 20%, at least about 25%, at least about 30%, at least about 35%, at least about 40%, at least about 45%, at least about 50%, at least about 60%, at least about 70%, or at least about 80% relative to the size of the tumor derived from the cancer before administration of the combination therapy.

In some aspects, the objective response rate is at least about 20%. In some aspects, the objective response rate is at least about 25%, at least about 30%, at least about 35%, at least about 40%, at least about 45%, at least about 50%, at least about 60%, at least about 70%, or at least about 80%.

In some aspects, the subject exhibits progression-free survival of at least about 1 month after administration of the combination therapy. In some aspects, the subject exhibits at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the combination therapy.

In some aspects, the subject exhibits overall survival of at least about 1 month after administration of the combination therapy. In some aspects, the subject exhibits at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the combination therapy.

In some aspects, the duration of response to the antibody-drug conjugate is at least about 1 month after administration of the combination therapy. In some aspects, the duration of response is at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about eighteen months, at least about two years, at least about three years, at least about four years, or at least about five years after administration of the combination therapy.

In some aspects, the subject has one or more adverse events and is further administered an additional therapeutic agent to eliminate or reduce the severity of the one or more adverse events.

In some aspects, the subject is at risk of developing one or more adverse events and is further administered an additional therapeutic agent to prevent or reduce the severity of the one or more adverse events.

In some aspects, the one or more adverse events is a grade 2 or greater adverse event. In some aspects, the one or more adverse events is a grade 3 or greater adverse event. In some aspects, the one or more adverse events is a serious adverse event.

In some aspects, the subject is a human.

In some aspects, the present invention provides a method for treating a HER2 positive cancer in a subject that has exhibited an adverse event after starting treatment with a combination therapy comprising an anti-HER2 antibody and tucatinib at an initial dosage level, comprising administering to the subject the combination therapy at a reduced dosage level.

In some aspects, the combination therapy further includes a chemotherapeutic agent. In some aspects, the chemotherapeutic agent is an antimetabolite. In some aspects, the antimetabolite is a member selected from the group consisting of capecitabine, carmofur, doxidluridine, fluorouracil, tegafur, and a combination thereof. In some aspects, the antimetabolite is capecitabine.

In some aspects, the one or more adverse events is a grade 2 or greater adverse event. In some aspects, the one or more adverse events is a grade 3 or greater adverse event. In some aspects, the adverse event is hepatotoxicity. In some aspects, the adverse event is left ventricular dysfunction. In some aspects, the adverse event is prolongation of the QTc interval.

In some aspects, the cancer is an unresectable locally advanced cancer or a metastatic cancer. In some aspects, the cancer is breast cancer.

In some aspects, the subject had prior treatment with trastuzumab, pertuzumab, and T-DM1.

In some aspects, the initial dosage level of tucatinib is about 300 mg twice daily. In some aspects, the reduced dosage level of tucatinib is about 250 mg twice daily. In some aspects, the reduced dosage level of tucatinib is about 200 mg twice daily. In some aspects, the reduced dosage level of tucatinib is about 150 mg twice daily.

B. Pharmaceutical Compositions

In another aspect, the present invention provides a pharmaceutical composition comprising tucatinib, an anti-HER2 antibody, and a pharmaceutically acceptable carrier. In some embodiments, the anti-HER2 antibody is a member selected from the group consisting of trastuzumab, pertuzumab, ado-trastuzumab emtansine, margetuximab, and a combination thereof. In some instances, the anti-HER2 antibody is trastuzumab. In some instances, the anti-HER2 antibody is a combination of trastuzumab and pertuzumab. In some embodiments, the pharmaceutical composition further comprises a chemotherapeutic agent (e.g., an antimetabolite, such as capecitabine).

In some embodiments, tucatinib is present at a concentration between about 0.1 nM and 10 nM (e.g., about 0.1, 0.2, 0.3, 0.4, 0.5 0.6, 0.7, 0.8, 0.9, 1.0, 1.5, 2, 2.5, 3, 3.5, 4, 4.5, 5, 5.5, 6, 6.5, 7, 7.5, 8, 8.5, 9, 9.5, or 10 nM). In some embodiments, tucatinib is present at a concentration between about 10 nM and 100 nM (e.g., about 10, 15, 20, 25, 30, 35, 40, 45, 50, 55, 60, 65, 70, 75, 80, 85, 90, 95, or 100 nM). In some embodiments, tucatinib is present at a concentration between about 100 nM and 1,000 nM (e.g., about 100, 150, 200, 250, 300, 350, 400, 450, 500, 550, 600, 650, 700, 750, 800, 850, 900, 950, or 1,000 nM). In some embodiments, tucatinib is present at a concentration at least about 1,000 nM to 10,000 nM (e.g., at least about 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000, or more nM).

In some embodiments, the anti-HER2 antibody is present at a concentration between about 0.1 nM and 10 nM (e.g., about 0.1, 0.2, 0.3, 0.4, 0.5 0.6, 0.7, 0.8, 0.9, 1.0, 1.5, 2, 2.5, 3, 3.5, 4, 4.5, 5, 5.5, 6, 6.5, 7, 7.5, 8, 8.5, 9, 9.5, or 10 nM). In some embodiments, the anti-HER2 antibody is present at a concentration between about 10 nM and 100 nM (e.g., about 10, 15, 20, 25, 30, 35, 40, 45, 50, 55, 60, 65, 70, 75, 80, 85, 90, 95, or 100 nM). In some embodiments, the anti-HER2 antibody is present at a concentration between about 100 nM and 1,000 nM (e.g., about 100, 150, 200, 250, 300, 350, 400, 450, 500, 550, 600, 650, 700, 750, 800, 850, 900, 950, or 1,000 nM). In some embodiments, the anti-HER2 antibody is present at a concentration of at least about 1,000 nM to 10,000 nM (e.g., at least about 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000, or more nM).

In some embodiments, the chemotherapeutic agent (e.g., an antimetabolite, such as capecitabine) is present at a concentration between about 0.1 nM and 10 nM (e.g., about 0.1, 0.2, 0.3, 0.4, 0.5 0.6, 0.7, 0.8, 0.9, 1.0, 1.5, 2, 2.5, 3, 3.5, 4, 4.5, 5, 5.5, 6, 6.5, 7, 7.5, 8, 8.5, 9, 9.5, or 10 nM). In some embodiments, the antimetabolite is present at a concentration between about 10 nM and 100 nM (e.g., about 10, 15, 20, 25, 30, 35, 40, 45, 50, 55, 60, 65, 70, 75, 80, 85, 90, 95, or 100 nM). In some embodiments, the chemotherapeutic agent (e.g., a antimetabolite, such as capecitabine) is present at a concentration between about 100 nM and 1,000 nM (e.g., about 100, 150, 200, 250, 300, 350, 400, 450, 500, 550, 600, 650, 700, 750, 800, 850, 900, 950, or 1,000 nM). In some embodiments, the chemotherapeutic agent (e.g., a antimetabolite, such as capecitabine) is present at a concentration of at least about 1,000 nM to 10,000 nM (e.g., at least about 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 6,100, 6,200, 6,300, 6,400, 6,500, 6,600, 6,700, 6,800, 6,900, 7,000, 7,100, 7,200, 7,300, 7,400, 7,500, 7,600, 7,700, 7,800, 7,900, 8,000, 8,100, 8,200, 8,300, 8,400, 8,500, 8,600, 8,700, 8,800, 8,900, 9,000, 9,100, 9,200, 9,300, 9,400, 9,500, 9,600, 9,700, 9,800, 9,900, 10,000, or more nM).

The pharmaceutical compositions of the present invention may be prepared by any of the methods well-known in the art of pharmacy. Pharmaceutically acceptable carriers suitable for use with the present invention include any of the standard pharmaceutical carriers, buffers and excipients, including phosphate-buffered saline solution, water, and emulsions (such as an oil/water or water/oil emulsion), and various types of wetting agents or adjuvants. Suitable pharmaceutical carriers and their formulations are described in Remington's Pharmaceutical Sciences (Mack Publishing Co., Easton, 19th ed. 1995). Preferred pharmaceutical carriers depend upon the intended mode of administration of the active agent.

The pharmaceutical compositions of the present invention can include a combination of drugs (e.g., tucatinib, an anti-HER2 antibody, or a chemotherapeutic agent), or any pharmaceutically acceptable salts thereof, as active ingredients and a pharmaceutically acceptable carrier or excipient or diluent. A pharmaceutical composition may optionally contain other therapeutic ingredients.

The compositions (e.g., comprising tucatinib, an anti-HER2 antibody, a chemotherapeutic agent, or a combination thereof) can be combined as the active ingredients in intimate admixture with a suitable pharmaceutical carrier or excipient according to conventional pharmaceutical compounding techniques. Any carrier or excipient suitable for the form of preparation desired for administration is contemplated for use with the compounds disclosed herein.

The pharmaceutical compositions include those suitable for oral, topical, parenteral, pulmonary, nasal, or rectal administration. The most suitable route of administration in any given case will depend in part on the nature and severity of the cancer condition and also optionally the HER2 status or stage of the cancer.

Other pharmaceutical compositions include those suitable for systemic (e.g., enteral or parenteral) administration. Systemic administration includes oral, rectal, sublingual, or sublabial administration. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In particular embodiments, pharmaceutical compositions of the present invention may be administered intratumorally.

Compositions for pulmonary administration include, but are not limited to, dry powder compositions consisting of the powder of a compound described herein (e.g., tucatinib, an anti-HER2 antibody, a chemotherapeutic agent, or a combination thereof), or a salt thereof, and the powder of a suitable carrier or lubricant. The compositions for pulmonary administration can be inhaled from any suitable dry powder inhaler device known to a person skilled in the art.

Compositions for systemic administration include, but are not limited to, dry powder compositions consisting of the composition as set forth herein (e.g., tucatinib, an anti-HER2 antibody, a chemotherapeutic agent, or a combination thereof) and the powder of a suitable carrier or excipient. The compositions for systemic administration can be represented by, but not limited to, tablets, capsules, pills, syrups, solutions, and suspensions.

In some embodiments, the compositions (e.g., tucatinib, an anti-HER2 antibody, a chemotherapeutic agent, or a combination thereof) further include a pharmaceutical surfactant. In some embodiments, the compositions further include a cryoprotectant. In some embodiments, the cryoprotectant is selected from the group consisting of glucose, sucrose, trehalose, lactose, sodium glutamate, PVP, HPPCD, CD, glycerol, maltose, mannitol, and saccharose.

Pharmaceutical compositions or medicaments for use in the present invention can be formulated by standard techniques using one or more physiologically acceptable carriers or excipients. Suitable pharmaceutical carriers are described herein and in Remington: The Science and Practice of Pharmacy, 21st Ed., University of the Sciences in Philadelphia, Lippencott Williams & Wilkins (2005).

Controlled-release parenteral formulations of the compositions (e.g., tucatinib, an anti-HER2 antibody, a chemotherapeutic agent, or a combination thereof) can be made as implants, oily injections, or as particulate systems. For a broad overview of delivery systems see Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995), which is incorporated herein by reference. Particulate systems include microspheres, microparticles, microcapsules, nanocapsules, nanospheres, and nanoparticles.

Polymers can be used for ion-controlled release of compositions of the present invention. Various degradable and nondegradable polymeric matrices for use in controlled drug delivery are known in the art (Langer R., Accounts Chem. Res., 26:537-542 (1993)). For example, the block copolymer, polaxamer 407 exists as a viscous yet mobile liquid at low temperatures but forms a semisolid gel at body temperature. It has been shown to be an effective vehicle for formulation and sustained delivery of recombinant interleukin 2 and urease (Johnston et al., Pharm. Res., 9:425-434 (1992); and Pec et al., J. Parent. Sci. Tech., 44(2):58 65 (1990)). Alternatively, hydroxyapatite has been used as a microcarrier for controlled release of proteins (Ijntema et al., Int. J. Pharm., 112:215-224 (1994)). In yet another aspect, liposomes are used for controlled release as well as drug targeting of the lipid-capsulated drug (Betageri et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and U.S. Pat. Nos. 5,019,369, 5,055,303; 5,514,670; 5,413,797; 5,268, 164; 5,004,697; 4,902,505; 5,506,206, 5,271,961; 5,254,342 and 5,534,496, each of which is incorporated herein by reference.

For oral administration of a combination of tucatinib, or an anti-HER2 antibody, or a chemotherapeutic agent, a pharmaceutical composition or a medicament can take the form of, for example, a tablet or a capsule prepared by conventional means with a pharmaceutically acceptable excipient. The present invention provides tablets and gelatin capsules comprising tucatinib, an anti-HER2 antibody, a chemotherapeutic agent, or a combination thereof, or a dried solid powder of these drugs, together with (a) diluents or fillers, e.g., lactose, dextrose, sucrose, mannitol, sorbitol, cellulose (e.g., ethyl cellulose, microcrystalline cellulose), glycine, pectin, polyacrylates or calcium hydrogen phosphate, calcium sulfate, (b) lubricants, e.g., silica, talcum, stearic acid, magnesium or calcium salt, metallic stearates, colloidal silicon dioxide, hydrogenated vegetable oil, corn starch, sodium benzoate, sodium acetate or polyethyleneglycol; for tablets also (c) binders, e.g., magnesium aluminum silicate, starch paste, gelatin, tragacanth, methylcellulose, sodium carboxymethylcellulose, polyvinylpyrrolidone or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, or sweetening agents as appropriate. If desired, preparations for oral administration can be suitably formulated to give controlled release of the active compound(s).

Typical formulations for topical administration of tucatinib, an anti-HER2 antibody, a chemotherapeutic agent, or a combination thereof include creams, ointments, sprays, lotions, and patches. The pharmaceutical composition can, however, be formulated for any type of administration, e.g., intradermal, subdermal, intravenous, intramuscular, subcutaneous, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral or rectal administration is also contemplated.

Suitable formulations for transdermal application include an effective amount of one or more compounds described herein, optionally with a carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

The compositions and formulations set forth herein (e.g., tucatinib, an anti-HER2 antibody, a chemotherapeutic agent, or a combination thereof) can be formulated for parenteral administration by injection, for example by bolus injection or continuous infusion. Formulations for injection can be presented in unit dosage form, for example, in ampules or in multi-dose containers, with an added preservative. Injectable compositions are preferably aqueous isotonic solutions or suspensions, and suppositories are preferably prepared from fatty emulsions or suspensions. The compositions may be sterilized or contain adjuvants, such as preserving, stabilizing, wetting or emulsifying agents, solution promoters, salts for regulating the osmotic pressure or buffers. Alternatively, the active ingredient(s) can be in powder form for constitution with a suitable vehicle, for example, sterile pyrogen-free water, before use. In addition, they may also contain other therapeutically valuable substances. The compositions are prepared according to conventional mixing, granulating or coating methods, respectively.

For administration by inhalation, the compositions (e.g., comprising tucatinib, an anti-HER2 antibody, a chemotherapeutic agent, or a combination thereof) may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound(s) and a suitable powder base, for example, lactose or starch.

The compositions (e.g., comprising tucatinib, an anti-HER2 antibody, a chemotherapeutic agent, or a combination thereof) can also be formulated in rectal compositions, for example, suppositories or retention enemas, for example, containing conventional suppository bases, for example, cocoa butter or other glycerides.

Furthermore, the active ingredient(s) can be formulated as a depot preparation. Such long-acting formulations can be administered by implantation (for example, subcutaneously or intramuscularly) or by intramuscular injection. Thus, for example, one or more of the compounds described herein can be formulated with suitable polymeric or hydrophobic materials (for example as an emulsion in an acceptable oil) or ion exchange resins, or as sparingly soluble derivatives, for example, as a sparingly soluble salt.

In some aspects, the present invention sets forth a pharmaceutical composition comprising an anti-HER2 antibody, tucatinib, a chemotherapeutic agent (e.g., an antimetabolite), and a pharmaceutically acceptable carrier.

In some aspects, the anti-HER2 antibody is a member selected from the group consisting of trastuzumab, pertuzumab, ado-trastuzumab emtansine, margetuximab, and a combination thereof. In some aspects, the anti-HER2 antibody is trastuzumab. In some aspects, the anti-HER2 antibody is a combination of trastuzumab and pertuzumab.

In some aspects, the chemotherapeutic agent is capecitabine.

C. Kits

In another aspect, the present invention provides a kit for treating or ameliorating the effects of cancer in a subject, the kit comprising a pharmaceutical composition of the present invention (e.g., a pharmaceutical composition comprising a combination of tucatinib, an anti-HER2 antibody, or a chemotherapeutic agent). In some embodiments, the anti-HER2 antibody is trastuzumab, pertuzumab, ado-trastuzumab emtansine, margetuximab, or a combination thereof. In some instances, the anti-HER2 antibody is trastuzumab. In some instances, the anti-HER2 antibody is a combination of trastuzumab and pertuzumab.

The kits are suitable for treating or ameliorating the effects of any number of cancers, particularly HER2 positive or metastatic cancers. In some embodiments, the type of cancer that is treated or ameliorated is selected from the group consisting of colorectal cancer, gastric cancer, lung cancer (e.g., non-small cell lung cancer (NSCLC)), biliary cancers (e.g., cholangiocarcinoma, gallbladder cancer), bladder cancer, esophageal cancer, melanoma, ovarian cancer, liver cancer, prostate cancer, pancreatic cancer, small intestine cancer, head and neck cancer, uterine cancer, breast cancer, and cervical cancer. In some instances, the kits are suitable for treating cancers of unknown primary type, especially if they are HER2 positive. In particular embodiments, the cancer that is treated or ameliorated is selected from the group consisting of colorectal cancer, esophageal cancer, gastric cancer, cholangiocarcinoma, non-small cell lung cancer, bladder cancer, and biliary cancer. In some embodiments, the cancer is an advanced cancer. In some embodiments, the cancer is a drug-resistant cancer. In some instances, the cancer is a multidrug-resistant cancer. In some embodiments, the cancer is an unresectable, locally advanced cancer. In some embodiments, the cancer is a metastatic cancer.

Materials and reagents to carry out the various methods of the present invention can be provided in kits to facilitate execution of the methods. As used herein, the term "kit" includes a combination of articles that facilitates a process, assay, analysis, or manipulation. In particular, kits of the present invention find utility in a wide range of applications including, for example, diagnostics, prognostics, therapy, and the like.

Kits can contain chemical reagents as well as other components. In addition, the kits of the present invention can include, without limitation, instructions to the kit user, apparatus and reagents for administering combinations of tucatinib, anti-HER2 antibodies, antimetabolites, or pharmaceutical compositions thereof, sample tubes, holders, trays, racks, dishes, plates, solutions, buffers, or other chemical reagents. In some embodiments, the kits contain instructions, apparatus, or reagents for determining the genotype of a gene (e.g., KRAS, NRAS, BRAF) or determining the expression of HER2 in a sample. Kits of the present invention can also be packaged for convenient storage and safe shipping, for example, in a box having a lid.

In some aspects, the present invention sets forth a kit for treating or ameliorating the effects of a HER2 positive cancer in a subject, the kit comprising the pharmaceutical composition as otherwise described herein. In some aspects, the kit further comprises instructions for use. In some aspects, the kit further comprises one or more reagents.

IV. Examples

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

The examples provided herein demonstrate that tucatinib and trastuzumab were effective for inhibiting tumor growth in a number of patient-derived xenograft (PDX) models. In particular, tucatinib and trastuzumab were effective in treating tumors that were derived from HER2 positive cancers including colorectal cancer (CRC), esophageal cancer, gastric cancer, cholangiocarcinoma, and non-small cell lung cancer (NSCLC). Furthermore, a combination of tucatinib and trastuzumab was more effective at inhibiting tumor growth than either drug alone. In several tumors, a surprising synergistic effect was observed when the two drugs were used in combination.

Example 1: Combination of Tucatinib and Trastuzumab in Colorectal Cancer PDX Models In this example, the efficacy of tucatinib and trastuzumab was evaluated in PDX models of HER2 positive CRC. Mice were subcutaneously inoculated with CTG-0121, CTG-0784, or CTG-0383 cells, and subsequently treated with tucatinib, trastuzumab, or a combination of the two drugs (n=10 per group). Tucatinib was administered orally at a dose of 50 mg/kg twice per day for 28 days (study days 0-27). Trastuzumab was administered intraperitoneally at a dose of 20 mg/kg once every three days. Nine doses of trastuzumab were administered, starting on study day 0. A vehicle-only group was included as a negative control.

Figure 3A:
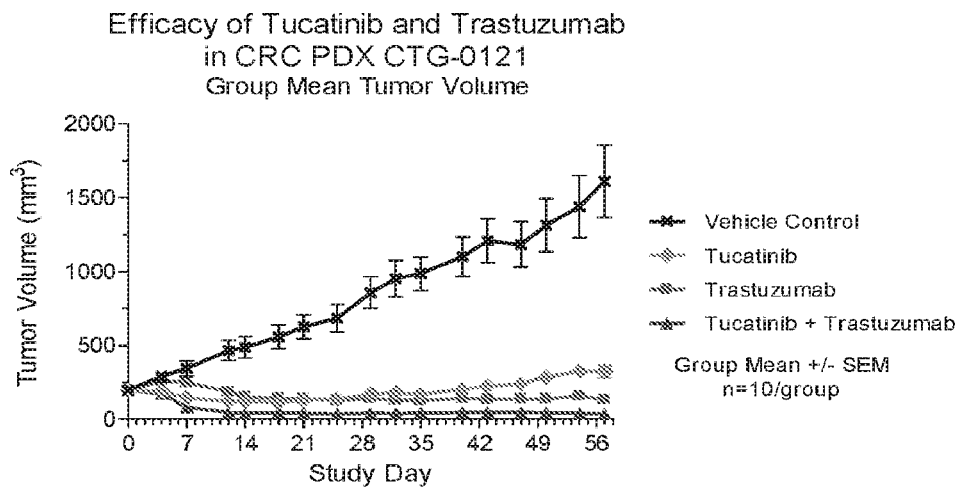
FIGS. 3A-3C show that a combination of tucatinib and trastuzumab was active in HER2 amplified colorectal cancer (CRC) patient-derived xenograft (PDX) models. Data are shown as group mean+/−S.E.M.
Figure 3B:
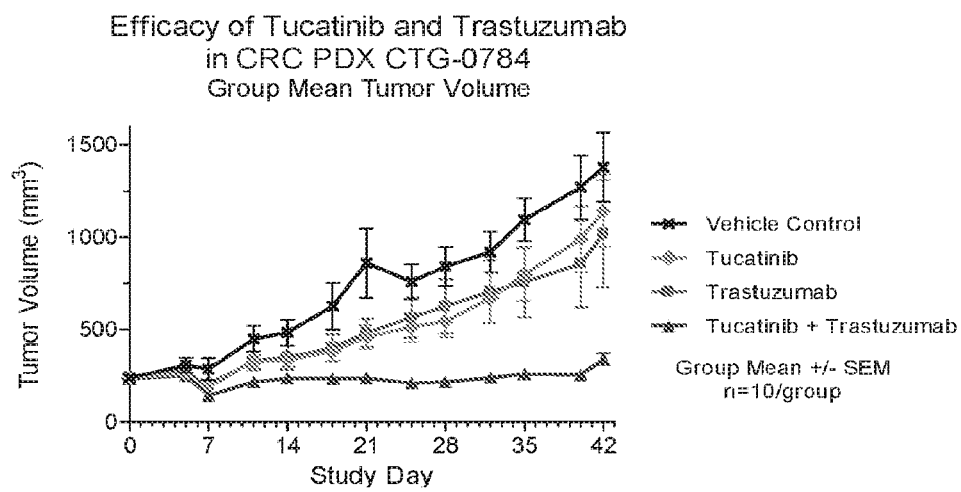
Figure 3C:
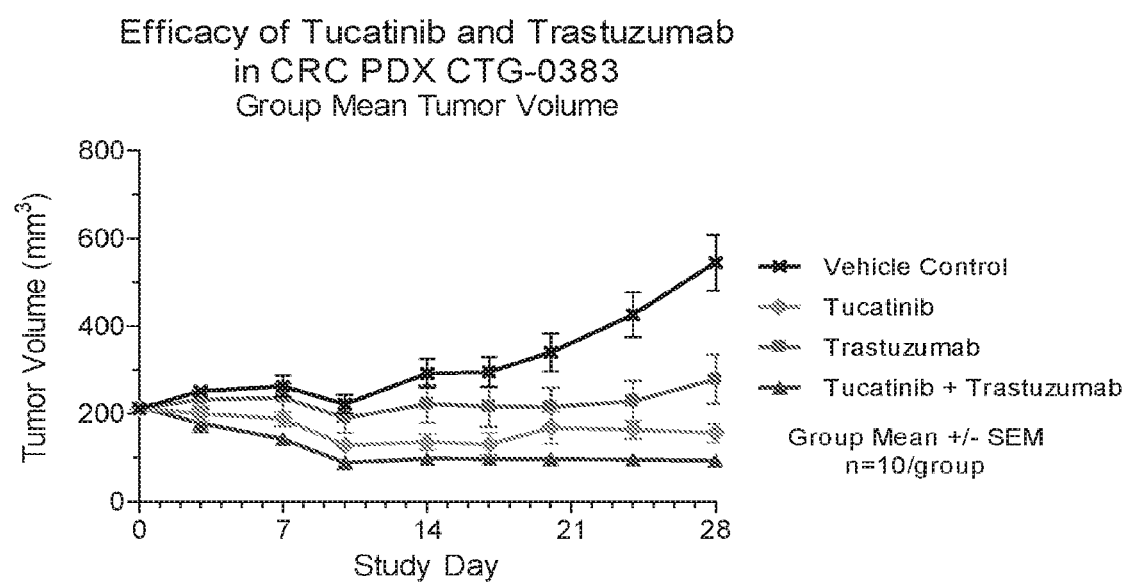

As shown in FIGS. 3A-3C, both tucatinib and trastuzumab inhibited tumor growth in all three CRC PDX models. Furthermore, when a combination of the two drugs was administered, the inhibition of tumor growth was more pronounced than when either drug was used individually. In the CTG-0121 model, tucatinib, trastuzumab, and a combination of the two drugs produced tumor growth inhibition (TGI) indices of 104%, 109%, and 124%, respectively, at study day 29 (Table 1). In the CTG-0784 model, tucatinib, trastuzumab, and a combination of the two drugs produced TGI indices of 50%, 36%, and 103%, respectively, at study day 29. In the CTG-0383 model, tucatinib, trastuzumab, and a combination of the two drugs produced TGI indices of 117%, 80%, and 137%, respectively, at study day 29. Surprisingly, a synergistic effect was observed when a combination of the two drugs was administered in all three models. Of note, the activity of a combination of tucatinib and trastuzumab in each HER2 positive CRC PDX model was comparable to activity observed in a HER2 positive breast cancer model (BT-474).

Example 2: Combination of Tucatinib and Trastuzumab in Esophageal Cancer PDX Models In this example, the efficacy of tucatinib and trastuzumab was evaluated in PDX models of HER2 positive esophageal cancer. Mice were subcutaneously inoculated with CTG-0137 or CTG-0138 cells, and subsequently treated with tucatinib, trastuzumab, or a combination of the two drugs (n=10 per group). Tucatinib was administered orally at a dose of 50 mg/kg twice per day for 28 days (study days 0-27). Trastuzumab was administered intraperitoneally at a dose of 20 mg/kg once every three days. Nine doses of trastuzumab were administered, starting on study day 0. A vehicle-only group was included as a negative control.

Figure 4A:
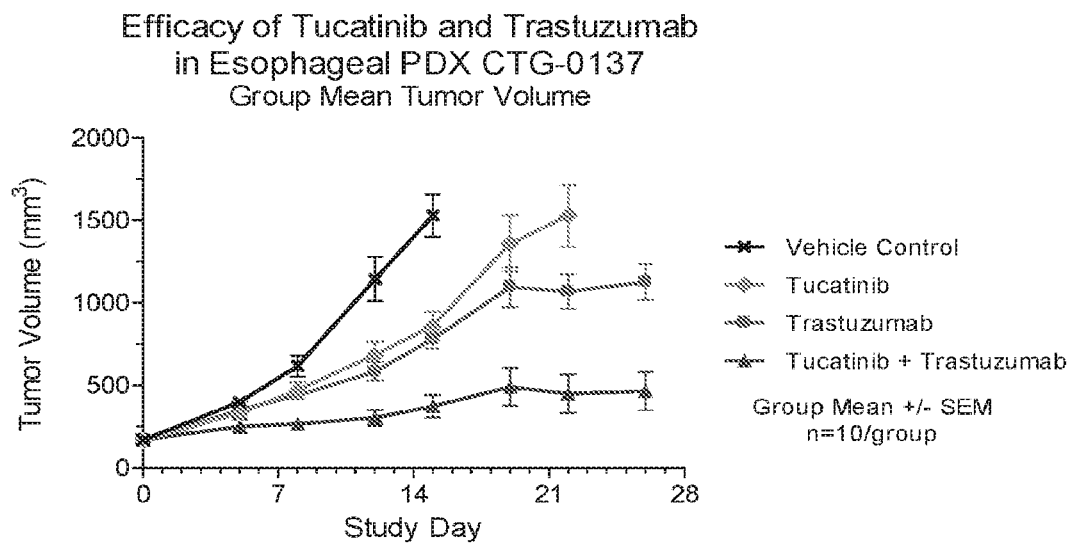
FIGS. 4A and 4B show that a combination of tucatinib and trastuzumab was active in HER2 amplified esophageal cancer patient-derived xenograft (PDX) models. Data are shown as group mean+/−S.E.M.

In the CTG-0137 model, both tucatinib and trastuzumab inhibited tumor growth, exhibiting TGI indices at study day 15 of 49% and 55%, respectively (FIG. 4A and Table 1). Furthermore, a synergistic effect was observed when a combination of the two drugs was administered, producing a TGI index of 85%.

Figure 4B:
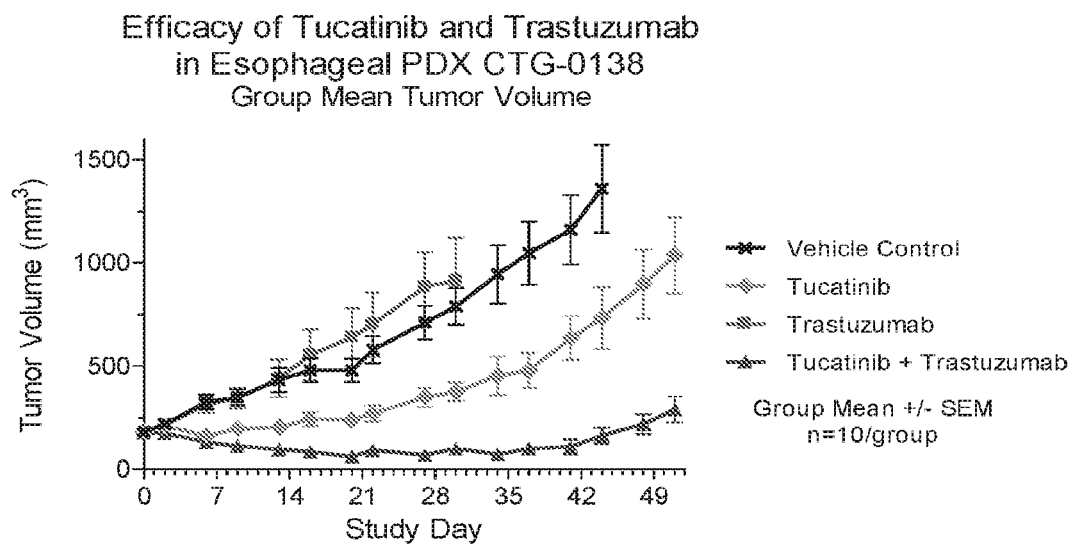

In the CTG-0138 model, tucatinib inhibited tumor growth when administered as a single agent, producing a TGI index of 69% at study day 30 (FIG. 4B). However, a synergistic effect was observed when tucatinib and trastuzumab were administered in combination, producing a TGI index of 120% (Table 1).

Example 3: Combination of Tucatinib and Trastuzumab in Gastric Cancer PDX Models In this example, the efficacy of tucatinib and trastuzumab was evaluated in PDX models of HER2 positive gastric cancer. Mice were subcutaneously inoculated with GXA 3038, GXA 3039, or GXA 3054 cells, and subsequently treated with tucatinib, trastuzumab, or a combination of the two drugs (n=10 per group). Tucatinib was administered orally at a dose of 50 mg/kg twice per day for 28 days (study days 0-27). Trastuzumab was administered intraperitoneally at a dose of 20 mg/kg once every three days. Nine doses of trastuzumab were administered, starting on study day 0. A vehicle-only group was included as a negative control.

Figure 5A:
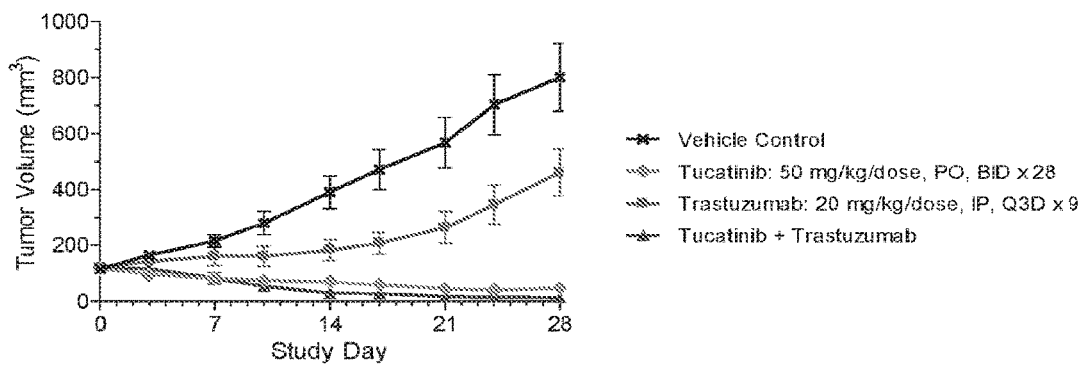
FIGS. 5A-5C show that a combination of tucatinib and trastuzumab was active in HER2 positive gastric cancer patient-derived xenograft (PDX) models. Data are shown as group mean+/−S.D.
Figure 5B:
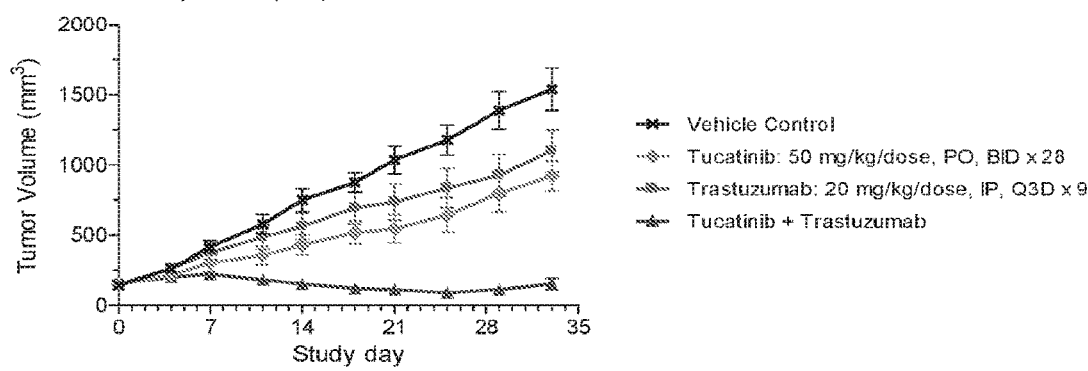
Figure 5C:
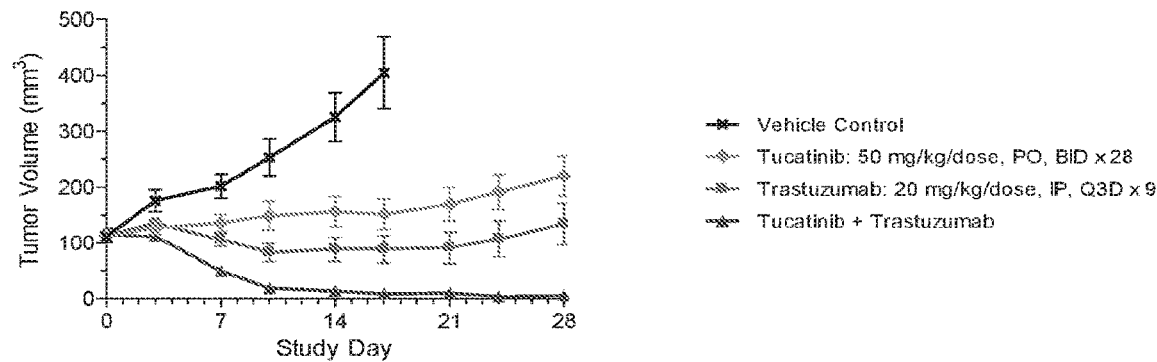

As shown in FIGS. 5A-5C, both tucatinib and trastuzumab inhibited tumor growth in all three gastric cancer PDX models. Furthermore, when a combination of the two drugs was administered, the inhibition of tumor growth was more pronounced than when either drug was used individually. In the GXA-3038 model, tucatinib, trastuzumab, and a combination of the two drugs produced TGI indices of 110%, 50%, and 116%, respectively, at study day 28 (Table 1). In the GXA-3039 model, tucatinib, trastuzumab, and a combination of the two drugs produced TGI indices of 48%, 38%, and 103%, respectively, at study day 29. In the GXA-3054 model, tucatinib, trastuzumab, and a combination of the two drugs produced TGI indices of 65%, 93%, and 136%, respectively, at study day 17. Surprisingly, a synergistic effect was observed when a combination of the two drugs was administered in all three models.

Example 4: Combination of Tucatinib and Trastuzumab in a Cholangiocarcinoma PDX Model In this example, the efficacy of tucatinib and trastuzumab was evaluated in a PDX model of HER2 positive cholangiocarcinoma. Mice were subcutaneously inoculated with CTG-0927 cells and subsequently treated with tucatinib, trastuzumab, or a combination of the two drugs (n=10 per group). Tucatinib was administered orally at a dose of 50 mg/kg twice per day for 28 days (study days 0-27). Trastuzumab was administered intraperitoneally at a dose of 20 mg/kg once every three days. Nine doses of trastuzumab were administered, starting on study day 0. A vehicle-only group was included as a negative control.

Figure 6:
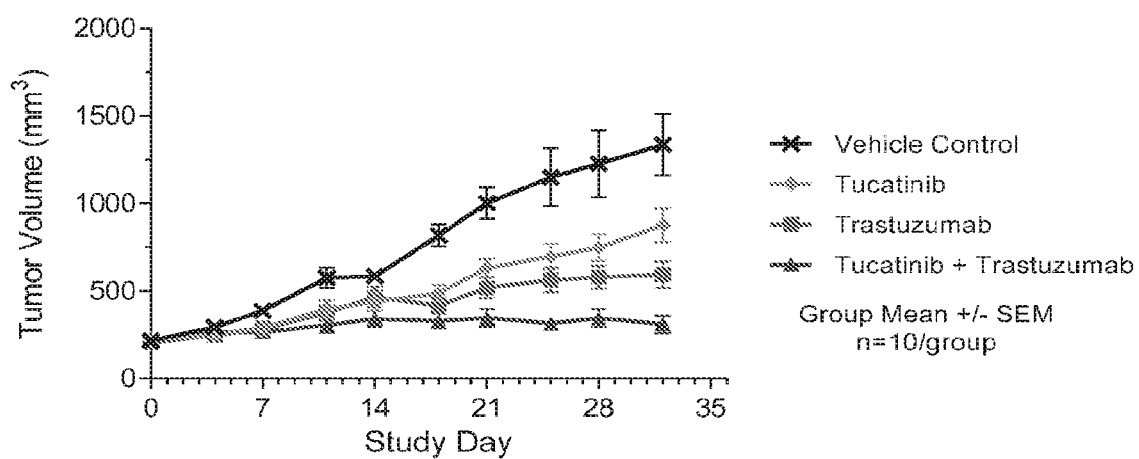
FIG. 6 shows that a combination of tucatinib and trastuzumab was active in a CTG-0927 HER2 positive cholangiocarcinoma patient-derived xenograft (PDX) model. Data are shown as mean+/−S.E.M.

As shown in FIG. 6 and Table 1, both tucatinib and trastuzumab inhibited tumor growth. Furthermore, when a combination of the two drugs was administered, the inhibition of tumor growth was more pronounced than when either drug was used individually. At study day 28, the TGI indices for the tucatinib, trastuzumab, and combination therapy groups were 48%, 63%, and 86%, respectively.

Example 5: Combination of Tucatinib and Trastuzumab in NSCLC Models

In this example, the efficacy of tucatinib and trastuzumab was evaluated in two different models of HER2 positive NSCLC. For these two studies, Calu-3 and NCI-H2170 cells were used, both of which express high levels of HER2, have gene amplification comparable to that of BT-474 breast cancer cells, and have previously demonstrated good responses to tucatinib in vitro.

Mice were subcutaneously inoculated with Calu-3 or NCI-H2170 cells and subsequently treated with tucatinib, trastuzumab, or a combination of the two drugs (n=10 per group). For the Calu-3 study, tucatinib was administered orally at a dose of 50 mg/kg twice per day for 21 days, beginning on study day 7. Trastuzumab was administered intraperitoneally at a dose of 20 mg/kg once every three days, beginning on study day 7. Seven doses of trastuzumab were administered. A vehicle-only group was included as a negative control. Three individual animals received dose holidays (one in the negative control group and two in the combination therapy group).

For the NCI-H2170 study, tucatinib was administered orally at a dose of 50 mg/kg twice per day for 21 days, beginning on study day 18. Trastuzumab was administered intraperitoneally at a dose of 20 mg/kg twice per week, beginning on study day 18. A vehicle-only group was included as a negative control.

Figure 7A:
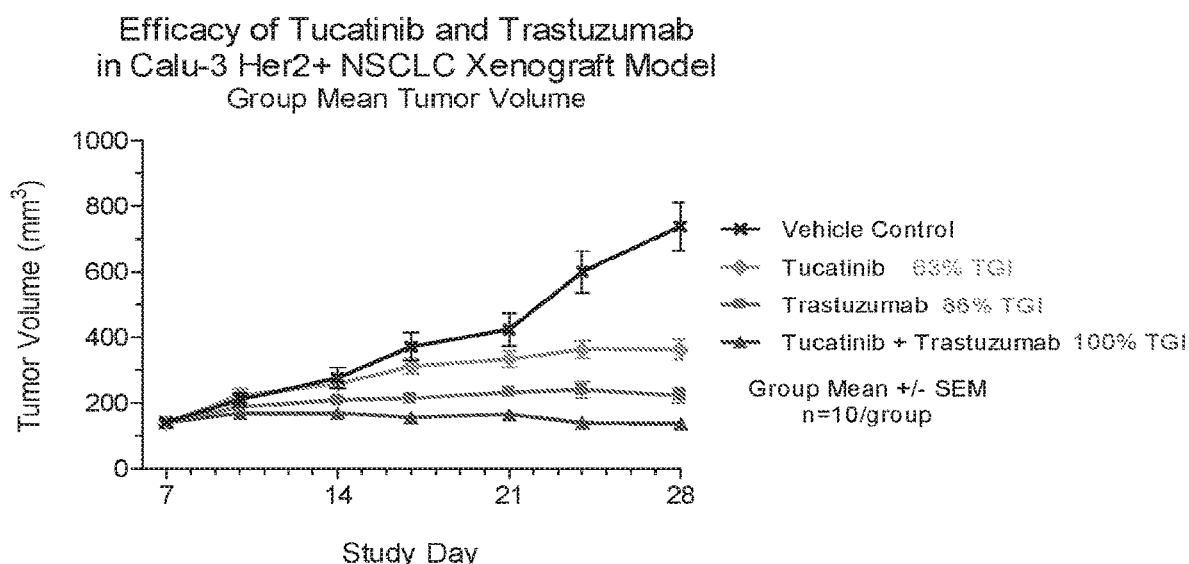
FIGS. 7A and 7B show that a combination of tucatinib and trastuzumab was active in HER2 positive non-small cell lung cancer (NSCLC) models. Data are shown as group mean+/−S.E.M.
Figure 7B:
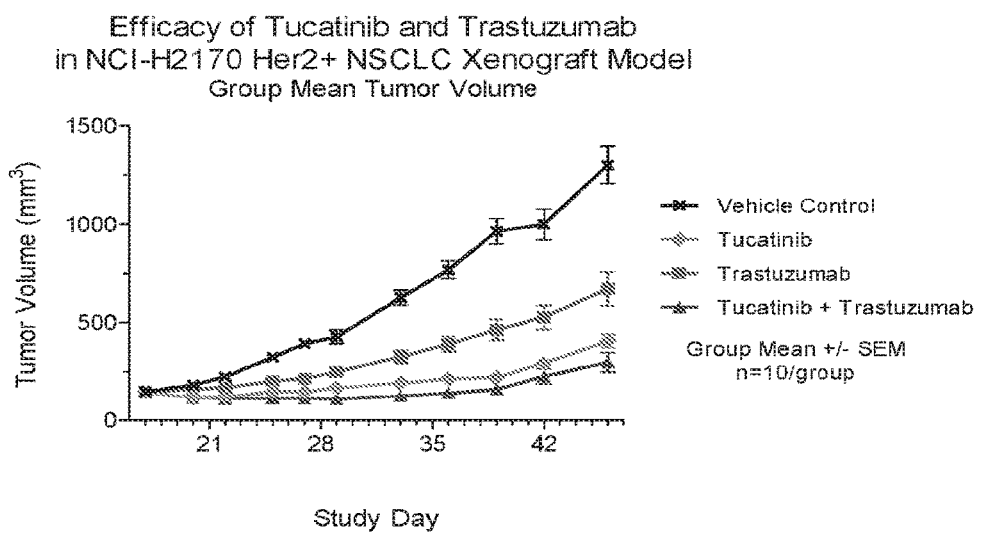

As shown in FIGS. 7A and 7B and Table 1, both tucatinib and trastuzumab inhibited tumor growth in both NSCLC models. Furthermore, when a combination of the two drugs was administered, the inhibition of tumor growth was more pronounced than when either drug was used individually. For the Calu-3 model, tucatinib, trastuzumab, and a combination of the two drugs produced tumor growth inhibition (TGI) indices of 63%, 86%, and 100%, respectively, at study day 28. Surprisingly, a synergistic effect was observed in the combination therapy group. For the NCI-2170 model, tucatinib, trastuzumab, and a combination of the two drugs produced TGI indices of 91%, 61%, and 98%, respectively, at study day 39.

press HER2 are more aggressive and historically have been associated with poorer overall survival (OS) compared to HER2 negative cancers (5).

The introduction of HER2-targeted therapy using either antibody-based therapy or a small molecule tyrosine kinase inhibitor (TKI) has led to significant and ongoing improvements in disease-free survival (DFS), progression-free survival (PFS), and OS in both the adjuvant and metastatic settings (6-9). Trastuzumab, a humanized anti-HER2 antibody, remains the backbone of treatment in the adjuvant and first-line metastatic settings, usually in combination with a taxane. Anti-HER2 therapy in combination with cytotoxic chemotherapy allows for concurrent treatment with agents having two different mechanisms of action, leading to greater efficacy than with either agent alone (6, 10, 11).

TABLE 1

Summary of TGI Indices

| Tumor name | Cancer Type | Type of Xenograft | Vendor | Observed TGI (%) | | | Predicted % TGI |
|---|---|---|---|---|---|---|---|
| | | | | Tucatinib | Trastuzumab | Tucatinib + Trastuzumab | Tucatinib + Trastuzumab |
| Calu-3 | NSCLC | CDX | BioDuro | 63 | 86 | 100 | 95 |
| NCH-H2170 | NSCLC | CDX | In house | 91 | 61 | 98 | 97 |
| CTG-0121 | CRC | PDX | Champions Oncology | 104 | 109 | 124 | 100 |
| CTG-0784 | CRC | PDX | Champions Oncology | 50 | 36 | 103 | 68 |
| CTG-0383 | CRC | PDX | Champions Oncology | 117 | 80 | 137 | 103 |
| CTG-0137 | Esophageal | PDX | Champions Oncology | 49 | 55 | 85 | 77 |
| CTG-0138 | Esophageal | PDX | Champions Oncology | 69 | −34 | 120 | 59 |
| CTG-0927 | Cholangio-carcinoma | PDX | Champions Oncology | 48 | 63 | 86 | 81 |
| GXA-3038 | Gastric carcinoma (Asian) | PDX | Oncotest | 110 | 50 | 116 | 105 |
| GXA-3039 | Gastric carcinoma (Asian) | PDX | Oncotest | 48 | 38 | 103 | 68 |
| GXA-3054 | Gastric carcinoma (Asian) | PDX | Oncotest | 65 | 93 | 136 | 98 |

Example 6: Phase 2 Randomized, Double-Blinded, Controlled Study of Tucatinib Vs. Placebo in Combination with Capecitabine and Trastuzumab in Patients with Pretreated Unresectable Locally Advanced or Metastatic HER2+ Breast Carcinoma This example describes a double-blinded study of tucatinib or placebo in combination with capecitabine and trastuzumab is carried out in patients with unresectable locally advanced or metastatic HER2+ breast cancer who have had prior treatment with trastuzumab, pertuzumab and T-DM1.

Background and Rationale

HER2+ Breast Cancer

Breast cancer is the most common form of cancer in women worldwide (1), and the second leading cause of cancer-related death in the United States (2). Approximately 20% of breast cancers overexpress the human epidermal growth factor receptor 2 (HER2) (3,4). HER2 is a transmembrane tyrosine kinase receptor that mediates cell growth, differentiation, and survival. Tumors that overex- Despite the improvements in outcomes for early stage HER2+ breast cancer, up to a quarter of all patients treated with anti-HER2 therapy in the adjuvant setting relapse. The development of new HER2 targeted therapies such as pertuzumab and T-DM1 (ado-trastuzumab emtansine or trastuzumab emtansine) for metastatic HER2+ breast cancer has led to a meaningful prolongation in the median survival of these patients; however, essentially all patients in the metastatic setting ultimately progress. Treatment failures may result from primary or acquired resistance to HER2 blockade (12-15). There is evidence that dual targeting of HER2, either through combination of 2 different HER2-targeted antibodies or through use of an antibody-based therapy such as trastuzumab and a TKI, can lead to further improvements in efficacy in metastatic disease (8, 16). In particular, combination of a small molecule TKI with an antibody-based therapy may be effective, as it may help overcome resistance to antibody-mediated inhibition through utilization of an alternative mechanism of receptor inhibition. Lapatinib, a dual epidermal growth factor receptor (EGFR)/HER2 oral TKI, has been shown to have increased activity in combination with trastuzumab compared to lapatinib alone, even when given to patients who have previously progressed on prior trastuzumab-based therapy (17,18). Use of lapatinib, however, has been limited by the anti-EGFR/human epidermal growth factor receptor 1 (HER1) activity of the drug, which results in toxicities such as rash, diarrhea, and fatigue. There is therefore a need for a more selective small molecule inhibitor of HER2 that could be combined with other anti-HER2 therapies to improve clinical outcomes.

The current standard of care for patients with HER2+ metastatic disease consists of treatment with pertuzumab plus trastuzumab and a taxane as first-line treatment for metastatic disease, followed by T-DM1 in second line (4,19). Treatment options for patients who progress after treatment with both pertuzumab and T-DM1 remain relatively limited. Patients are generally treated with a continuation of anti-HER2 therapy (in the form of trastuzumab or lapatinib) in combination with cytotoxic chemotherapy, such as capecitabine. Combined HER2 therapy with trastuzumab and lapatinib can also be considered. However, no single regimen is considered the standard of care in this setting and better options for these patients are needed.

Brain Metastases in HER2+ Breast Cancer

Perhaps the greatest unmet medical need in the post-trastuzumab era is treatment and prevention of brain metastases. Recent data suggest that the incidence of first relapse occurring in the brain is increasing in patients who have received trastuzumab-based adjuvant therapy (20), and approximately 30-50% of HER2+ patients with metastatic disease will develop brain metastases (20-22). The increasing prevalence of brain metastases in HER2+ breast cancer patients may be due to several factors. First, HER2+ breast cancer appears to display tropism for the brain. Second, with better control of non-CNS disease, patients may be living longer allowing brain metastases to become more of a critical clinical issue. Finally, the brain may represent a sanctuary site for HER2+ disease as large molecules, such as trastuzumab, do not penetrate the blood-brain barrier (23).

Treatment options for brain metastases are limited. There is no specific systemic treatment regimen approved for brain metastases, and treatment currently relies heavily on the use of local therapies such as whole brain radiation therapy (WBRT), stereotactic radiation (SRS), or surgery. Patients may also receive chemotherapy alone, or capecitabine and either lapatinib or trastuzumab, although brain response rates are generally modest (24, 25). The development of HER2-targeted systemic therapies with clinical benefit in both brain and non-CNS sites of disease could lead to improved clinical outcomes, both by improving overall PFS and OS as well as by avoiding or delaying the use of radiation therapy and its associated toxicities, including neurocognitive impairment.

Study Design

After meeting all eligibility criteria, patients are randomized in a 2:1 ratio to receive tucatinib or placebo in combination with capecitabine and trastuzumab. Approved trastuzumab biosimilars (intravenous or subcutaneous formulations) may also be used in the study as an alternative to trastuzumab.

Randomization of patients for the trial is made using a dynamic hierarchical randomization schema. Rosenberger, William F., and John M. Lachin. "Chapter 7." *Randomization in Clinical Trials Theory and Practice*. Hoboken, N.J.: John Wiley & Sons, 2016. Stratification factors include presence or history of treated or untreated brain metastases (yes/no), Eastern Cooperative Oncology Group Performance Status (ECOG PS) (0 vs. 1), and region of world (US vs Canada vs Rest of World). Stratification for presence of brain metastases is based upon medical history and investigator assessment of screening contrast brain MRI. Patients who have prior brain metastases (treated or untreated) or unequivocal presence of brain metastases on screening MRI are considered a "Yes" for stratification purposes, and subsequent efficacy assessments. Patients with no prior history of brain metastases and lesions of equivocal significance on screening contrast brain MRI are also considered a "Yes" for purposes of stratification and follow-up.

Treatment is administered in cycles of 21 days each. Tucatinib (300 mg) or placebo are given by mouth (PO) twice daily (BID). If necessary, the tucatinib or placebo dose is reduced to 250 mg, 200 mg, or even 150 mg PO BID to avoid side effects.

Capecitabine is given at 1000 mg/m$^2$ PO BID on Days 1-14 of each 21-day cycle.

Trastuzumab is given as a loading dose of 8 mg/kg IV. Following an IV loading dose of trastuzumab, 6 mg/kg of trastuzumab is administered once every 21 days, except in specific circumstances where it may be given weekly to compensate for modifications in treatment schedule. A loading dose of trastuzumab is not given to patients who have received trastuzumab within 4 weeks of the beginning of the trial's first cycle. These patients receive trastuzumab at 6 mg/kg each cycle, including Cycle 1. Trastuzumab may also be given on a weekly basis at 2 mg/kg IV q 7 days, but only in the circumstance that trastuzumab infusion has been delayed, and weekly infusions are required to resynchronize the cycle length to 21 days.

Alternatively, trastuzumab is administered as a subcutaneous dose, given as a fixed dose of 600 mg once every 3 weeks. Subcutaneous trastuzumab does not require a loading dose nor is a weekly schedule available for the intravenous formulation. Patients are permitted to crossover from IV trastuzumab to subcutaneous trastuzumab.

Treatment continues until unacceptable toxicity, disease progression, withdrawal of consent, or study closure. In patients with isolated progression in the brain and stable systemic disease, local therapy to the brain may be administered.

Patients are assessed throughout the study for safety. Safety assessments including physical exam, collection of AEs, and laboratory assessments are performed at a minimum of once every three weeks throughout study treatment and 30 days after the last dose of study drugs. Cardiac ejection fraction is assessed by MUGA scan or ECHO at screening and once every 12 weeks thereafter.

Laboratory assessments include the following tests: calcium, magnesium, inorganic phosphorus, uric acid, total protein, lactate dehydrogenase (LDH), albumin, blood urea nitrogen (BUN), creatinine, bicarbonate, glucose, potassium, chloride, and sodium. Liver function tests (LFT) include the following: AST/SGOT, ALT/SGPT, total bilirubin, and alkaline phosphatase. The hematology panel includes the following tests: complete blood count (CBC) with differential, hemoglobin, hematocrit (Hct), and platelets. The coagulation panel includes the following tests: INR, prothrombin time (PT), and aPTT. The urinalysis includes (but not limited to) the following tests: color, appearance, pH, protein, glucose, ketones, and blood.

Contrast brain MRI is performed at baseline in all patients regardless of prior history of brain metastases. Efficacy assessments include measurement of all known sites of metastatic or locally advanced unresectable disease (including at a minimum the chest, abdomen, and pelvis) by high quality spiral contrast CT, PET/CT (if high quality CT scan included) or MRI scan as appropriate, as well as appropriate imaging of any other known sites of disease (e.g., skin lesion photography, bone imaging) at baseline, every 6 weeks for the first 24 weeks, and then every 9 weeks thereafter. Additional imaging such as nuclear medicine bone scan or other scans may be performed at the discretion of the investigator. Treatment decisions are made based upon investigator assessment of radiologic scans. All patients undergo a repeat contrast MRI of the brain within 30 days of the end of treatment, unless a contrast MRI of the brain has already been performed within 30 days or there is prior documentation of progression in the brain on study. If study treatment is discontinued for reasons other than disease progression, every reasonable effort is made to evaluate and follow patients for progressive disease. All patients in the study continue to be followed for OS after completion of study treatment.

For patients who undergo local therapy to brain metastases incidentally found on screening contrast brain MRI, and then continue onto study treatment, the performance of a repeat contrast MRI after completion of local therapy is as follows: For patients who receive brain radiotherapy during the screening period, the original baseline contrast brain MRI serves as the baseline for comparison for further response assessments. For patients who undergo surgical resection of brain metastases during the screening period, a post-operative contrast brain MRI serves as the baseline.

Pharmacokinetic assessments of peak and trough levels of tucatinib and metabolite drug levels are performed. Blood samples are also taken for possible evaluation of potential biomarkers of response, including circulating tumor DNA (ctDNA). Individual (patient) plasma tucatinib concentrations at each sampling time are listed; corresponding summary statistics at each sampling time are also calculated. Plasma tucatinib vs. time profiles (with concentrations on both a log and linear scale) are plotted for each patient; corresponding summary time plots are likewise constructed. The ratio of the metabolite ONT-993 to the parent drug tucatinib is listed and summarized at each sampling time.

Safety monitoring is performed throughout the study on a blinded basis. All relevant safety and efficacy data including (but not limited to) deaths, discontinuations, dose reductions, AEs, serious adverse events (SAEs), and cases of progressive disease within 6 weeks of study entry (blinded and unblinded) are regularly reviewed.

Health-related quality of life and health care economics are assessed by use of the EQ-5D-5L quality of life instrument and collection of health care resource utilization data.

The primary efficacy endpoint is progression-free survival (PFS), defined as the time from randomization to centrally-reviewed documented disease progression or death from any cause, whichever occurs earlier. For the primary endpoint of centrally-reviewed PFS in the study as a whole, the two treatment groups are compared using a log-rank test. The p-value for this test is calculated using a rerandomization procedure to reflect the dynamic allocation used in randomization: known history of treated or untreated brain metastases (yes/no); ECOG PS (0 vs. 1); and region of world. All randomized patients are included in the primary analysis. Patients are treated as censored at the time of their last assessment for progression.

Secondary efficacy endpoints are progression-free survival in patients with brain metastases, duration of overall survival, objective response rate, clinical benefit rate, and duration of response (for responsive patients).

Exploratory efficacy evaluations are also performed using the bi-compartmental tumor assessment method. In this analysis, progression (independent central review) with non-CNS disease is evaluated per the Response Evaluation Criteria In Solid Tumors (RECIST) 1.1 criteria and CNS disease is evaluated per the Response Assessment in NeuroOncology—Brain Metastases (RANO-BM) criteria. HER2 and other mutations are explored as possible biomarkers of response though the use of descriptive subgroup analyses of the primary and secondary endpoints.

Follow-up for PFS continues for 12 months after the last patient is randomized. Follow-up for OS continues until a sufficient number of events have been recorded to have 90% power to test the effect of treatment on OS. As the median survival for the control arm may range from 15 to 24 months, the primary analysis for OS takes place approximately 1-2+ years after the primary analysis of PFS.

Endpoints

Primary Endpoint

PFS, defined as the time from randomization to independent centrally-reviewed documented disease progression (per RECIST 1.1), or death from any cause, whichever occurs first.

Secondary Endpoints

Efficacy endpoints include: PFS in patients with brain metastases at baseline using RECIST 1.1 based on independent central review; OS; PFS, defined as the time from randomization to investigator-assessed documented disease progression (per RECIST 1.1), or death from any cause, whichever occurs first; ORR (RECIST 1.1) based on independent central review; DOR (RECIST 1.1) based on independent central review; CBR (RECIST 1.1) based on independent central review; and comparative health economics of tucatinib vs. placebo.

Safety endpoints include: adverse events (AEs); clinical laboratory assessments; vital signs and other relevant safety variables; frequency of dose holding, dose reductions, and discontinuations of capecitabine; frequency of dose holding, dose reductions, and discontinuations of tucatinib; and frequency of dose holding and discontinuations of trastuzumab.

Pharmacokinetics endpoints include plasma concentrations of tucatinib and metabolites.

Health economics and outcome endpoints include: cumulative incidence of health resource utilization, including, but not limited to, procedure time, length of stay, hospitalizations, ED visits, planned and unplanned provider visits, medication use, radiology, and other treatments and procedures; and health-related quality of life/health status using the EQ-5D-5L instrument.

Exploratory Endpoints

Exploratory endpoints include: PFS (per RANO-BM using the bi-compartmental tumor assessment method (non-brain disease being evaluated per RECIST 1.1 and CNS disease being evaluated per RANO-BM)); non-CNS PFS per RECIST 1.1 in patients who continue on study treatment for clinical benefit following development of and local treatment for first CNS progression; ORR (using bi-compartmental tumor assessment method per RANO-BM by independent central review); duration of response (per RANO-BM bi-compartmental tumor assessment method by independent central review); time to brain progression (per RANO-BM by independent central review); CBR (per RANO-BM bi-compartmental tumor assessment method by independent central review); presence of HER2 mutations or other mutations as potential biomarkers of response; and time to intervention (surgery or radiation) for brain metastases.

Selection and Withdrawal of Patients
Inclusion Criteria

In order to be eligible for the study, patients must meet the criteria described below.

(1) Patients must have histologically confirmed HER2+ breast carcinoma, with HER2+ defined by ISH or FISH or IHC methodology. Tissue blocks or slides must be submitted to confirm HER2 positivity (using ISH or FISH) by a sponsor-designated central laboratory prior to randomization. Centrally confirmed HER2 results (either IHC, ISH, or FISH) from a previous study can be used to determine eligibility for this study with approval from the sponsor.

(2) Patients must have received previous treatment with trastuzumab, pertuzumab, and T-DM1.

(3) Patients must have progression of unresectable locally advanced or metastatic breast cancer after last systemic therapy (as confirmed by investigator), or be intolerant of last systemic therapy.

(4) Patients must have measurable or non-measureable disease assessable by RECIST 1.1.

(5) Patients must be at least 18 years of age at time of consent.

(6) Patients must have ECOG PS 0 or 1.

(7) Patients must have a life expectancy of at least 6 months, in the opinion of the investigator.

(8) Patients must have adequate hepatic function as defined by a total bilirubin ≤1.5×ULN, except for patients with known Gilbert's disease, who may enroll if the conjugated bilirubin is ≤1.5×ULN; and transaminases AST/SGOT and ALT/SGPT≤2.5×ULN (≤5×ULN if liver metastases are present).

(9) Patients must have adequate baseline hematologic parameters as defined by ANC≥1.5×10$^3$/μL; platelet count ≥100×10$^3$/μL (patients with stable platelet count from 75-100×10$^3$/μL may be included with approval from medical monitor); hemoglobin ≥9 g/dL; and in patients transfused before study entry, transfusion must be ≥14 days prior to start of therapy to establish adequate hematologic parameters independent from transfusion support.

(10) Patients must have creatinine clearance ≥50 mL/min as calculated per institutional guidelines or, in patients ≤45 kg in weight, serum creatinine within institutional normal limits.

(11) Patients must have INR and aPTT≤1.5×ULN unless on medication known to alter INR and aPTT. Patient use of warfarin and other coumarin derivatives are prohibited.

(12) Patients must have LVEF≥50% as assessed by ECHO or MUGA scan documented within 4 weeks prior to first dose of study treatment.

(13) If a patient is a female of childbearing potential, the patient must have a negative result of a serum pregnancy test performed within 7 days prior to first dose of study treatment. A woman is considered of childbearing potential (i.e., fertile) following menarche and until becoming post-menopausal unless permanently sterile. Permanent sterilization methods include hysterectomy, bilateral salpingectomy, and bilateral oophorectomy. A postmenopausal state is defined as no menses for 12 months without an alternative medical cause.

(14) Women of childbearing potential (as defined above) and men with partners of childbearing potential agree to use a highly effective birth control method, i.e., methods that achieve a failure rate of less than 1% per year when used consistently and correctly. Such methods include: combined (estrogen and progestogen containing) hormonal contraception associated with inhibition of ovulation (oral, intravaginal, or transdermal); progestogen-only hormonal contraception associated with inhibition of ovulation (oral, injectable, or implantable); intrauterine device; intrauterine hormone-releasing system; bilateral tubal occlusion/ligation; vasectomized partner; or sexual abstinence. Male patients with partners of childbearing potential must use barrier contraception. All study patients are instructed to practice effective contraception, as described above, starting from the signing of informed consent until 7 months after the last dose of study medication or investigational medicinal product.

(15) Patients must provide signed informed consent per a consent document that has been approved by an IRB/IEC prior to initiation of any study-related tests or procedures that are not part of standard-of-care for the patient's disease.

(16) Patients must be willing and able to comply with study procedures.

(17) For CNS inclusion, based on screening contrast brain MRI, patients must have one of the criteria described: (i) no evidence of brain metastases; (ii) untreated brain metastases not needing immediate local therapy (for patients with untreated CNS lesions >2.0 cm on screening contrast brain MRI, discussion with and approval from the medical monitor is required prior to enrollment); or (iii) has previously treated brain metastases.

Brain metastases previously treated with local therapy may either be stable since treatment or may have progressed since prior local CNS therapy, provided that there is no clinical indication for immediate re-treatment with local therapy in the opinion of the investigator.

Patients treated with CNS local therapy for newly identified lesions found on contrast brain MRI performed during screening for this study may be eligible to enroll if all of the following criteria are met: time since WBRT is ≥21 days prior to first dose of treatment, time since SRS is ≥7 days prior to first dose of treatment, or time since surgical resection is ≥28 days; and other sites of evaluable disease are present.

Relevant records of any CNS treatment must be available to allow for classification of target and non-target lesions.

Exclusion Criteria

Patients are excluded from the study for any of the reasons described below.

(1) Patient has previously been treated with lapatinib within 12 months of starting study treatment (except in cases where lapatinib was given for ≤21 days and was discontinued for reasons other than disease progression or severe toxicity); or neratinib, afatinib, or other investigational HER2/EGFR or HER2 TKI at any time previously.

(2) Patient has previously been treated with capecitabine for metastatic disease (except in cases where capecitabine was given for ≤21 days and was discontinued for reasons other than disease progression or severe toxicity). Patients who have received capecitabine for adjuvant or neoadjuvant treatment at least 12 months prior to starting study treatment are eligible.

(3) Patient has a history of exposure to the following cumulative doses of anthracyclines: doxorubicin (>360 mg/m$^2$), epirubicin (>720 mg/m$^2$), mitoxantrone (>120 mg/m$^2$), idarubicin (>90 mg/m$^2$), or liposomal doxorubicin (e.g. Doxil, Caelyx, Myocet)>550 mg/m$^2$).

(4) Patient has a history of allergic reactions to trastuzumab, capecitabine, or compounds chemically or biologically similar to tucatinib, except for Grade 1 or 2 infusion related reactions to trastuzumab that were successfully managed, or known allergy to one of the excipients in the study drugs.

(5) Patient has received treatment with any systemic anti-cancer therapy (including hormonal therapy), non-CNS radiation, or experimental agent ≤3 weeks of first dose of study treatment or are currently participating in another interventional clinical trial. An exception for the washout of hormonal therapies is GnRH agonists used for ovarian suppression in premenopausal women, which are permitted concomitant medications.

(6) Patient has any toxicity related to prior cancer therapies that has not resolved to ≤Grade 1, with the following exceptions: alopecia and neuropathy (which must have resolved to ≤Grade 2); and CHF (which must have been ≤Grade 1 in severity at the time of occurrence, and must have resolved completely).

(7) Patient has clinically significant cardiopulmonary disease such as: ventricular arrhythmia requiring therapy; uncontrolled hypertension (defined as persistent systolic blood pressure >150 mm Hg and/or diastolic blood pressure >100 mm Hg on antihypertensive medications); any history of symptomatic CHF; severe dyspnea at rest (CTCAE Grade 3 or above) due to complications of advanced malignancy or hypoxia requiring supplementary oxygen therapy; or conditions potentially resulting in drug-induced prolongation of the QT interval or torsade de pointes, such as congenital or acquired long QT syndrome a family history of sudden death, a history of previous drug induced QT prolongation, or a current use of medications with known and accepted associated risk of QT prolongation (see row "Accepted Association" in Table 13 below).

(8) Patient has had a known myocardial infarction or unstable angina within 6 months prior to first dose of study treatment.

(9) Patient is a known carrier of Hepatitis B or Hepatitis C or have other known chronic liver disease.

(10) Patient is known to be positive for HIV.

(11) Patient is pregnant, breastfeeding, or planning a pregnancy.

(12) Patient requires therapy with warfarin or other coumarin derivatives (non-coumarin anticoagulants are allowed).

(13) Patient has an inability to swallow pills or significant gastrointestinal disease which would preclude the adequate oral absorption of medications.

(14) Patient has used a strong CYP3A4 inducer or inhibitor, or strong CYP2C8 inducer or inhibitor within 3 elimination half-lives of the inhibitor or inducer prior to first dose of study treatment (see Tables 10 and 11 at the end of this example).

(15) Patient has a known dihydropyrimidine dehydrogenase deficiency.

(16) Patient is unable for any reason to undergo contrast MRI of the brain.

(17) Patient has any other medical, social, or psychosocial factors that, in the opinion of the investigator, could impact safety or compliance with study procedures.

(18) Patient has evidence within 2 years of the start of study treatment of another malignancy that required systemic treatment.

For CNS exclusion, based on screening brain MRI, patients must not have any of the following criteria.

(19) Patient may not have any untreated brain lesions >2.0 cm in size, unless discussed with medical monitor and approval for enrollment is given.

(20) Patient may not have ongoing use of systemic corticosteroids for control of symptoms of brain metastases at a total daily dose of >2 mg of dexamethasone (or equivalent). However, patients on a chronic stable dose of ≤2 mg total daily of dexamethasone (or equivalent) may be eligible with discussion and approval by the medical monitor.

(21) Patient may not have any brain lesion thought to require immediate local therapy, including, but not limited to, a lesion in an anatomic site where an increase in size or possible treatment-related edema may pose risk to patient (e.g., brain stem lesions). Patients who undergo local treatment for such lesions identified by screening contrast brain MRI may still be eligible for the study based on criteria described under CNS inclusion criteria described above.

(22) Patient may not have known or concurrent LMD as documented by the investigator.

(23) Patient may not have poorly controlled (>1/week) generalized or complex partial seizures, or manifest neurologic progression due to brain metastases notwithstanding CNS-directed therapy.

Criteria for Discontinuation of Study Treatment

Subjects who discontinue from the study are not replaced. Reasons for patient withdrawal from study treatment may be due to any of the following: AE, progressive disease, death, withdrawal of consent, loss to follow-up, physician decision due to clinical progression, physician decision (due to other factors), patient decision, protocol violation, study termination by sponsor, pregnancy or patient begins breast-feeding while on trial, or other criteria as appropriate.

The reason for withdrawal from study treatment must be recorded in the patient's eCRF. Evaluations scheduled for the 30-Day Follow-up Visit and Long-Term Follow-up Visits are completed, unless the patient withdraws consent from the study. Patients are also followed for progressive disease at least until a confirmed PFS event has been observed. If an AE is the cause for withdrawal from study treatment, then "Adverse Event" is recorded as the reason for treatment discontinuation rather than physician decision or patient decision. Treatment discontinuation due to AE is noted any time that a patient has an AE such that the patient may not re-start tucatinib, either due to investigator discretion or due the requirements of dose modification described below (e.g., requiring dose reduction to <150 mg BID tucatinib, holding tucatinib >6 weeks due to toxicity, or lack of resolution of AE to a sufficient grade to re-start tucatinib). Patients who discontinue tucatinib or placebo or both capecitabine and trastuzumab are recorded as an "adverse event" for the reason for treatment discontinuation if AE led to discontinuation of study drugs.

Because the primary study endpoint is defined as PFS as determined by central radiologic assessment, every effort is made to confirm disease progression radiographically whenever possible. However, in instances where patients appear to have progressive symptoms and signs of metastatic breast cancer for whom it is not possible or feasible to undergo radiologic assessment, investigators may remove the patient from study treatment due to "physician decision due to clinical progression." These patients are censored in the final analysis of the primary endpoint, so use of this reason for removing such patients from study treatment is restricted to those cases in which it is not clinically appropriate for the patient to undergo further radiologic assessment and where there is clinical confidence for cancer progression in the absence of radiographic confirmation. Special consideration is given to ensure that other possible reasons, particularly AEs, are not a more accurate description of the reason for study drug discontinuation in these cases.

Long-term follow-up after discontinuation of study treatment continues until patient withdrawal from the study. Reasons for patient withdrawal from the study may be due to any of the following: death, withdrawal of consent for follow-up, loss to follow-up, physician decision, study termination by sponsor, or other reason as appropriate.

Dose Modifications

Tables 2-7 provide dose modification guidance for tucatinib or placebo, capecitabine, and trastuzumab.

All AEs and laboratory abnormalities are assessed by the investigator for relationship to tucatinib or placebo, capecitabine, and trastuzumab, as applicable. An AE may be considered related to tucatinib or placebo alone, capecitabine alone, trastuzumab alone, 2 of the 3 drugs, all 3 drugs, or to none. In the event that the relationship is unclear, discussion is held with the medical monitor to discuss which study drug(s) is held and/or modified. Dosing is modified (including holding the dose, dose reduction, or discontinuation of drug) as described below.

Any study drug is discontinued if a delay of that drug greater than 6 weeks is required due to treatment-related toxicity, unless a longer delay is approved by the medical monitor. Patients who discontinue tucatinib or placebo discontinue study treatment.

Patients may discontinue either capecitabine or trastuzumab due to toxicity, and continue on tucatinib or placebo in combination with either capecitabine or trastuzumab, as applicable. If both capecitabine and trastuzumab are discontinued, patients also discontinue tucatinib or placebo study treatment.

Protocol defined visits continue as planned during a 21-day cycle even during dose holds or delays.

Capecitabine is only taken on Days 1 to 14 of a cycle. No doses are given on Day 15 through Day 21 of a cycle.

Dose reductions or treatment interruption for reasons other than those described below may be made by the investigator if it is deemed in the best interest of patient safety.

Doses held for toxicity are not replaced.

Study treatment may be held up to 6 weeks to allow local CNS therapy. Oral study drugs (tucatinib/placebo and capecitabine) are to be held 1 week prior to planned CNS-directed therapy. If necessary, tucatinib may be held prior to CNS-directed radiotherapy. Capecitabine is a known radiation sensitizer and therefore needs to be held prior to CNS-directed radiotherapy. Trastuzumab has been shown not to potentiate radiation and therefore may continue as per protocol schedule during radiotherapy. Oral study drugs may be re-initiated 7 days or more after completion of SRS/SRT, 21-days or more after WBRT and 28-days or more after surgical resection. Plans for holding and re-initiating study drugs before and after local therapy require discussion with, and documented approval from, the medical monitor.

Tucatinib or Placebo Dose Reductions

Tables 2-7 provide the tucatinib or placebo dose modification requirements. Dose reductions larger than those required by these tables may be made at the discretion of the investigator. Up to 3 dose reductions of tucatinib or placebo are allowed, but dose reductions to below 150 mg BID are not allowed. Patients who, in the opinion of the investigator, would require a dose reduction to <150 mg BID, or who would require a potential fourth dose reduction of tucatinib, discontinue study treatment.

Tucatinib or placebo dose is not re-escalated after a dose reduction is made.

TABLE 2

Recommended Tucatinib or Placebo Dose Reduction Schedule

| Starting Dose[a] | 1st Dose Reduction | 2nd Dose Reduction | 3rd Dose Reduction |
| --- | --- | --- | --- |
| 300 mg PO BID | 250 mg PO BID | 200 mg PO BID | 150 mg PO BID |

[a]Dose reductions of greater steps than those listed in this table (i.e. more than 50 mg per dose reduction) may be made if considered clinically appropriate by the investigator. However, tucatinib or placebo may not be dose-reduced below 150 mg BID.

Trastuzumab Dose Modifications

There are no dose reductions for trastuzumab. Trastuzumab may also be given on a weekly basis at 2 mg/kg IV q 7 days, but only in the circumstance that trastuzumab infusion has been delayed, and weekly infusions are required to resynchronize the cycle length to 21 days, after discussion with the medical monitor. The subcutaneous dose of trastuzumab (600 mg) cannot be modified as it is administered only once every 3 weeks. If trastuzumab cannot be restarted at the same dose after being held for an AE, it must be discontinued. As trastuzumab is given as an IV infusion, infusion-associated reactions (IARs), may occur.

If a significant IAR occurs, the infusion is interrupted and appropriate medical therapies are administered (see below). Permanent discontinuation is considered in patients with severe IAR. This clinical assessment is based on the severity of the preceding reaction and response to administered treatment for the adverse reaction.

If patients develop an IAR, patients are treated according to the following guidelines, or according to institutional guidelines, at discretion of the investigator: stop infusion and notify physician; assess vital signs; administer acetaminophen 650 mg PO; consider administration of meperidine 50 mg IM, diphenhydramine 50 mg IV, ranitidine 50 mg IV or cimetidine 300 mg IV, dexamethasone 10 mg IV, or famotidine 20 mg IV; and if vital signs stable, resume trastuzumab infusion.

No standard premedication is required for future treatments if patients have developed an infusion syndrome. Patients may be given acetaminophen prior to treatments. Serious reactions have been treated with supportive therapy such as oxygen, beta-agonists, corticosteroids and withdrawal of study agent as indicated.

TABLE 3

Dose Modifications of Tucatinib or Placebo and Trastuzumab for Clinical Adverse Events Other Than Left Ventricular Dysfunction Related to Either Tucatinib or Placebo and/or Trastuzumab, or Hepatocellular Toxicity*

| Clinical Adverse Event | Tucatinib or Placebo | Trastuzumab |
| --- | --- | --- |
|  | Related to tucatinib or Placebo | Related to Trastuzumab |
| ≥Grade 3 AEs other than Grade 3 fatigue lasting ≤3 days; alopecia[a], nausea; vomiting; diarrhea; rash; correctable electrolyte abnormalities which return to ≤Grade 1 within 7 days. | Hold until severity ≤ Grade 1 or pretreatment level, Restart at next lowest dose level. | Do not administer until severity ≤ Grade 1 or pretreatment level. Restart without dose reduction. |

TABLE 3-continued

Dose Modifications of Tucatinib or Placebo and Trastuzumab for Clinical Adverse Events Other Than Left Ventricular Dysfunction Related to Either Tucatinib or Placebo and/or Trastuzumab, or Hepatocellular Toxicity*

| | Tucatinib or Placebo | Trastuzumab |
|---|---|---|
| Grade 3 nausea, vomiting, or diarrhea WITHOUT optimal use of anti-emetics or anti-diarrheals. | Hold until severity ≤ Grade 1 or pretreatment level. Initiate appropriate therapy. Restart without dose reduction. | Do not administer until severity ≤ Grade 1 or pretreatment level. Initiate appropriate therapy. Restart without dose reduction. |
| Grade 3 nausea, vomiting, or diarrhea WITH optimal use of anti-emetics or anti-diarrheals. | Hold until severity ≤ Grade 1 or pretreatment level. Restart at next lowest dose level. | Do not administer until severity ≤ Grade 1 or pretreatment level. Restart without dose reduction. |
| Grade 4 nausea, vomiting, or diarrhea regardless of use of anti-emetics or anti-diarrheals. | Do not administer until severity ≤ Grade 1. Reduce to next lowest dose level. | Do not administer until severity ≤ Grade 1. Restart without dose reduction. |
| Grade 3 rash WITHOUT optimal use of topical corticosteroids or anti-infectives. | Hold until severity ≤ Grade 1 or pretreatment level. Initiate appropriate therapy. Restart without dose reduction. | Do not administer until severity ≤ Grade 1 or pretreatment level. Initiate appropriate therapy. Restart without dose reduction. |
| Grade 3 rash WITH optimal use of topical corticosteroids or anti-infectives. | Hold until severity ≤ Grade 1 or pretreatment level. Restart at next lowest dose level. | Do not administer until severity ≤ Grade 1 or pretreatment level. Restart without dose reduction. |
| Grade 4 rash regardless of use of topical corticosteroids or anti-infectives. | Hold until severity ≤ Grade 1 or pretreatment level. Restart at next lowest dose level. | Do not administer until severity ≤ Grade 1 or pretreatment level. Restart without dose reductions. |

[a]No dose modifications are required for alopecia
*Note that if the AE in question does not recover to the Grade required for restarting study medication as outlined in the table, the patient may need to discontinue the drug completely. Patients requiring a hold of tucatinib for >6 weeks must discontinue study treatment, unless a longer delay is approved by the medical monitor.

Capecitabine Dose Modifications

Capecitabine doses are modified as described below in Table 4.

Capecitabine is held for any patient who experiences a Grade 2 or greater AE considered related to capecitabine or to the combination of tucatinib or placebo and capecitabine and/or trastuzumab (as determined by the investigator).

The capecitabine dose is not re-escalated after a dose reduction is made.

TABLE 4

Dose Modification of Capecitabine for Clinical Adverse Events Considered Related to Capecitabine

| CTCAE Toxicity Grades | During a Course of Therapy | Dose Adjustment for Next Treatment (% of Starting Dose)[a] |
|---|---|---|
| Grade 1 | Maintain dose level. | Maintain dose level. |
| Grade 2[b] | | |
| 1st appearance | Interrupt until resolved to Grade ≤ 1. | 100% |
| 2nd appearance | Interrupt until resolved to Grade ≤ 1. | 75% |
| 3rd appearance | Interrupt until resolved to Grade ≤ 1. | 50% |
| 4th appearance | Discontinue permanently. | NA |
| Grade 3 | | |
| 1st appearance | Interrupt until resolved to Grade ≤ 1. | 75% |
| 2nd appearance | Interrupt until resolved to Grade ≤ 1. | 50% |
| 3rd appearance | Discontinue permanently. | NA |
| Grade 4 | | |
| 1st appearance | Discontinue permanently. | |

Abbreviations: Common Terminology Criteria for Adverse Events (CTCAE); not applicable (NA).
[a]Dose modification table is based upon XELODA ® package insert; dose rounding is performed per institutional guidelines
[b]In certain instances of asymptomatic or mildly symptomatic Grade 2 laboratory abnormalities (for example, anemia), investigators may choose to maintain capecitabine dose level and/or to resume capecitabine prior to resolution to Grade 1. This is done only when the risk to patient from capecitabine dose interruption and/or reduction outweighs the risk to the patient from the adverse event, and when the action is consistent with usual and customary clinical practice. If an investigator wishes to follow an alternative dose modification schedule of capecitabine in these circumstances, approval from medical monitor is required.

Dose Modifications for Hepatotoxicity

Dose modification may be required in the case of liver function abnormalities. For dose modifications of tucatinib or placebo and capecitabine, see Table 5 below. Dose modification of trastuzumab is not required but dosing can be held at investigator discretion.

TABLE 5

Dose Modifications of Tucatinib or Placebo and Capecitabine for Liver Function Abnormalities

| Liver Function Abnormalities | Action for tucatinib or placebo, Regardless of Relationship to Drug | Capecitabine |
|---|---|---|
| Grade 2 elevation of ALT and/or AST (>3-≤5 × ULN) | Dose modification not required | If abnormalities are considered related to capecitabine, modifications are made as per Table 4. If abnormalities are not considered related to capecitabine, modifications are not mandated but may be made at the discretion of the investigator. |
| Grade 3 elevation of ALT and/or AST (>5-20 × ULN) | Hold until severity ≤ Grade 1 Restart at next lowest dose level | |
| Grade 4 elevation of ALT and/or AST (>20 × ULN) | Discontinue drug | |
| Elevation of ALT and/or AST (>3 × ULN) AND Bilirubin (>2 × ULN) | Discontinue drug | |
| Grade 2 elevation of bilirubin (>1.5-3 × ULN) AND both ALT and AST (<3 × ULN) | Hold until severity ≤ Grade 1 Restart at same dose level | |
| Grade 3 elevation of bilirubin (>3-≤10 × ULN) AND both ALT and AST (<3 × ULN) | Hold until severity ≤ Grade 1 Restart at next lowest dose level | |
| Grade 4 elevation of bilirubin (>10 × ULN) | Discontinue drug | |

Abbreviations: alanine aminotransferase (ALT); aspartate aminotransferase (AST); upper limit of normal (ULN).

Dose Modifications for Left Ventricular Dysfunction

Tucatinib or placebo and trastuzumab dose modification guidelines for left ventricular dysfunction are provided in Table 6.

TABLE 6

Dose Modifications for Left Ventricular Dysfunction

| | Symptomatic CHF | LVEF < 40% | LVEF below institutional limits of normal and ≥10% points below pretreatment baseline, or ≥16% absolute decrease from pretreatment baseline | LVEF 40% to ≤45% and decrease is <10% points from baseline | LVEF > 45% |
|---|---|---|---|---|---|
| | Discontinue tucatinib, placebo, and trastuzumab. | Do not administer tucatinib, placebo or trastuzumab. Repeat LVEF assessment within 4 weeks. If LVEF < 40% is confirmed, discontinue tucatinib, placebo, and trastuzumab. | Do not administer tucatinib, placebo or trastuzumab. Repeat LVEF assessment within 4 weeks. If the LVEF has not recovered to within normal limits and within 15% points from baseline, discontinue tucatinib, placebo, and trastuzumab, as applicable. | Continue treatment with tucatinib or placebo and trastuzumab. Repeat LVEF assessment within 4 weeks. | Continue treatment with tucatinib or placebo and trastuzumab. |

Abbreviations: Congestive Heart Failure (CHF); Left Ventricular Ejection Fraction (LVEF).

Permanently discontinue tucatinib or placebo and trastuzumab for persistent (i.e., >4 weeks) LVEF decline or for suspension of dosing on >3 occasions for LVEF decline.

Dose Modifications for Prolongation of the QTc Interval

Tucatinib or placebo dose modification guidelines for prolongation of the QTc interval are provided in Table 7.

TABLE 7

Dose Modifications of Tucatinib or Placebo for Prolongation of QTc Interval, Regardless of Relationship to Drug

| Occurrence | Grade 1 QTc 450-480 ms | Grade 2 QTc 481-500 ms | Grade 3 QTc > 501 ms on at least 2 separate ECGs | Grade 4 QTc > 501 ms or >60 ms change from baseline and Torsade de pointes or polymorphic ventricular tachycardia or signs and symptoms of serious arrhythmia |
|---|---|---|---|---|
| 1st occurrence | None | Hold until severity ≤ Grade 1. Restart without dose reduction. | Hold until severity ≤ Grade 1. Restart at next lowest dose level. | Discontinue tucatinib/placebo. |
| 2nd occurrence | None | Hold until severity ≤ Grade 1. Restart at next lowest dose level. | Hold until severity ≤ Grade 1. Restart at next lowest dose level. | NA |
| 3rd occurrence | None | Hold until severity ≤ Grade 1. Restart at next lowest dose level. | Discontinue tucatinib/placebo. | NA |
| 4th occurrence | None | Discontinue tucatinib/placebo. | NA | NA |

Safety Assessments

Safety assessments consist of monitoring and recording AEs and SAEs; physical examination and vital signs; and measurement of protocol-specified clinical laboratory tests, ECG, and either ECHO or MUGA scans deemed critical to the safety evaluation of the study drug(s). Clinically significant changes in these parameters may be captured as AEs.

The investigator is responsible for the appropriate medical care and the safety of patients who have entered this study. The investigator must document all AEs and notify the sponsor of any SAE experienced by patients who have entered this study.

Data Monitoring Committee

The independent DMC is responsible for monitoring the safety of patients in the study at regular intervals. The DMC will look at blinded and unblinded data including deaths, discontinuations, dose reductions, AEs, and SAEs on a regular basis. The DMC makes recommendations to the sponsor regarding the conduct of the study, including study continuation as planned or with protocol amendment, or early discontinuation of the study for excessive toxicity. A separate DMC Charter outlines the committee's composition, members' roles and responsibilities, and describe DMC procedures. The sponsor provides a copy of each DMC recommendation to the investigators.

Clinical Laboratory Evaluation

All safety labs are analyzed by the site's local laboratory (ies). A central laboratory is used for confirmatory HER2 testing during pre-screening and screening.

The chemistry panel includes the following tests: calcium, magnesium, inorganic phosphorus, uric acid, total protein, lactate dehydrogenase (LDH), albumin, blood urea nitrogen (BUN), creatinine, bicarbonate, glucose, potassium, chloride, and sodium.

Liver function tests (LFT) include the following: AST/SGOT, ALT/SGPT, total bilirubin, and alkaline phosphatase.

The hematology panel includes the following tests: complete blood count (CBC) with differential, hemoglobin, hematocrit (Hct), and platelets.

The coagulation panel includes the following tests: INR, prothrombin time (PT), and aPTT.

The urinalysis includes, but is not limited to, the following tests: color, appearance, pH, protein, glucose, ketones, and blood.

Safety Plan for Cardiotoxicity

Trastuzumab and other HER2-targeted therapies are known to increase the risk of the development of asymptomatic and symptomatic declines in LVEF. There have been rare reports of asymptomatic cardiac failure in patients taking tucatinib in combination with trastuzumab alone or with capecitabine. Cardiac function is therefore monitored closely.

Patients are closely monitored throughout the study for the occurrence of any other expected and/or unexpected toxicities. Assessment of cardiac ejection fraction is performed by MUGA or ECHO at screening and once every 12 weeks thereafter until study discontinuation, and 30 days after the last treatment dose (unless done within 12 weeks prior to 30-day follow-up visit).

The risk of QTc prolongation with tucatinib is not yet fully known. Tucatinib must be administered with caution in patients with conditions which may prolong QTc. These conditions include patients with uncorrected hypokalemia or hypomagnesemia and medications with an accepted or possible association with prolongation of the QTc interval or induction of torsade de pointes (see, Table 13 at the end of this example). Excluded from the study are patients with congenital or acquired long QT syndrome, family history of sudden death, a history of previous drug induced QT prolongation and current use of medications with a known and accepted association with QT prolongation (see, Table 13 at the end of this example).

Safety Plan for Hepatotoxicity

While not among the most common adverse reactions reported in patients taking tucatinib, Grade 3 and 4 elevation of LFTs have been seen in some patients on tucatinib studies. Monitoring of liver function tests is required for any patient taking tucatinib.

Because of the known risk of elevation of liver enzymes with tucatinib, patients have LFTs (ALT, AST, total bilirubin, alkaline phosphatase) monitored closely. Tucatinib is held according to protocol if liver functions tests are elevated, and monitored for normalization to the appropriate level per protocol before restarting study drugs.

The identification of liver enzyme abnormalities as potential adverse reactions to tucatinib does not impact upon the anticipated favorable benefit-risk profile of tucatinib, and is thus far in line with the types and severity of AEs that may be seen with other cancer therapies for patients with metastatic breast cancer.

Safety Plan for Patients with Brain Metastases

Patients with brain metastases are at risk for occurrence of AEs due to the presence of CNS lesions, progression of disease and toxicities potentially related to study treatment. On occasion, treatment of brain metastases with systemic or radiation therapy has been associated with localized edema thought to be due to treatment effect and not tumor progression. A patient in study ONT-380-005 with known brain metastases was found to have cerebral edema in an area surrounding a known metastasis in the thalamus shortly after starting treatment with tucatinib, capecitabine and trastuzumab. The patient's symptoms responded rapidly and completely to systemic corticosteroids. It was not known if this patient's symptoms were due to local progression or treatment-related toxicity. Similarly, a patient treated with tucatinib and trastuzumab alone experienced enlargement of a previously irradiated CNS lesion during study treatment. The patient was taken for surgical resection, and found to have no viable tumor. The resected lesion was thought to represent treatment-related necrosis.

In order to minimize the risk of symptomatic cerebral edema in patients with brain metastases in this study, patients with high-risk metastases, including those requiring immediate local therapy, those with rapidly progressing lesions, those requiring corticosteroids at the start of the study (>2 mg of dexamethasone or equivalent per day) for control of CNS symptoms, and those with larger untreated lesions, are excluded from the trial. However, if these patients are amenable to immediate CNS-directed therapy with either surgery or radiation, they may undergo local therapy and then be eligible for the trial. Under select circumstances patients may receive corticosteroid therapy for acute management of symptomatic local edema, as long as contrast brain MRI does not show clear evidence of CNS progression. All such instances require approval from the study medical monitor.

Safety Plan for Prevention of Pregnancy

Due to the potential effect on embryo-fetal development, all study patients must practice an effective method of contraception, as described above, starting from the signing of informed consent until 7 months after the last dose of study medication or investigational medicinal product. Women of childbearing potential (i.e., women who have not undergone surgical sterilization with a hysterectomy, bilateral salpingectomy, and/or bilateral oophorectomy; and are not postmenopausal, as defined as ≥12 months of amenorrhea) must have a negative pregnancy test before beginning the trial and must practice an effective method of contraception during the trial. Effective methods of contraception include combined (estrogen and progestogen containing) hormonal contraception associated with inhibition of ovulation (oral, intravaginal, or transdermal); progestogen-only hormonal contraception associated with inhibition of ovulation (oral, injectable, or implantable); intrauterine device; intrauterine hormone-releasing system; bilateral tubal occlusion/ligation; vasectomized partner; or sexual abstinence. Male patients with partners of childbearing potential must use barrier contraception.

Patients of child-bearing potential are to have urine pregnancy tests performed on Day 1 of each treatment cycle.

Adverse Events

Definitions

An "adverse event (AE)" is defined as any untoward medical occurrence in a patient or clinical investigation patient administered a pharmaceutical product and which does not necessarily have to have a causal relationship with the treatment methods described herein.

An AE can therefore be any unfavorable and unintended sign (e.g., an abnormal laboratory finding), symptom or disease temporally associated with the use of a medicinal product, whether or not considered related to the medicinal product (International Conference on Harmonisation (ICH) E2A guideline; Definitions and Standards for Expedited Reporting; 21 CFR 312.32 IND Safety Reporting).

The factors below are considered when determining whether or not to record a test result or medical condition as an AE.

Any new undesirable medical occurrence or unfavorable or unintended change of a pre-existing condition that occurs during or after treatment with study drugs is recorded as an AE.

Complications that occur as a result of protocol-mandated interventions (e.g., invasive procedures such as biopsies) are recorded as an AE.

Elective procedures or routinely scheduled treatment are not considered AEs. However, an untoward medical event occurring during the pre-scheduled elective procedure is recorded as an AE.

Baseline conditions are not considered AEs unless the condition worsens following study drug administration. Any change assessed as clinically significant worsening of the disease from baseline must be documented as an AE. Baseline conditions present prior to consent are recorded as medical history.

Clinically significant laboratory abnormalities or vital signs (e.g., requiring intervention, meeting serious criteria, resulting in study termination or interruption of study treatment, or associated with signs and symptoms) are recorded as AEs. If possible, abnormal laboratory results that meet the definition of an AE are reported as a clinical diagnosis rather than the abnormal value itself (e.g., "anemia" rather than "decreased blood count").

A "serious adverse event (SAL)" is defined as an AE that meets one of the following criteria:

TABLE 8

Serious Adverse Event Classification

| | |
|---|---|
| Fatal: | The AE resulted in death. |
| Life Threatening: | The AE placed the patient at immediate risk of death. This classification does not apply to an AE that hypothetically might cause death if it were more severe. |
| Hospitalization: | The AE required or prolonged an existing inpatient hospitalization. Hospitalizations for elective medical or surgical procedures or treatments planned before the signing of informed consent in the study or routine check-ups are not SAEs by this criterion. Admission to a palliative unit or hospice care facility is not considered to be a hospitalization. Hospitalizations or prolonged hospitalizations for scheduled therapy of the underlying cancer or study target disease need not be captured as SAEs. |
| Disabling/ Incapacitating: | Resulted in a substantial and permanent disruption of the patient's ability to carry out activities of daily living. |
| Congenital Anomaly or Birth Defect: | An adverse outcome in a child or fetus of a patient exposed to the study drug or study treatment regimen before conception or during pregnancy. |
| Important medical event: | The AE did not meet any of the above criteria, but could have jeopardized the patient and might have required medical or surgical intervention to prevent one of the outcomes listed above. |

"Overdose" is defined as the administration of a quantity of investigational medicinal product given per administration or cumulatively which is above the maximum dose, according to the protocol.

"Medication error" refers to an unintentional error in dispensing or administration of the investigational medicinal product not in accordance with the protocol described in this example.

"Misuse" is defined as any situation where the investigational medicinal product is intentionally and inappropriately used not in accordance with the protocol.

"Abuse" is defined as the persistent or sporadic intentional excessive use of the investigational medicinal product, which is accompanied by harmful physical or psychological effects.

Information pertaining to overdoses, medication errors, abuse, and misuse is collected as part of investigational medicinal product dosing information and/or as a protocol violation, as required.

Any AE associated with an overdose, medication error, misuse, or abuse of study drug is recorded on the AE eCRF with the diagnosis of the AE.

An "adverse event (AE) of special interest" can be any serious or non-serious AE that is of scientific or medical concern as defined by the sponsor and specific to the program, for which ongoing monitoring and rapid communication to the sponsor may be appropriate.

The following AEs of special interest are reported to the sponsor irrespective of regulatory seriousness criteria or causality within 24 hours.

Potential Drug-Induced Liver Injury

Any potential case of drug-induced liver injury as assessed by laboratory criteria for Hy's Law is considered as a protocol-defined event of special interest. The following laboratory abnormalities define potential Hy's Law cases: AST or ALT elevations that are >3×ULN with concurrent elevation (within 21 days of AST and/or ALT elevations) of total bilirubin >2× the ULN, except in patients with documented Gilbert's syndrome.

Asymptomatic Left Ventricular Systolic Dysfunction

In general, asymptomatic declines in LVEF should not be reported as AEs since LVEF data are collected separately in the eCRF. However, an asymptomatic decline in LVEF leading to a change in study treatment or discontinuation of study treatment is considered an event of special interest and a serious adverse event, and must be reported to the sponsor.

Cerebral Edema

Any event of cerebral edema not clearly attributable to progression of disease is reported as an Event of Special Interest.

AE severity is graded using the National Cancer Institute's Common Terminology Criteria for Adverse Events (NCI CTCAE), version 4.03. These criteria are provided in Table 12 at the end of this example.

AE severity and seriousness are assessed independently. Severity characterizes the intensity of an AE. Seriousness serves as a guide to the sponsor for defining regulatory reporting requirements (see definition of SAE above).

The relationship of an AE to all study drugs (tucatinib/placebo, capecitabine, and trastuzumab) is assessed using the guidelines presented in Table 9 below. An AE for which there has been no causal relationship reported requires follow-up to determine causality.

TABLE 9

AE Causal Relationship Guidelines

| | |
|---|---|
| | Is the AE/SAE suspected to be caused by the investigational product on the basis of facts, evidence, science-based rationales, and clinical judgment? |
| Related | The temporal relationship of the AE/SAE to investigational product administration makes a causal relationship possible AND other drugs, therapeutic interventions or underlying conditions do not provide sufficient explanation for the AE/SAE. |
| Not related | The temporal relationship of the AE/SAE to investigational product administration makes a causal relationship unlikely OR other drugs, therapeutic interventions, or underlying conditions provide a sufficient explanation for the AE/SAE. |

Procedures for Eliciting and Recording Adverse Events

Eliciting Adverse Events

The investigator assesses patients for the occurrence of AEs at all scheduled and unscheduled visits. The occurrence of AEs is sought by non-direct questioning of the patient at each visit. AEs may also be detected when they are volunteered by the patient during and between visits or through physical examination, or other assessments.

All AEs reported by the patient are reviewed by the investigator and must be recorded on the source documents and AE eCRFs provided.

Recording Adverse Events

Regardless of relationship to study drug, all serious and non-serious AEs that occur during the protocol-defined reporting period are to be recorded on the eCRF. SAEs occurring between pre-screening consent and main consent do not need to be documented, unless they are caused by a study procedure (e.g., biopsy).

The following information is assessed and recorded on the eCRF for each AE: description of the AE (including onset and resolution dates), severity (see, definitions above), relationship to each study drug (see, definitions above), outcome of each event, seriousness (see, definitions above), and action taken regarding each study drug.

Diagnosis vs. Signs or Symptoms

Whenever possible, the investigator groups signs or symptoms that constitute a single diagnosis under a single event term. For example, cough, rhinitis and sneezing might be grouped together as "upper respiratory tract infection."

Grouping of symptoms into a diagnosis is only done if each component sign or symptom is a medically confirmed component of a diagnosis as evidenced by standard medical textbooks. If any aspect of a sign or symptom does not fit into a classic pattern of the diagnosis, the individual symptom is reported as a separate event.

Progression of Underlying Malignancy

Since progression of underlying malignancy is being assessed as an efficacy variable, it is not reported as an AE or SAE. Symptomatic clinical deterioration due to disease progression as determined by the investigator also is not reported as an AE or SAE.

However, clinical symptoms of progression may be reported as AEs or SAEs if the symptom cannot be determined as exclusively due to progression of the underlying malignancy or does not fit the expected pattern of progression for the disease under study. In addition, complications from progression of the underlying malignancy are reported as AEs or SAEs.

Reporting Periods and Follow-Up of Adverse Events and Serious Adverse Events

All AEs identified during the clinical study are reported from the time the patient signs informed consent through the 30-day follow-up visit (tucatinib/placebo, capecitabine, or trastuzumab).

Any SAE that occurs after the patient discontinues study treatment considered by the investigator to be related to any study drug is reported to the sponsor.

All SAEs and AEs of special interest is followed until the acute event has resolved or stabilized, even if the patient discontinues study treatment prior to SAE resolution. Non-serious AEs are followed per the reporting period as noted above.

If a non-serious AE is ongoing at the 30-Day Follow-up Visit, the AE is recorded as ongoing.

Serious Adverse Event and Event of Special Interest Reporting Procedures

All SAEs/EOIs regardless of relationship to a study drug that occur after the first administration of a study drug must be reported to the sponsor on a SAE/EOI form within 24 hours of discovery of the event. An SAE occurring after informed consent but before administration of study drug and possibly related to a protocol procedure must also be reported to the sponsor within 24 hours of discovery of the event. Any new information or follow-up information pertaining to previously reported SAEs/EOIs is reported to the sponsor within 24 hours of becoming aware of the new or follow-up information.

For initial SAE/EOI reports, available case details are to be recorded on a SAE/EOI form. At a minimum, the following is included: patient number, AE term(s) (including serious criteria and onset date), study treatment, and causality assessment.

The processes for reporting and documenting SAEs and EOIs are provided in the study binder. Investigators are responsible for reporting these events to their TRB and/or IEC in accordance with federal and local institutional laws and regulations.

New or follow-up information should be faxed to the sponsor's clinical safety department. Medical concerns or questions regarding safety are directed to the medical monitor.

The factors below are considered when recording SAEs.

Death is an outcome of an event. The event that resulted in the death are recorded and reported on both an SAE/EOI form and the eCRF.

For hospitalizations, surgical or diagnostic procedures, the illness leading to the surgical or diagnostic procedure are recorded as the SAE, not the procedure itself.

Sponsor Safety Reporting to Regulatory Authorities

Investigators are required to report all SAEs to the sponsor. The sponsor conducts safety reporting to regulatory authorities, IRBs, and IECs as required per local regulatory reporting requirements. SAEs assessed as related and unexpected (as per IB) to tucatinib/placebo is unblinded by the sponsor to identify study treatment and is reported in accordance with local regulatory reporting requirements. Investigators receive all expedited reports in a blinded manner.

Pregnancy Reporting

Cases of pregnancy are reported through 6 months after the last dose of study drug (tucatinib, capecitabine, or trastuzumab, whichever is latest). If a patient or the female partner of a male patient becomes pregnant during participation in the study, the sponsor is notified. If a study participant becomes pregnant during administration of the drug, treatment is discontinued.

The investigator reports all pregnancies within 24 hours to the sponsor including the partners of male patients. The sponsor asks for follow up evaluation of the pregnancy, fetus, and child.

Abortion, whether accidental, therapeutic, or spontaneous, is reported as a SAE. Congenital anomaly or birth defects is also reported as a SAE as described above. All pregnancies are monitored for the full duration; all perinatal and neonatal outcomes are reported. Infants are followed for a minimum of 8 weeks. Pregnancy is reported to the sponsor's clinical safety department on a Pregnancy Report Form.

TABLE 10

Selected Strong Inhibitors and Inducer of CYP2C8 and Their Elimination Half-Lives

| Drug[a, b] | Elimination Half-life (hours) |
|---|---|
| Strong Inhibitors | |
| Gemfibrozil | 1-2 hours |
| Montelukast | 3-6 hours (drug insert) |
| Quercetin | <2 hours |
| Pioglitazone | 3-7 hours |
| Rosiglitazone | 16-24 hours |
| Trimethoprim | 8-10 hours |
| Strong Inducer | |
| Rifampin | 3-5 hours |

[a]FDA. "Drug Development and Drug Interactions: Table of Substrates, Inhibitors and Inducers" (www.fda.gov/Drugs/DevelopmentApprovalProcess/DevelopmentResources/DrugInteractionsLabeling/ucm093664.htm#potency).
[b]EMA. "Guideline on the investigation of drug interactions" www.ema.europa.eu/docs/en_GB/document_library/Scientific_guideline/2012/07/WC500129606.pdf

TABLE 11

Selected Strong and Moderate Inhibitors or Inducers of CYP3A4 and Their Elimination Half-Lives

| Drug[a, b, c] | Elimination Half-life (hours) |
|---|---|
| Strong Inhibitors | |
| Chloramphenicol | 4 hours |
| Macrolide Antibiotics | |
| Clarithromycin, | 3-7 hours |
| Erythromycin | 2 hours |
| Telithromycin | 10 hours |

TABLE 11-continued

Selected Strong and Moderate Inhibitors or Inducers of CYP3A4 and Their Elimination Half-Lives

| Drug[a, b, c] | Elimination Half-life (hours) |
|---|---|
| Azole Antifungals | |
| Itraconazole | 21 hours single dose, 64 hours steady state |
| ketoconazole (systemic) | 2-8 hours |
| Voriconazole | Dose dependent |
| Danazol | 24-26 hours |
| Nefazodone | 2-4 hours |
| Strong Inducers | |
| Barbiturates | Variable |
| Carbamazepine | 25-65 hours |
| Phenytoin | 7-42 hours |
| Rifampin | 3-4 hours |
| St. John's Wort | 9-43 hours |

[a]FDA. "Drug Development and Drug Interactions: Table of Substrates, Inhibitors and Inducers" (http://www.fda.gov/Drugs/DevelopmentApprovalProcess/DevelopmentResources/DrugInteractionsLabeling/ucm093664.htm#potency).
[b]EMA. "Guideline on the investigation of drug interactions" www.ema.europa.eu/docs/en_GB/document_library/Scientific_guideline/2012/07/WC500129606.pdf
[c]Strong CYP3A inhibitors are defined as those drugs that increase the AUC of oral midazolam or other CYP3A substrates ≥ 5-fold. Ritonavir, indinavir, nelfinavir, atazanivir, and saquinavir are also strong CYP3A3 inhibitors, but would not be used in this study as patients with known HIV are excluded.

TABLE 12

Adverse Event Severity Grading Scale (CTCAE Version 4.03)

| Severity | Grade | Description |
|---|---|---|
| Mild | 1 | Asymptomatic or mild symptoms; clinical or diagnostic observations only; intervention not indicated |
| Moderate | 2 | Minimal, local or noninvasive intervention indicated; limiting age-appropriate instrumental activities of daily living (ADL). Instrumental ADL refer to preparing meals, shopping for groceries or clothes, using the telephone, managing money, etc. |
| Severe | 3 | Medically significant but not immediately life-threatening; hospitalization or prolongation of hospitalization indicated; disabling; limiting self-care ADL. Self-care ADL refer to bathing, dressing and undressing, feeding self, using the toilet, taking medications, and not bedridden. |
| Life-threatening | 4 | Life-threatening consequences; urgent intervention indicated |
| Death | 5 | Death related to adverse event. |

TABLE 13

Drugs Accepted or Possibly Associated with Risk of QT Prolongation or Torsade de Pointes

| | Anti-infectives | Anti-psychotics | Opioid analgesics | Antihistamines |
|---|---|---|---|---|
| Accepted association | Clarithromycin Erythromycin Chloroquine Pentamidine | Haloperidol Chlorpromazine | Methadone | Terfaenadine |
| Possibly associated | Azithromycin Roxithromycin Telithromycin Moxifloxacin Amantadine | Resperidone Quetiapine Sertinodole Zisprasidone Lithium Clozapine | | |

TABLE 13-continued

Drugs Accepted or Possibly Associated with Risk of QT Prolongation or Torsade de Pointes

| | Antidepressants | Anti-emetics/ Gastric motility drugs | Anti-cancer | Anti-arrythmics |
|---|---|---|---|---|
| Accepted association | | Domperidone Cisapride | | Amiodarone Sotalol Disopyramide Dofetilide Procainamide Quinidine |
| Possibly associated | Escitalopram Venlaxafine | Ondansetron Dolasteron Granisetron | Tamoxifen Nilotinib Lapatinib | |

Guidance for Industry, E14 Clinical Evaluation of QT/QTc Interval Prolongation and Proarrhythmic Potential for Non-Antiarrhythmic Drugs. U.S. Department of Health and Human Services, Food and Drug Administration, Center for Drug Evaluation and Research (CDER), Center for Biologics Evaluation and Research (CBER) October 2005, ICH. Geoffrey K Isbister and Colin B Page. Drug induced QT prolongation: the measurement and assessment of the QT interval in clinical practice. Br J Clin Pharmacol. 2013 July; 76(1): 48-57.

| Glossary and Terms | |
|---|---|
| 5FU | 5-fluorouracil |
| ADL | activities of daily living |
| AE | adverse event |
| ALT/SGPT | alanine aminotransferase/serum glutamic-pyruvate transaminase |
| ANC | absolute neutrophil count |
| anti-HBc | antibodies to Hepatitis B core |
| anti-HCV | antibodies to Hepatitis C virus |
| API | active pharmaceutical ingredient |
| aPTT | activated partial thromboplastin time |
| AR | adverse reaction |
| AST/SGOT | aspartate aminotransferase/serum glutamic-oxaloacetic transaminase |
| AUC | area under the curve |
| BID | twice daily |
| BUN | blood urea nitrogen |
| CBC | complete blood count |
| CBR | clinical benefit rate |
| CHF | congestive heart failure |
| CI | confidence interval |
| $C_{max}$ | maximum concentration observed |
| CNS | central nervous system |
| CR | complete response |
| CT | computed tomography |
| CTCAE | Common Toxicity Criteria for Adverse Events |
| ctDNA | circulating tumor DNA |
| DCC | Data Coordinating Center |
| DDI | drug-drug interaction |
| DFS | disease-free survival |
| DMC | Data Monitoring Committee |
| DNA | deoxyribonucleic acid |
| DOR | Duration of Response |
| ECG | electrocardiogram |
| ECHO | echocardiogram |
| ECOG PS | Eastern Cooperative Oncology Group Performance Status |
| eCRF | electronic case report form |
| EGFR | epidermal growth factor receptor |
| EOI | event of interest |
| EU | European Union |
| FDA | Food and Drug Administration |
| FISH | fluorescence in situ hybridization |
| GCP | Good Clinical Practice |
| GI | gastrointestinal |
| HBsAg | hepatitis B surface antigen |
| HC | Health Canada |
| Hct | hematocrit |
| HER1 | human epidermal growth factor receptor 1 |
| HER2 | human epidermal growth factor receptor 2 |
| HER2+ | human epidermal growth factor receptor 2 positive |
| HIV | human immunodeficiency virus |
| HR | hazard ratio |
| IAR | infusion-associated reaction |

| | Glossary and Terms |
|---|---|
| IB | Investigator's Brochure |
| ICF | Informed Consent Form |
| ICH | International Conference on Harmonisation |
| IHC | immunohistochemistry |
| ILD | interstitial lung disease |
| INR | international normalized ratio |
| IUD | intrauterine device |
| IV | intravenous |
| IRB/IEC | Institutional Review Board/Independent Ethics Committee |
| IRT | Interactive Response Technology |
| ITT | Intent-to-Treat |
| kg | kilogram |
| LDH | lactate dehydrogenase |
| LFT | liver function test |
| LMD | leptomeningeal disease |
| LVEF | left ventricular ejection fraction |
| MedDRA | Medical Dictionary for Regulatory Activities |
| mg | milligram |
| mL | milliliter |
| mm | millimeter |
| MRI | magnetic resonance imaging |
| mRNA | messenger ribonucleic acid |
| MTD | maximum-tolerated dose |
| MUGA | multiple-gated acquisition scan |
| NCI | National Cancer Institute |
| ORR | objective response rate |
| OS | overall survival |
| PD | progressive disease |
| PET | positron emission tomography |
| PFS | progression-free survival |
| P-gp | P-glycoprotein |
| PIC | powder in capsule |
| PK | pharmacokinetics |
| PO | oral administration |
| PPE | palmar-plantar erythrodysaesthesia |
| PR | partial response |
| PT | prothrombin time |
| PVP-VA | polyvinylpyrrolidine-vinyl acetate copolymer |
| QTc | corrected QT |
| RANO-BM | Response Assessment in Neuro-Oncology-Brain Metastases |
| RD | recommended dose |
| RECIST | Response Evaluation Criteria In Solid Tumors |
| RNA | ribonucleic acid |
| RP2D | recommended Phase 2 dose |
| SAE | serious adverse event |
| SAP | statistical analysis plan |
| SD | stable disease |
| SOC | system organ class |
| SRS | stereotactic radiosurgery |
| SUSAR | suspected unexpected serious adverse reaction |
| T-DM1 | ado-trastuzumab emtansine or trastuzumab emtansine |
| TEAE | treatment-emergent adverse event |
| TKI | tyrosine kinase inhibitor |
| UGT1A1 | UDP-glucuronosyltransferase 1A1 |
| ULN | upper limit of normal |
| WBRT | whole brain radiation therapy |

REFERENCES

1. Cancer Incidence and Mortality Worldwide: IARC CancerBase No. 10 [Internet]. International Agency for Research on Cancer. 2010 [cited Jun. 6, 2013]. Available from: globocan.iarc.fr.
2. Group USCSW. United States Cancer Statistics: 1999-2009 Incidence and Mortality Web-based Report. In: Health and Human Services CfDCaP, and National Cancer Institute, editor. Atlanta, Ga. 2013.
3. Owens M A, Horten B C, Da Silva M M. HER2 amplification ratios by fluorescence in situ hybridization and correlation with immunohistochemistry in a cohort of 6556 breast cancer tissues. Clinical breast cancer. 2004; 5(1):63-9.
4. Giordano S H, Temin S, Kirshner J J, Chandarlapaty S, Crews J R, Davidson N E, et al. Systemic therapy for patients with advanced human epidermal growth factor receptor 2-positive breast cancer: American Society of Clinical Oncology clinical practice guideline. Journal of clinical oncology: official journal of the American Society of Clinical Oncology. 2014; 32(19):2078-99.
5. Slamon D J, Clark G M, Wong S G, Levin W J, Ullrich A, McGuire W L. Human breast cancer: correlation of relapse and survival with amplification of the HER-2/neu oncogene. Science. 1987; 235(4785):177-82.
6. Slamon D J, Leyland-Jones B, Shak S, Fuchs H, Paton V, Bajamonde A, et al. Use of chemotherapy plus a monoclonal antibody against HER2 for metastatic breast cancer that overexpresses HER2. The New England journal of medicine. 2001; 344(11):783-92.
7. Verma S, Miles D, Gianni L, Krop I E, Welslau M, Baselga J, et al. Trastuzumab emtansine for HER2-positive advanced breast cancer. The New England journal of medicine. 2012; 367(19):1783-91.
8. Baselga J, Cortes J, Kim S B, Im S A, Hegg R, Im Y H, et al. Pertuzumab plus trastuzumab plus docetaxel for metastatic breast cancer. The New England journal of medicine. 2012; 366(2):109-19.
9. Geyer C E, Forster J, Lindquist D, Chan S, Romieu C G, Pienkowski T, et al. Lapatinib plus capecitabine for HER2-positive advanced breast cancer. The New England journal of medicine. 2006; 355(26):2733-43.
10. (lapatinib) T. [package insert]: Novartis; 2015 [cited 2015]. Available from: www.gsksource.com/pharma/content/dam/GlaxoSmithKline/U S/en/Prescribing_Information/Tykerb/pdf/TYKERB-PI-PIL.PDF.
11. Vogel C L, Cobleigh M A, Tripathy D, Gutheil J C, Harris L N, Fehrenbacher L, et al. Efficacy and safety of trastuzumab as a single agent in first-line treatment of HER2-overexpressing metastatic breast cancer. Journal of clinical oncology: official journal of the American Society of Clinical Oncology. 2002; 20(3):719-26.
12. Lu Y, Zi X, Zhao Y, Mascarenhas D, Pollak M. Insulin-like growth factor-I receptor signaling and resistance to trastuzumab (Herceptin). Journal of the National Cancer Institute. 2001; 93(24):1852-7.
13. Scaltriti M, Rojo F, Ocana A, Anido J, Guzman M, Cortes J, et al. Expression of p95HER2, a truncated form of the HER2 receptor, and response to anti-HER2 therapies in breast cancer. Journal of the National Cancer Institute. 2007; 99(8):628-38.
14. Pohlmann P R, Mayer I A, Mernaugh R. Resistance to Trastuzumab in Breast Cancer. Clinical cancer research: an official journal of the American Association for Cancer Research. 2009; 15(24):7479-91.
15. Nahta R, Esteva F J. HER2 therapy: molecular mechanisms of trastuzumab resistance. Breast cancer research: BCR. 2006; 8(6):215.
16. Baselga J, Bradbury I, Eidtmann H, Di Cosimo S, de Azambuja E, Aura C, et al. Lapatinib with trastuzumab for HER2-positive early breast cancer (NeoALTTO): a randomised, open-label, multicentre, phase 3 trial. Lancet. 2012; 379(9816):633-40.
17. Blackwell K L, Burstein H J, Storniolo A M, Rugo H, Sledge G, Koehler M, et al. Randomized study of Lapatinib alone or in combination with trastuzumab in women with ErbB2-positive, trastuzumab-refractory metastatic breast cancer. Journal of clinical oncology: official journal of the American Society of Clinical Oncology. 2010; 28(7):1124-30.

18. Blackwell K L, Burstein H J, Storniolo A M, Rugo H S, Sledge G, Aktan G, et al. Overall survival benefit with lapatinib in combination with trastuzumab for patients with human epidermal growth factor receptor 2-positive metastatic breast cancer: final results from the EGF104900 Study. Journal of clinical oncology: official journal of the American Society of Clinical Oncology. 2012; 30(21):2585-92.
19. Network NCC. NCCN Guidelines®& Clinical Resources 2013 [cited 2013 Aug. 15]. Available from: www.nccn.org.
20. Clayton A J, Danson S, Jolly S, Ryder W D, Burt P A, Stewart A L, et al. Incidence of cerebral metastases in patients treated with trastuzumab for metastatic breast cancer. British journal of cancer. 2004; 91(4):639-43.
21. Goldhirsch A, Gelber R D, Piccart-Gebhart M J, de Azambuja E, Procter M, Suter T M, et al. 2 years versus 1 year of adjuvant trastuzumab for HER2-positive breast cancer (HERA): an open-label, randomised controlled trial. Lancet. 2013; 382(9897):1021-8.
22. Pestalozzi B C, Holmes E, de Azambuja E, Metzger-Filho O, Hogge L, Scullion M, et al. CNS relapses in patients with HER2-positive early breast cancer who have and have not received adjuvant trastuzumab: a retrospective substudy of the HERA trial (BIG 1-01). The Lancet Oncology. 2013; 14(3):244-8.
23. Lin N U, Bellon J R, Winer E P. CNS metastases in breast cancer. Journal of clinical oncology: official journal of the American Society of Clinical Oncology. 2004; 22(17):3608-17.
24. Ekenel M, Hormigo A M, Peak S, Deangelis L M, Abrey L E. Capecitabine therapy of central nervous system metastases from breast cancer. Journal of neuro-oncology. 2007; 85(2):223-7.
25. Ramakrishna N, Temin S, Chandarlapaty S, Crews J R, Davidson N E, Esteva F J, et al. Recommendations on disease management for patients with advanced human epidermal growth factor receptor 2-positive breast cancer and brain metastases: American Society of Clinical Oncology clinical practice guideline. Journal of clinical oncology: official journal of the American Society of Clinical Oncology. 2014; 32(19):2100-8.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and sequence accession numbers cited herein are hereby incorporated by reference in their entirety for all purposes.

What is claimed is:

1. A method for treating a HER2-positive colorectal cancer in a human subject, the method comprising:
administering a combination therapy comprising an anti-HER2 antibody and tucatinib, thereby treating the HER2-positive colorectal cancer.
2. The method of claim 1, wherein the anti-HER2 antibody is a member selected from the group consisting of trastuzumab, pertuzumab, ado-trastuzumab emtansine, margetuximab, and a combination thereof.
3. The method of claim 1, wherein the anti-HER2 antibody is trastuzumab.
4. The method of claim 3, wherein the trastuzumab is administered intravenously or subcutaneously.
5. The method of claim 3, wherein the trastuzumab is administered at an amount of about 6 mg to 8 mg per kg of the subject's body weight once every three weeks.
6. The method of claim 3, wherein the tucatinib is administered orally.
7. The method of claim 4, wherein the tucatinib is administered orally.
8. The method of claim 5, wherein the tucatinib is administered orally.
9. The method of claim 3, wherein the tucatinib is administered in an amount of about 300 mg twice per day.
10. The method of claim 4, wherein the tucatinib is administered in an amount of about 300 mg twice per day.
11. The method of claim 5, wherein the tucatinib is administered in an amount of about 300 mg twice per day.
12. The method of claim 3, wherein the HER2-positive colorectal cancer is an unresectable locally advanced colorectal cancer or a metastatic colorectal cancer.
13. The method of claim 9, wherein the HER2-positive colorectal cancer is an unresectable locally advanced colorectal cancer or a metastatic colorectal cancer.
14. The method of claim 3, wherein the HER2-positive colorectal cancer comprises a cell that has a wild-type KRAS exon 2 genotype, a wild-type NRAS genotype, or a wild-type BRAF genotype.
15. The method of claim 9, wherein the HER2-positive colorectal cancer comprises a cell that has a wild-type KRAS exon 2 genotype, a wild-type NRAS genotype, or a wild-type BRAF genotype.
16. The method of claim 3, wherein the subject has a HER2-positive colorectal cancer which is relapsed or refractory to a standard of care.
17. The method of claim 9, wherein the subject has a HER2-positive colorectal cancer which is relapsed or refractory to a standard of care.
18. The method of claim 3, wherein treating the subject results in a tumor growth inhibition (TGI) index of at least about 85%.
19. The method of claim 9, wherein treating the subject results in a tumor growth inhibition (TGI) index of at least about 85%.
20. The method of claim 3, wherein the combination of the trastuzumab and tucatinib is synergistic.
21. The method of claim 9, wherein the combination of the trastuzumab and tucatinib is synergistic.
22. The method of claim 1, wherein the anti-HER2 antibody is trastuzumab; wherein the trastuzumab is administered intravenously or subcutaneously at an amount of about 6 mg to 8 mg per kg of the subject's body weight once every three weeks; and wherein the tucatinib is administered orally in an amount of about 300 mg twice per day.
23. The method of claim 3, wherein the combination therapy further comprises a chemotherapeutic agent.

* * * * *

UNITED STATES PATENT AND TRADEMARK OFFICE
CERTIFICATE OF CORRECTION

| | |
|---|---|
| PATENT NO. | : 11,666,572 B2 |
| APPLICATION NO. | : 17/530265 |
| DATED | : June 6, 2023 |
| INVENTOR(S) | : Scott Peterson and Luke Walker |

It is certified that error appears in the above-identified patent and that said Letters Patent is hereby corrected as shown below:

On the Title Page

Column 2 (item (56) Other Publications), Line 1, delete "Supplements," and insert --Supplement 5,--.

Signed and Sealed this
Sixteenth Day of April, 2024

*Katherine Kelly Vidal*

Katherine Kelly Vidal
*Director of the United States Patent and Trademark Office*